United States Patent [19]

Trulson et al.

[11] Patent Number: 5,578,832
[45] Date of Patent: Nov. 26, 1996

[54] METHOD AND APPARATUS FOR IMAGING A SAMPLE ON A DEVICE

[75] Inventors: Mark Trulson, Santa Clara; David Stern, Mountain View; Peter Fiekowsky, Los Altos; Richard Rava, Palo Alto; Ian Walton, Menlo Park; Stephen P. A. Fodor, Palo Alto, all of Calif.

[73] Assignee: Affymetrix, Inc., Santa Clara, Calif.

[21] Appl. No.: 301,051

[22] Filed: Sep. 2, 1994

[51] Int. Cl.$^6$ .................................................. G01N 21/63
[52] U.S. Cl. ................................. 250/458.1; 250/459.1; 250/201.2
[58] Field of Search ........................... 250/458.1, 459.1, 250/461.1, 462.1, 201.2, 201.3, 201.4

[56] References Cited

U.S. PATENT DOCUMENTS

| | | |
|---|---|---|
| 4,180,739 | 12/1979 | Abu-Shymays . |
| 4,772,125 | 9/1988 | Yoshimura et al. ............. 250/458.1 X |
| 4,786,170 | 11/1988 | Groebler . |
| 4,844,617 | 7/1989 | Kelderman et al. ............. 250/201.3 X |
| 5,061,075 | 10/1991 | Alfano et al. .................... 250/461.2 X |
| 5,091,652 | 2/1992 | Mathies et al. . |
| 5,143,854 | 9/1992 | Pirrung et al. . |
| 5,192,980 | 3/1993 | Dixon . |
| 5,198,871 | 3/1993 | Hill, Jr. et al. .................. 250/458.1 X |
| 5,304,810 | 4/1994 | Amos ................................ 250/458.1 |
| 5,424,186 | 6/1995 | Fodor et al. ............................ 435/6 |

FOREIGN PATENT DOCUMENTS

| | | | |
|---|---|---|---|
| 3-6444 | 1/1991 | Japan | ................................. 250/458.1 |
| WO93/02992 | 6/1992 | WIPO . | |

Primary Examiner—Carolyn E. Fields
Assistant Examiner—Edward J. Glick
Attorney, Agent, or Firm—Townsend & Townsend & Crew LLP

[57] ABSTRACT

The present invention provides methods and systems for detecting a labeled marker on a sample located on a support. The imaging system comprises a body for immobilizing the support, an excitation radiation source and excitation optics to generate and direct the excitation radiation at the sample. In response, labeled material on the sample emits radiation which has a wavelength that is different from the excitation wavelength, which radiation is collected by collection optics and imaged onto a detector which generates an image of the sample.

22 Claims, 26 Drawing Sheets

ABI emission data
Data from files A056 & A057
Using normalized emission cross sections

|  |  | normalized emission cross sections | | | |
|---|---|---|---|---|---|
| image plane = | emiss wave | FAM | JOE | TAM | ROX |
| 11 | 511 | 0.0311585 | 0.0019068 | 0.001987 | 0.004961 |
| 27 | 553 | 0.025249 | 0.050401 | 0.0172558 | 0.0083 |
| 36 | 578 | 0.01777 | 0.024511 | 0.05072 | 0.04075 |
| 45 | 608 | 0.0097 | 0.0144901 | 0.02481 | 0.04227 | trace =        0.1745495 normalized version of above (trace = 4)

| | | | |
|---|---|---|---|
| 0.71403241 | 0.04369649 | 0.04553436 | 0.11368695 |
| 0.57860951 | 1.15499615 | 0.39543625 | 0.19020392 |
| 0.40721973 | 0.5616974 | 1.16230639 | 0.93383252 |
| 0.22228651 | 0.3320571 | 0.56854932 | 0.96866505 | trace =        4 inverse of the normalized intensity matrix:

|  | 511 nm | 553 nm | 578 nm | 608 nm |
|---|---|---|---|---|
| FAM | 1.45212017 | -0.01938876 | 0.05906452 | -0.22356094 |
| JOE | -0.66182998 | 1.03115421 | -0.49929123 | 0.35653835 |
| TAMRA | -0.19581025 | -0.39948847 | 1.80596059 | -1.63959605 |
| ROX | 0.00857509 | -0.11455282 | -0.90239007 | 1.92377615 |
| trace | 6.21301112 | | | | normalized inverse matrix (trace = 4)

|  | 511 nm | 553 nm | 578 nm | 608 nm |
|---|---|---|---|---|
| FAM | 0.93488979 | -0.01248268 | 0.03802634 | -0.14393081 |
| JOE | -0.4260929 | 0.66386761 | -0.32144879 | 0.22954303 |
| TAMRA | -0.12606464 | -0.25719476 | 1.16269587 | -1.05558868 |
| ROX | 0.00552073 | -0.07375028 | -0.52096794 | 1.23854673 |
| trace | 4 | | | |

METHOD AND APPARATUS FOR IMAGING A SAMPLE ON A DEVICE

COPYRIGHT NOTICE

A portion of the disclosure of this patent document contains material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

BACKGROUND OF THE INVENTION

The present invention relates to the field of imaging. In particular, the present invention provides methods and apparatus for high speed imaging of a sample containing labeled markers with high sensitivity and resolution.

Methods and systems for imaging samples containing labeled markers such as confocal microscopes are commercially available. These systems, although capable of achieving high resolution with good depth discrimination, have a relatively small field of view. In fact, the system's field of view is inversely related to its resolution. For example, a typical 40× microscope objective, which has a 0.25 µm resolution, has a field size of only about 500 µm. Thus, confocal microscopes are inadequate for applications requiring high resolution and large field of view simultaneously.

Other systems, such as those discussed in U.S. Pat. No. 5,143,854 (Pirrung et al.), PCT WO 92/10092, and U. S. patent application Ser. No. 08/195,889, filed Feb. 10, 1994, incorporated herein by reference for all purposes, are also known. These systems include an optical train which directs a monochromatic or polychromatic light source to about a 5 micron (µm) diameter spot at its focal plane. A photon counter detects the emission from the device in response to the light. The data collected by the photon counter represents one pixel or data point of the image. Thereafter, the light scans another pixel as the translation stage moves the device to a subsequent position.

As disclosed, these systems resolve the problem encountered by confocal microscopes. Specifically, high resolution and a large field of view are simultaneously obtained by using the appropriate objective lens and scanning the sample one pixel at a time. However, this is achieved by sacrificing system throughput. As an example, an array of material formed using the pioneering fabrication techniques, such as those disclosed in U.S. Pat. No. 5,143,854 (Pirrung et al.), U.S. patent application Ser. No. 08/143,312, and U.S. patent application Ser. No. 08/255,682, incorporated herein by reference for all purposes, may have about $10^5$ sequences in an area of about 13 mm×13 mm. Assuming that 16 pixels are required for each member of the array ($1.6 \times 10^6$ total pixels), the image can take over an hour to acquire.

In some applications, a full spectrally resolved image of the sample may be desirable. The ability to retain the spectral information permits the use of multi-labeling schemes, thereby enhancing the level of information obtained. For example, the microenvironment of the sample may be examined using special labels whose spectral properties are sensitive to some physical property of interest. In this manner, pH, dielectric constant, physical orientation, and translational and/or rotational mobility may be determined.

From the above, it is apparent that improved methods and systems for imaging a sample are desired.

SUMMARY OF THE INVENTION

Methods and systems for detecting a labeled marker on a sample located on a support are disclosed. The imaging system comprises a body for immobilizing the support. Excitation radiation, from an excitation source having a first wavelength, passes through excitation optics. The excitation optics cause the excitation radiation to excite a region on the sample. In response, labeled material on the sample emits radiation which has a wavelength that is different from the excitation wavelength. Collection optics then collect the emission from the sample and image it onto a detector. The detector generates a signal proportional to the amount of radiation sensed thereon. The signal represents an image associated with the plurality of regions from which the emission originated. A translator is employed to allow a subsequent plurality of regions on said sample to be excited. A processor processes and stores the signal so as to generate a 2-dimensional image of said sample.

In one embodiment, excitation optics focus excitation light to a line at a sample, simultaneously scanning or imaging a strip of the sample. Surface bound labeled targets from the sample fluoresce in response to the light. Collection optics image the emission onto a linear array of light detectors. By employing confocal techniques, substantially only emission from the light's focal plane is imaged. Once a strip has been scanned, the data representing the 1-dimensional image are stored in the memory of a computer. According to one embodiment, a multi-axis translation stage moves the device at a constant velocity to continuously integrate and process data. As a result, a 2-dimensional image of the sample is obtained.

In another embodiment, collection optics direct the emission to a spectrograph which images an emission spectrum onto a 2-dimensional array of light detectors. By using a spectrograph, a full spectrally resolved image of the sample is obtained.

The systems may include auto-focusing feature to maintain the sample in the focal plane of the excitation light throughout the scanning process. Further, a temperature controller may be employed to maintain the sample at a specific temperature while it is being scanned. The multi-axis translation stage, temperature controller, auto-focusing feature, and electronics associated with imaging and data collection are managed by an appropriately programmed digital computer.

In connection with another aspect of the invention, methods for analyzing a full spectrally resolved image are disclosed. In particular, the methods include, for example, a procedure for deconvoluting the spectral overlap among the various types of labels detected. Thus, a set of images, each representing the surface densities of a particular label can be generated.

A further understanding of the nature and advantages of the inventions herein may be realized by reference to the remaining portions of the specification and the attached drawings.

BRIEF DESCRIPTION OF THE DRAWINGS

FIG. 19 shows the emission cross section matrix elements obtained from the emission spectra of FIG. 13;

DESCRIPTION OF THE PREFERRED EMBODIMENT CONTENTS

Figure 1:
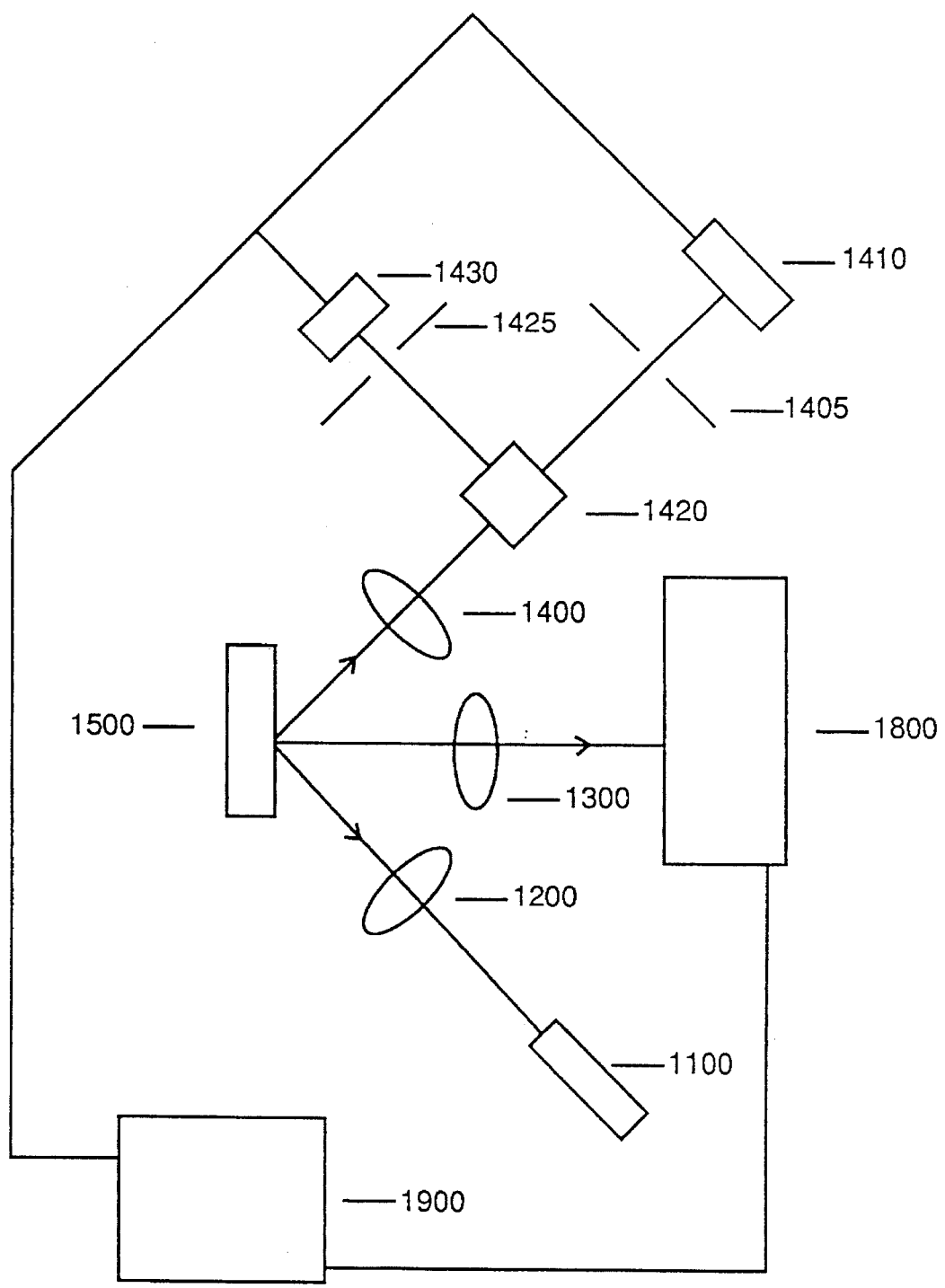
FIG. 1 shows a block diagram of an imaging system.

I. Definitions
II. General
  a. Introduction
  b. Overview of the Imaging System
III. Detailed Description of One Embodiment of the Imaging System
  a. Detection Device
  b. Data acquisition
IV. Detailed Description of an Alternative Embodiment of the Imaging System
  a. Detection Device
  b. Data Acquisition
  c. Postprocessing of the Monochromatic Image Set
  d. Example of spectral deconvolution of a 4-fluorophore system
V. Detailed Description of Another Embodiment of the Imaging System I. Definitions The following terms are intended to have the following general meanings as they are used herein:

1. Complementary: Refers to the topological compatibility or matching together of interacting surfaces of a probe molecule and its target. Thus, the target and its probe can be described as complementary, and furthermore, the contact surface characteristics are complementary to each other.

2. Probe: A probe is a surface-immobilized molecule that is recognized by a particular target. Examples of probes that can be investigated by this invention include, but are not restricted to, agonists and antagonists for cell membrane receptors, toxins and venoms, viral epitopes, hormones (e.g., opioid peptides, steroids, etc.), hormone receptors, peptides, enzymes, enzyme substrates, cofactors, drugs, lectins, sugars, oligonucleotides, nucleic acids, oligosaccharides, proteins, and monoclonal antibodies.

3. Target: A molecule that has an affinity for a given probe. Targets may be naturally-occurring or manmade molecules. Also, they can be employed in their unaltered state or as aggregates with other species. Targets may be attached, covalently or noncovalently, to a binding member, either directly or via a specific binding substance. Examples of targets which can be employed by this invention include, but are not restricted to, antibodies, cell membrane receptors, monoclonal antibodies and antisera reactive with specific antigenic determinants (such as on viruses, cells or other materials), drugs, oligonucleotides, nucleic acids, peptides, cofactors, lectins, sugars, polysaccharides, cells, cellular membranes, and organelles. Targets are sometimes referred to in the art as anti-probes. As the term targets is used herein, no difference in meaning is intended. A "Probe Target Pair" is formed when two macromolecules have combined through molecular recognition to form a complex.

II. General a. Introduction

The present invention provides methods and apparatus for obtaining a highly sensitive and resolved image at a high speed. The invention will have a wide range of uses, particularly, those requiring quantitative study of a microscopic region from within a larger region, such as 1 $\mu m^2$ over 100 $mm^2$. For example, the invention will find application in the field of histology (for studying histochemical stained and immunological fluorescent stained images), video microscopy, or fluorescence in situ hybridization. In one application, the invention herein is used to image an array of probe sequences fabricated on a support.

The support on which the sequences are formed may be composed from a wide range of material, either biological, nonbiological, organic, inorganic, or a combination of any of these, existing as particles, strands, precipitates, gels, sheets, tubing, spheres, containers, capillaries, pads, slices, films, plates, slides, etc. The substrate may have any convenient shape, such as a disc, square, sphere, circle, etc. The substrate is preferably flat but may take on a variety of alternative surface configurations. For example, the substrate may contain raised or depressed regions on which a sample is located. The substrate and its surface preferably form a rigid support on which the sample can be formed. The substrate and its surface are also chosen to provide appropriate light-absorbing characteristics. For instance, the substrate may be a polymerized Langmuir Blodgett film, functionalized glass, Si, Ge, GaAs, GaP, $SiO_2$, $SIN_4$, modified silicon, or any one of a wide variety of gels or polymers such as (poly)tetrafluoroethylene, (poly)vinylidenedifluoride, polystyrene, polycarbonate, or combinations thereof. Other substrate materials will be readily apparent to those of skill in the art upon review of this disclosure. In a preferred embodiment the substrate is flat glass or silica.

According to some embodiments, the surface of the substrate is etched using well known techniques to provide for desired surface features. For example, by way of the formation of trenches, v-grooves, mesa structures, or the like, the synthesis regions may be more closely placed within the focus point of impinging light. The surface may also be provided with reflective "mirror" structures for maximization of emission collected therefrom.

Surfaces on the solid substrate will usually, though not always, be composed of the same material as the substrate. Thus, the surface may be composed of any of a wide variety of materials, for example, polymers, plastics, resins, polysaccharides, silica or silica-based materials, carbon, metals, inorganic glasses, membranes, or any of the above-listed substrate materials. In one embodiment, the surface will be optically transparent and will have surface Si-0H functionalities, such as those found on silica surfaces.

The array of probe sequences may be fabricated on the support according to the pioneering techniques disclosed in U.S. Pat. No. 5,143,854, PCT WO 92/10092, or U. S. application Ser. No. 07/624,120, filed Dec. 6, 1990, incorporated herein by reference for all purposes. The combination of photolithographic and fabrication techniques may, for example, enable each probe sequence ("feature") to occupy a very small area ("site") on the support. In some embodiments, this feature site may be as small as a few microns or even a single molecule. For example, about $10^5$ to $10^6$ features may be fabricated in an area of only 12.8 mm$^2$. Such probe arrays may be of the type known as Very Large Scale Immobilized Polymer Synthesis (VLSIPS™).

The probe arrays will have a wide range of applications. For example, the probe arrays may be designed specifically to detect genetic diseases, either from acquired or inherited mutations in an individual DNA. These include genetic diseases such as cystic fibrosis, diabetes, and muscular dystrophy, as well as acquired diseases such as cancer (P53 gene relevant to some cancers), as disclosed in U.S. Pat. application Ser. No. 08/143,312, already incorporated by reference.

Genetic mutations may be detected by a method known as sequencing by hybridization. In sequencing by hybridization, a solution containing one or more targets to be sequenced (i.e., samples from patients) contacts the probe array. The targets will bind or hybridize with complementary probe sequences. Generally, the targets are labeled with a fluorescent marker, radioactive isotopes, enzymes, or other types of markers. Accordingly, locations at which targets hybridize with complimentary probes can be identified by locating the markers. Based on the locations where hybridization occur, information regarding the target sequences can be extracted. The existence of a mutation may be determined by comparing the target sequence with the wild type.

The interaction between targets and probes can be characterized in terms of kinetics and thermodynamics. As such, it may be necessary to interrogate the array while in contact with a solution of labeled targets. Consequently, the detection system must be extremely selective, with the capacity to discriminate between surface-bound and solution-born targets. Also, in order to perform a quantitative analysis, the high-density volume of the probe sequences requires the system to have the capacity to distinguish between each feature site.

b. Overview of the Imaging System

An image is obtained by detecting the electro-magnetic radiation emitted by the labels on the sample when it is illuminated. Emission from surface-bound and solution-free targets is distinguished through the employment of confocal and auto-focusing techniques, enabling the system to image substantially only emission originating from the surface of the sample. Generally, the excitation radiation and response emission have different wavelengths. Filters having high transmissibility in the label's emission band and low transmissibility in the excitation wavelength may be utilized to virtually eliminate the detection of undesirable emission. These generally include emission from out-of-focus planes or scattered excitation illumination as potential sources of background noise.

FIG. 1 is an optical and electronic block diagram illustrating the imaging system according to the present invention. Illumination of a sample 1500 may be achieved by exposing the sample to electromagnetic radiation from an excitation source 1100. Various excitation sources may be used, including those which are well known in the art such as an argon laser, diode laser, helium-neon laser, dye laser, titanium sapphire laser, Nd:YAG laser, arc lamp, light emitting diodes, any incandescent light source, or other illuminating device.

Typically, the source illuminates the sample with an excitation wavelength that is within the visible spectrum, but other wavelengths (i.e., near ultraviolet or near infrared spectrum) may be used depending on the application (i.e., type of markers and/or sample). In some embodiments, the sample is excited with electromagnetic radiation having a wavelength at or near the absorption maximum of the species of label used. Exciting the label at such a wavelength produces the maximum number of photons emitted. For example, if fluorescein (absorption maximum of 488 nm) is used as a label, an excitation radiation having a wavelength of about 488 nm would induce the strongest emission from the labels.

In instances where a multi-labeling scheme is utilized, a wavelength which approximates the mean of the various candidate labels' absorption maxima may be used. Alternatively, multiple excitations may be performed, each using a wavelength corresponding to the absorption maximum of a specific label. Table I lists examples of various types of fluorophores and their corresponding absorption maxima.

TABLE I

| Candidate Fluorophores | Absorption Maxima |
| --- | --- |
| Fluorescein | 488 nm |
| Dichloro-fluorescein | 525 nm |
| Hexachloro-fluorescein | 529 nm |
| Tetramethylrhodamine | 550 nm |
| Rodamine X | 575 nm |
| Cy3 ™ | 550 nm |
| Cy5 ™ | 650 nm |
| Cy7 ™ | 750 nm |
| IRD40 | 785 nm |

The excitation source directs the light through excitation optics 1200, which focus the light at the sample. The excitation optics transform the light into a "line" sufficient to illuminate a row of the sample. Although the Figure illustrates a system that images one vertical row of the sample at a time, it can easily be configured to image the sample horizontally or to employ other detection scheme. In this manner, a row of the sample (i.e., multiple pixels) may be imaged simultaneously, increasing the throughput of the imaging systems dramatically.

Generally, the excitation source generates a beam with a Gaussian profile. In other words, the excitation energy of the line peaks flatly near the center and diminishes therefrom (i.e., non-uniform energy profile). Illuminating the sample with a non-uniform energy profile will produce undesirable results. For example, the edge of the sample that is illuminated by less energetic radiation would appear more dim relative to the center. This problem is resolved by expanding the line to permit the central portion of the Gaussian profile to illuminate the sample.

The width of the line (or the slit aperture) determines the spatial resolution of the image. The narrower the line, the more resolved the image. Typically, the line width is dictated by the feature size of sample. For example, if each probe sequence occupies a region of about 50 µm, then the minimum width is about 50 µm. Preferably, the width should be several times less than the feature size to allow for oversampling.

Excitation optics may comprise various optical elements to achieved the desired excitation geometry, including but not limited to microscope objectives, optical telescopes, cylindrical lens, cylindrical telescopes, line generator lenses, anamorphic prisms, combination of lenses, and/or optical masks. The excitation optics may be configured to illuminate the sample at an angle so as to decouple the excitation and collection paths. As a result, the burden of separating the light paths from each other with expensive dichroic mirrors or other filters is essentially eliminated. In one embodiment, the excitation radiation illuminates the sample at an incidence of about 45°. This configuration substantially improves the system's depth discrimination since emission from out-of-focus planes is virtually undetected. This point will subsequently be discussed in more detail in connection with FIG. 2.

As the incident light is reflected from the sample, it passes through focusing optics 1400, which focus the reflected illumination line to a point. A vertical spatial slit 1405 and light detector 1410 are located behind the focusing optics. Various light detectors may be used, including photodiodes, avalanche photodiodes, phototransistors, vacuum photodiodes, photomultiplier tubes, and other light detectors. The focusing optics, spatial slit, and light detector serve to focus the sample in the focal plane of the excitation light. In one embodiment, the light is focused at about the center of the slit when the sample is located in the focal plane of the incident light. Using the light detector to sense the energy, the system can determine when the sample is in focus. In some applications, the slit may be eliminated by employing a split photodiode (bi-cell or quadrant detector), position-sensitive photodiode, or position-sensitive photomultiplier.

The line illumination technique presents certain concerns such as maintaining the plane of the sample perpendicular to the optical axis of the collection optics. If the sample is not aligned properly, image distortion and intensity variation may occur. Various methods, including shims, tilt stage, gimbal mount, goniometer, air pressure or pneumatic bearings or other technique may be employed to maintain the sample in the correct orientation. In one embodiment, a beam splitter 1420 may be strategically located to direct a portion of the beam reflected from the sample. A horizontal spatial slit 1425 and light detector 1430, similar to those employed in the auto-focusing technique, may be used to sense when the plane of the sample is perpendicular to the optical axis of the collection optics.

In response to the excitation light, the labeled targets fluoresce (i.e., secondary radiation). The emission, is collected by collection optics 1300 and imaged onto detector 1800. A host of lenses or combination of lenses may be used to comprise collection optics, such as camera lenses, microscope objectives, or a combination of lenses. The detector may be an array of light detectors used for imaging, such as charge-coupled devices (CCD) or charge-injection devices (CID). Other applicable detectors may include image-intensifier tubes, image orthicon tube, vidicon camera type, image dissector tube, or other imaging devices. Generally, the length of the CCD array is chosen to sufficiently detect the image produced by the collection optics. The magnification power of the collection optics dictates the dimension of the image. For instance, a 2× collection optics produces an image equal to about twice the height of the sample.

The magnification of the collection optics and the sensitivity of detector 1800 play an important role in determining the spatial resolution capabilities of the system. Generally, the spatial resolution of the image is restricted by the pixel size of detector 1800. For example, if the size of each pixel in the detector is 25 µm$^2$, then the best image resolution at 1× magnification is about 25 µm. However, by increasing the magnification power of the collection optics, a higher spatial resolution may be achieved with a concomitant reduction of field of view. As an illustration, increasing the magnification of the collection optics to 5 would increase the resolution by a factor of 5 (from 25 µm to 5 µm).

A filter, such as a long pass glass filter, long pass or band pass dielectric filter, may be located in front of detector 1800 to prevent imaging of unwanted emission, such as incident light scattered by the substrate. Preferably, the filter transmits emission having a wavelength at or greater than the fluorescence and blocks emission having shorter wavelengths (i.e., blocking emission at or near the excitation wavelength).

Once a row of fluorescent data has been collected or integrated), the system begins to image a subsequent row. This may be achieved by mounting the sample on a translation stage and moving it across the excitation light. Alternatively, Galvo scanners or rotating polyhedral mirrors may be employed to scan the excitation light across the sample. A complete 2-dimensional image of the sample is generated by combining the rows together.

The amount of time required to obtain the 2-dimensional image depends on several factors, such as the intensity of the laser, the type of labels used, the detector sensitivity, noise level, and resolution desired. In one embodiment, a typical integration period of a single row may be about 40 msec. Given that, a 14 µm resolution image of a 12.8 mm$^2$ sample can be acquired in less than 40 seconds.

Thus, the present invention acquires images as fast as conventional confocal microscope while achieving the same resolution, but with a much larger field of view. In one dimension, the field of view is dictated by the translation stage and can be arbitrarily large (determined by the distance it translates during one integration period). In the other dimension, the field of view is limited by the objective lens. However, this limitation may be eliminated employing a translation stage for that dimension.

Figure 2:
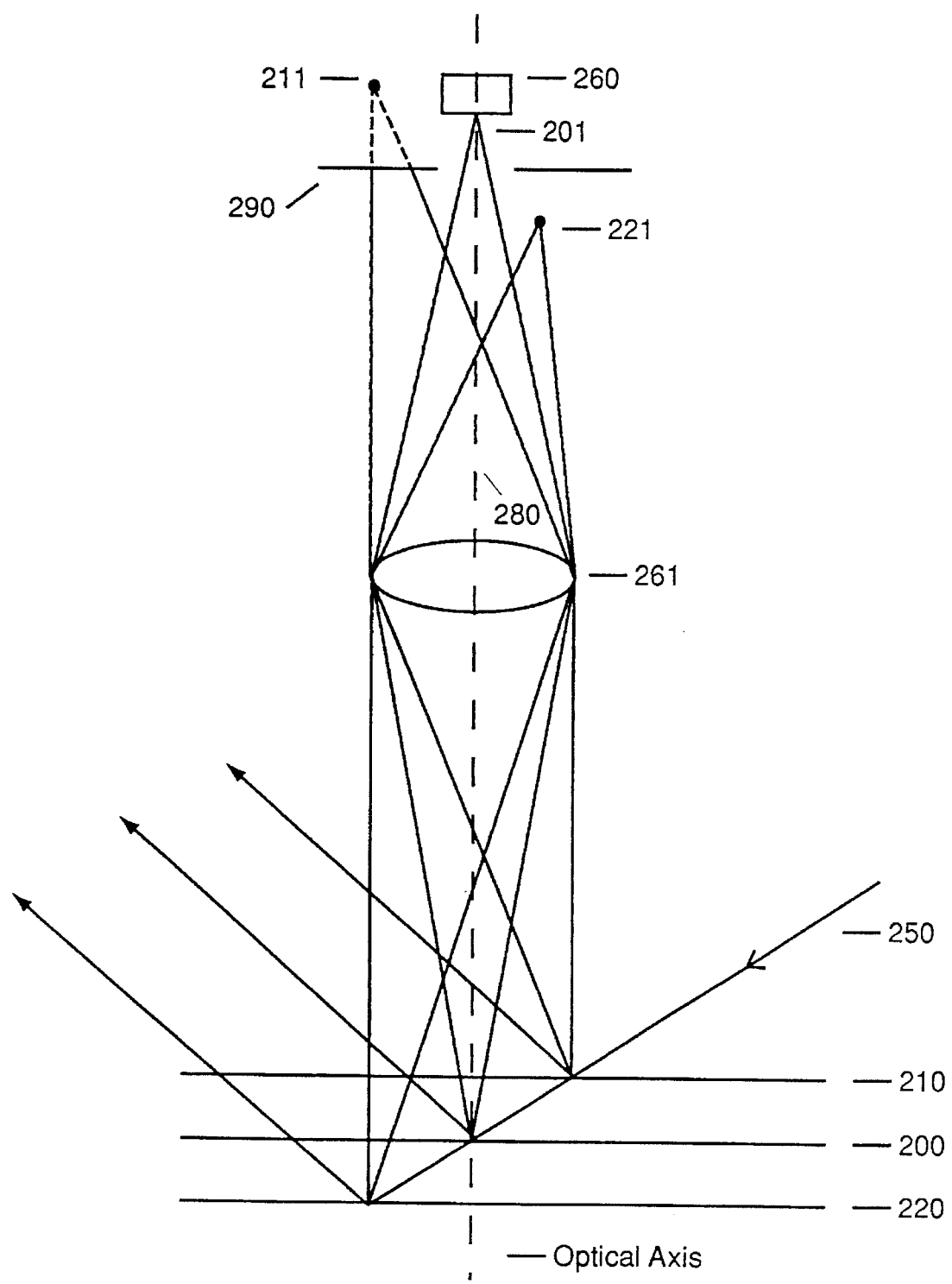
FIG. 2 illustrates how the imaging system achieves good depth discrimination.

FIG. 2 is a simplified illustration exhibiting how the imaging system achieves good depth discrimination. As shown, a focal plane 200 is located between planes 210 and 220. Planes 210 and 220 both represent planes that are out of focus. In response to the incident light 250, all 3 planes fluoresce light. This emission is transmitted through collection optics 261. However, emission originating from out-of-focus planes 210 and 220 is displaced sideways at 211 and 221, respectively, in relationship to the collection optics' optical axis 280. Since the active area of the light detectors array 260 is about 14 µm wide, nearly all of the emission from any plane that is more than slightly out-of-focus is not detected.

III. Detailed Description of One Embodiment of the Imaging System.

a. Detection Device

Figure 3:
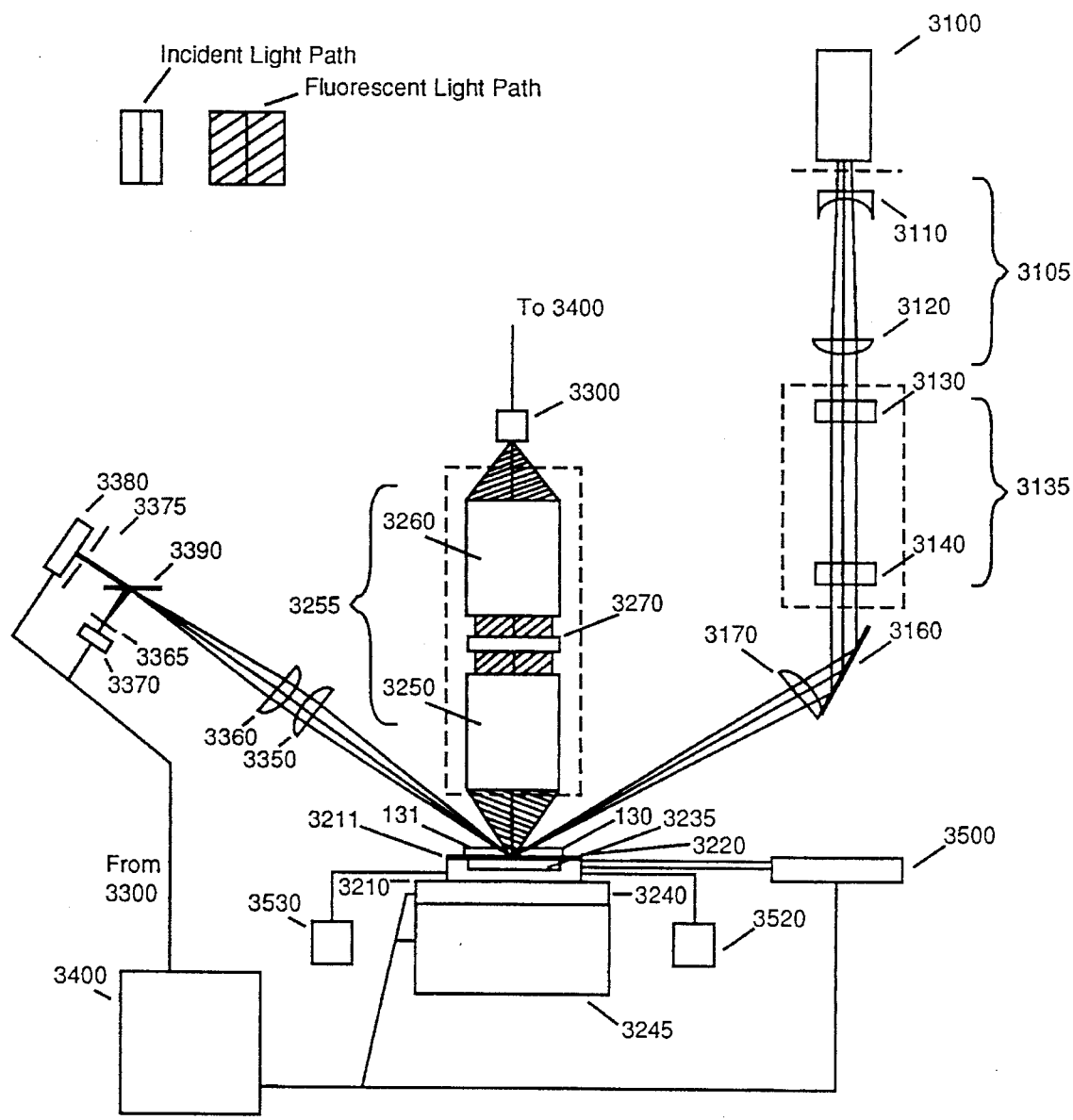
FIG. 3 shows the imaging system according to the present invention.

FIG. 3 schematically illustrates a particular system for imaging a sample. The system includes a body 3220 for holding a support 130 containing the sample on a surface 131. In some embodiments, the support may be a microscope slide or any surface which is adequate to hold the sample. The body 3220, depending on the application, may be a flow cell having a cavity 3235. Flow cells, such as those disclosed in U.S. patent application Ser. No. 08/255,682, already incorporated by reference, may also be used. The flow cell, for example, may be employed to detect reactions between targets and probes. In some embodiments, the bottom of the cavity may comprise a light absorptive material so as to minimize the scattering of incident light.

In embodiments utilizing the flow cell, surface 131 is mated to body 3220 and serves to seal cavity 3235. The flow cell and the substrate may be mated for sealing with one or more gaskets. In one embodiment, the substrate is mated to the body by vacuum pressure generated by a pump 3520. Optionally, the flow cell is provided with two concentric gaskets and the intervening space is held at a vacuum to ensure mating of the substrate to the gaskets. Alternatively, the substrate may be attached by using screws, clips, or other mounting techniques.

When mated to the flow cell, the cavity encompasses the sample. The cavity includes an inlet port 3210 and an outlet port 3211. A fluid, which in some embodiments contains fluorescently labeled targets, is introduced into the cavity through inlet port 3210. A pump 3530, which may be a model no. B-120-S made by Eldex Laboratories, circulates fluids into the cavity via inlet 3210 port and out through outlet port 3211 for recirculation or disposal. Alternatively, a syringe, gas pressure, or other fluid transfer device may be used to flow fluids into and through the cavity.

Optionally, pump 3530 may be replaced by an agitation system that agitates and circulates fluids through the cavity. Agitating the fluids shortens the incubation period between the probes and targets. This can be best explained in terms of kinetics. A thin layer, known as the depletion layer, is located above the probe sample. Since targets migrate to the surface and bind with the probe sequences, this layer is essentially devoid of targets. However, additional targets are inhibited from flowing into the depletion layer due to finite diffusion coefficients. As a result, incubation period is significantly increased. By using the agitation system to dissolve the depletion layer, additional targets are presented at the surface for binding. Ultrasonic radiation and/or heat, shaking the holder, magnetic beads, or other agitating technique may also be employed.

In some embodiments, the flow cell is provided with a temperature controller 3500 for maintaining the flow cell at a desired temperature. Since probe/target interaction is sensitive to temperature, the ability to control it within the flow cell permits hybridization to be conducted under optimal temperature. Temperature controller 3500, which is a model 13270-615 refrigerated circulating bath with a RS232 interface made by VWR Scientific, controls temperature by circulating water at a specified temperature through channels formed in the flow cell. A computer 3400, which may be any appropriately programmed digital computer, such as a Gateway 486DX operating at 33 MHz, monitors and controls the refrigerated bath via the RS232 interface. Alternatively, a refrigerated air circulating device, resistance heater, peltier device (thermoelectric cooler), or other temperature controller may be implemented.

According to one embodiment, flow cell 3220 is mounted to a x-y-z translation stage 3245. Translation stage 3245, for example, may be a Pacific Precision Laboratories Model ST-SL06R-B5M driven by stepping motors. The flow cell may be mated to the translation stage by vacuum pressure generated by pump 3520. Alternatively, screws, clips or other mounting techniques may be employed to mate the flow cell to the translation stage.

As previously mentioned, the flow cell is oriented to maintain the substrate perpendicular to the optical axis of the collection optics, which in some embodiments is substantially vertical. Maintaining the support in the plane of the incident light minimizes or eliminates image distortion and intensity variations which would otherwise occur. In some embodiments, the x-y-z translation stage may be mounted on a tilt stage 3240 to achieve the desired flow cell orientation. Alternatively, shims may be inserted to align the flow cell in a substantially vertical position. Movement of the translation stage and tilt stage may be controlled by computer 3400.

To initiate the imaging process, incident light from a light source 3100 passes through excitation optics, which in turn focus the light at the support. In one embodiment, the light source is a model 2017 argon laser manufactured by Spectra-Physics. The laser generates a beam having a wavelength of about 488 nm and a diameter of about 1.4 mm at the $1/e^2$ points. As the radial beam passes through the optical train, it is transformed into a line, for example, of about 50 mm×11 μm at the $1/e^2$ points. This line is more than sufficient to illuminate the sample, which in some embodiments is about 12.8 mm, with uniform intensity within about 10%. Thus, potential image distortions or intensity variations are minimized.

The various elements of the excitation optics underlying the transformation of the beam into the desired spatial excitation geometry will now be described. Light source 3100 directs the beam through, for example, a 3× telescope 3105 that expands and collimates the beam to about 4.2 mm in diameter. In some embodiments, the 3× telescope includes lenses 3110 and 3120, which may be a −25 mm focal length plano-concave lens and a 75 mm focal length plano-convex lens, respectively. Alternatively, the 3× telescope may comprise any combination of lenses having a focal length ratio of 1:3.

Thereafter, the beam passes through a cylindrical telescope 3135. The cylindrical telescope, for example, may have a magnification power of 12. In some embodiments, telescope 135 comprises a −12.7 mm focal length cylindrical lens 3130 and a 150 mm focal length cylindrical lens 3140. Alternatively, cylindrical telescope 3135 includes any combination of cylindrical lenses having a focal length ratio of 1:12 or a 12× anamorphic prism pair. Cylindrical telescope 3135 expands the beam vertically to about 50 mm.

In another alternative, lens 3130 of telescope 3135 may be a line-generator lens, such as an acylindrical lens with one plano surface and a hyperbolic surface. The line-generator lens converts a gaussian beam to one having uniform intensity along its length. When using a line-generator lens, the beam may be expanded to the height of the sample, which is about 13.0 mm.

Next, the light is focused onto the sample by a lens 3170. In some embodiments, lens 3170 may be a 75 mm focal length cylindrical lens that focuses the beam to a line of about 50 mm×11 μm at its focal plane. Preferably, the sample is illuminated at an external incident angle of about 45°, although other angles may be acceptable. As illustrated in FIG. 2, illuminating the sample at an angle: 1) improves the depth discrimination of the detection system; and 2) decouples the illumination and collection light paths.

Optionally, a mirror 3160 is placed between lens 3140 and lens 3170 to steer the beam appropriately. Alternatively, the mirror or mirrors may be optionally placed at other locations to provide a more compact system.

As depicted in the Figure, the incident light is reflected by the substrate through lenses 3350 and 3360. Lenses 3350 and 3360, for example, may be a 75 mm focal length cylindrical lens and a 75 mm focal length spherical lens, respectively. Lens 3350 collimates the reflected light and lens 3360 focuses the collimated beam to about an 11 µm spot through a slit 3375. In some embodiments, the vertical slit may have a width of about 25 µm. As the translation stage moves the substrate through focus, the spot moves horizontally across the vertical slit. In one embodiment, the optics are aligned to locate the spot substantially at the center of the slit when the substrate is located in the focal plane of the incident light.

A photodiode 3380 is located behind slit 3375 to detect an amount of light passing through the slit. The photodiode, which may be a 13 DSI007 made by Melles Griot, generates a voltage proportional to the amount of the detected light. The output from the photodiode aids computer 3400 in focusing the incident light at the substrate.

For embodiments employing a tilt stage 3240, a beam splitter 3390, horizontal slit 3365, and photodiode 3370 may be optionally configured to detect when the substrate is substantially parallel to the plane of the incident light. Beam splitter 3390, which in some embodiments is a 50% plate beam splitter, directs a portion of the reflected light from the substrate toward horizontal slit 3365. The horizontal slit may have a width of about 25 µm wide. As the tilt stage rotates the substrate from the vertical plane, the beam spot moves vertically across the horizontal slit. The beam splitter locates the spot substantially at the center of slit 3365 when the sample is substantially vertical.

A photodiode 3370, which may be similar to photodiode 3380, is located behind slit 3375. The output from the photodiode aids computer 3400 in positioning the substrate vertically.

In response to the illumination, the surface bound targets, which, for example, may be labeled with fluorescein, fluoresce light. The fluorescence is transmitted through a set of collection optics 3255. In some embodiments, collection optics may comprise lenses 3250 and 3260, which may be 83 mm focal lengths f/1.76 lenses manufactured by Rodenstock Precision Optics. In some embodiments, collection optics are configured at 1× magnification. In alternative embodiments, collection optics may comprise a pair of 50 mm focal length f/1.4 camera lenses, a single f/2.8 micro lens such as a Nikon 60 mm Micro-Nikkor, or any combination of lenses having a focal length ratio of 1:1.

The collection optics' magnification may be varied depending on the application. For example, the image resolution may be increased by a factor of 5 using a 5× collection optics. In one embodiment, the 5× collection optics may be a 5× microscope objective with 0.18 aperture, such as a model 80.3515 manufactured by Rolyn Optics, or any combination of lenses 3250 and 3260 having a focal length ratio of 1:5.

A filter 3270, such as a 515 nm long pass filter, may be located between lenses 3250 and 3260 to block scattered laser light.

Collection optics 3255 image the fluorescence originating from the surface of the substrate onto a CCD array 3300. In some embodiments, the CCD array may be a part of a CCD subsystem manufactured by Ocean Optics Inc. The subsystem, for example, may include a NEC linear CCD array and associated control electronics. The CCD array comprises 1024 pixels (i.e., photodiodes), each of which is about 14 µm square (total active area of about 14.4 mm×14 µm). Although a specific linear CCD array is disclosed, it will be understood that any commercially available linear CCDs having various pixel sizes and several hundred to several thousand pixels, such as those manufactured by Kodak, EG&G Reticon, and Dalsa, may be used.

The CCD subsystem communicates with and is controlled by a data acquisition board installed in computer 3400. Data acquisition board may be of the type that is well known in the art such as a CIO-DAS16/Jr manufactured by Computer Boards Inc. The data acquisition board and CCD subsystem, for example, may operate in the following manner. The data acquisition board controls the CCD integration period by sending a clock signal to the CCD subsystem. In one embodiment, the CCD subsystem sets the CCD integration period at 4096 clock periods. by changing the clock rate, the actual time in which the CCD integrates data can be manipulated.

During an integration period, each photodiode accumulates a charge proportional to the amount of light that reaches it. Upon termination of the integration period, the charges are transferred to the CCD's shift registers and a new integration period commences. The shift registers store the charges as voltages which represent the light pattern incident on the CCD array. The voltages are then transmitted at the clock rate to the data acquisition board, where they are digitized and stored in the computer's memory. In this manner, a strip of the sample is imaged during each integration period. Thereafter, a subsequent row is integrated until the sample is completely scanned.

Figure 4A:
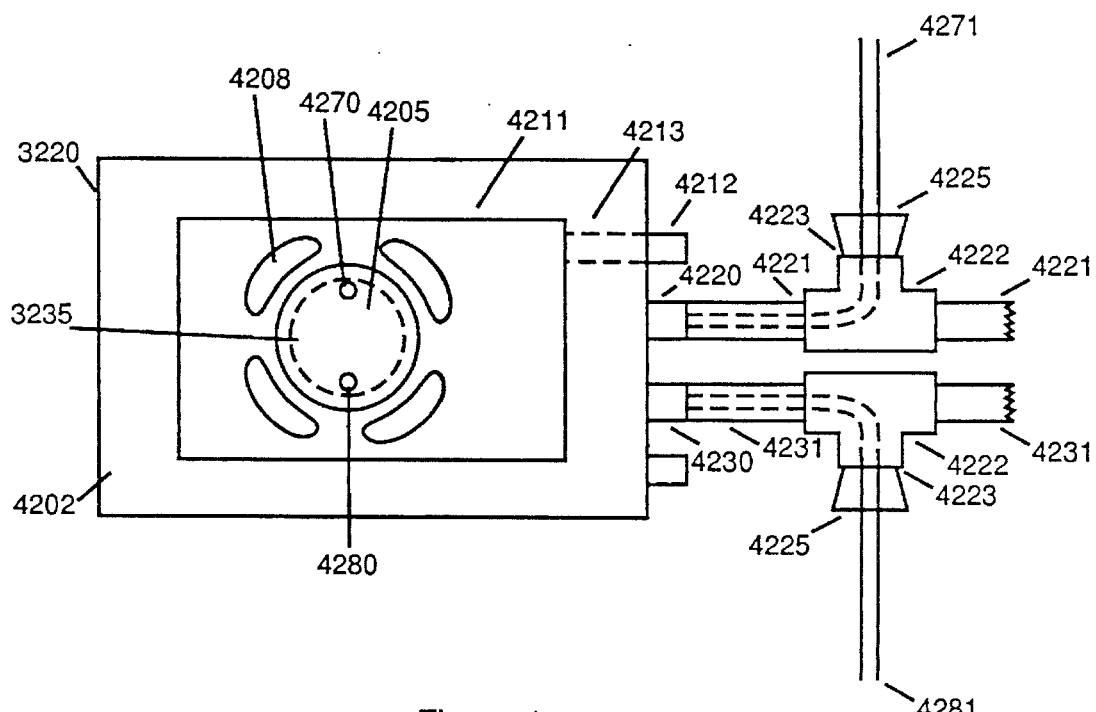
FIGS. 4a–4d show a flow cell on which a substrate is mounted.
Figure 4B:
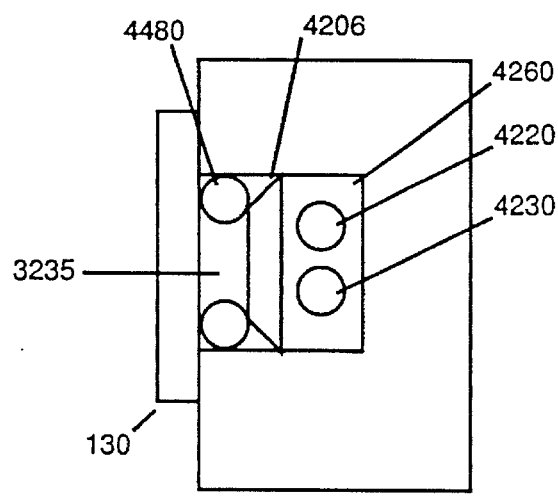
Figure 4C:
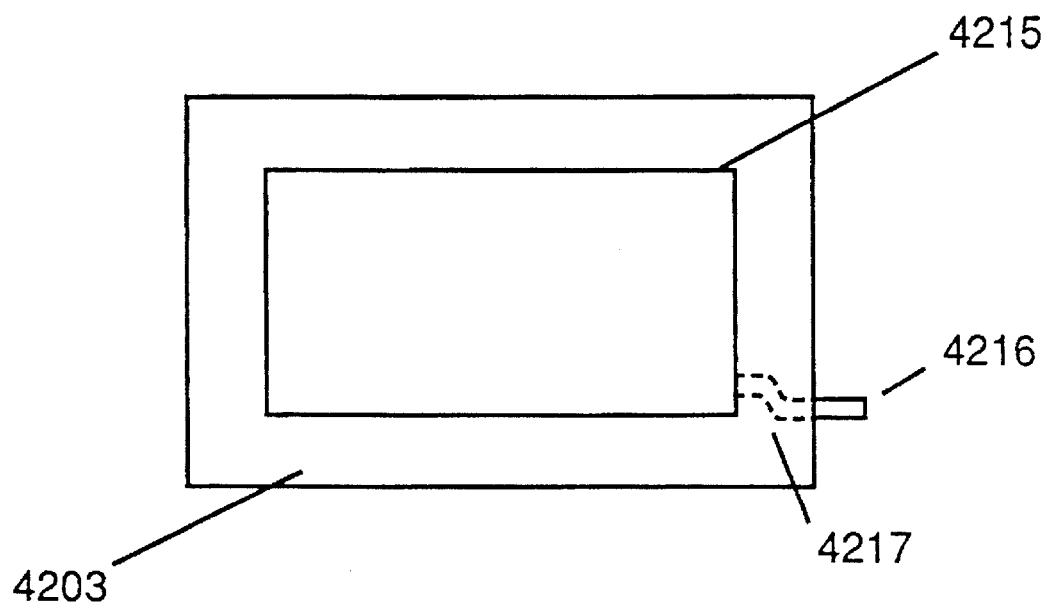

FIGS. 4a–4c illustrate flow cell 3220 in greater detail. FIG. 4a is a front view, FIG. 4b is a cross sectional view, and FIG. 4c is a back view of the cavity. Referring to FIG. 4a, flow cell 3220 includes a cavity 3235 on a surface 4202 thereon. The depth of the cavity, for example, may be between about 10 and 1500 µm, but other depths may be used. Typically, the surface area of the cavity is greater than the size of the probe sample, which may be about 13×13 mm. Inlet port 4220 and outlet port 4230 communicate with the cavity. In some embodiments, the ports may have a diameter of about 300 to 400 µm and are coupled to a refrigerated circulating bath via tubes 4221 and 4231, respectively, for controlling temperature in the cavity. The refrigerated bath circulates water at a specified temperature into and through the cavity.

A plurality of slots 4208 may be formed around the cavity to thermally isolate it from the rest of the flow cell body. Because the thermal mass of the flow cell is reduced, the temperature within the cavity is more efficiently and accurately controlled.

In some embodiments, a panel 4205 having a substantially flat surface divides the cavity into two subcavities. Panel 4205, for example, may be a light absorptive glass such as an RG1000 nm long pass filter. The high absorbance of the RG1000 glass across the visible spectrum (surface emissivity of RG1000 is not detectable at any wavelengths below 700 nm) substantially suppresses any background luminescence that may be excited by the incident wavelength. The polished flat surface of the light-absorbing glass also reduces scattering of incident light, lessening the burden of filtering stray light at the incident wavelength. The glass also provides a durable medium for subdividing the cavity since it is relatively immune to corrosion in the high salt environment common in DNA hybridization experiments or other chemical reactions.

Panel 4205 may be mounted to the flow cell by a plurality of screws, clips, RTV silicone cement, or other adhesives. Referring to FIG. 4b, subcavity 4260, which contains inlet port 4220 and outlet port 4230, is sealed by panel 4205. Accordingly, water from the refrigerated bath is isolated from cavity 3235. This design provides separate cavities for conducting chemical reaction and controlling temperature. Since the cavity for controlling temperature is directly below the reaction cavity, the temperature parameter of the reaction is controlled more effectively.

Substrate 130 is mated to surface 4202 and seals cavity 3235. Preferably, the probe array on the substrate is contained in cavity 3235 when the substrate is mated to the flow cell. In some embodiments, an O-ring 4480 or other sealing material may be provided to improve mating between the substrate and flow cell. Optionally, edge 4206 of panel 4205 is beveled to allow for the use of a larger seal cross section to improve mating without increasing the volume of the cavity. In some instances, it is desirable to maintain the cavity volume as small as possible so as to control reaction parameters, such as temperature or concentration of chemicals more accurately. In additional, waste may be reduced since smaller volume requires smaller amount of material to perform the experiment.

Referring back to FIG. 4a, a groove 4211 is optionally formed on surface 4202. The groove, for example, may be about 2 mm deep and 2 mm wide. In one embodiment, groove 4211 is covered by the substrate when it is mounted on surface 4202. The groove communicates with channel 4213 and vacuum fitting 4212 which is connected to a vacuum pump. The vacuum pump creates a vacuum in the groove that causes the substrate to adhere to surface 4202. Optionally, one or more gaskets may be provided to improve the sealing between the flow cell and substrate.

Figure 4D:
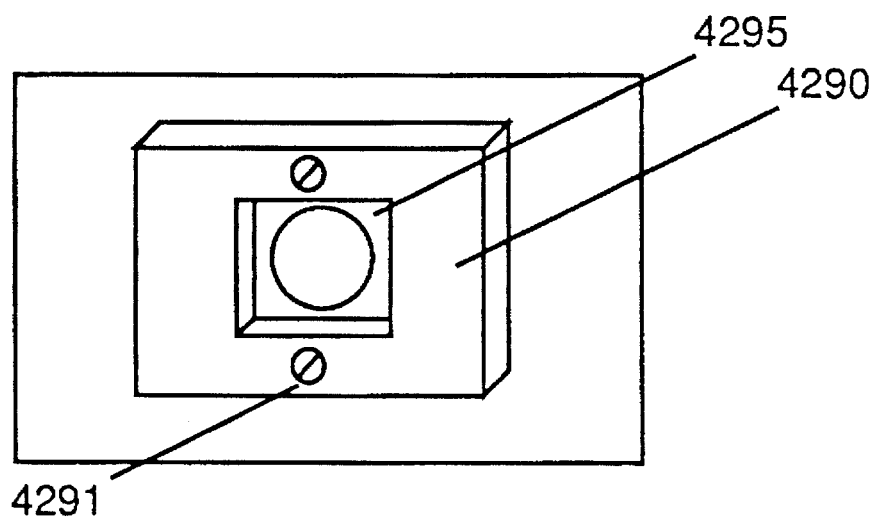

FIG. 4d illustrates an alternative technique for mating the substrate to the flow cell. When mounted to the flow cell, a panel 4290 exerts a force that is sufficient to immobilize substrate 130 located therebetween. Panel 4290, for example, may be mounted by a plurality of screws 4291, clips, clamps, pins, or other mounting devices. In some embodiments, panel 4290 includes an opening 4295 for exposing the sample to the incident light. Opening 4295 may optionally be covered with a glass or other substantially transparent or translucent materials. Alternatively, panel 4290 may be composed of a substantially transparent or translucent material.

In reference to FIG. 4a, panel 4205 includes ports 4270 and 4280 that communicate with subcavity 3235. A tube 4271 is connected to port 4270 and a tube 4281 is connected to port 4280. Tubes 4271 and 4281 are inserted through tubes 4221 and 4231, respectively, by connectors 4222. Connectors 4222, for example, may be T-connectors, each having a seal 4225 located at opening 4223. Seal 4225 prevents the water from the refrigerated bath from leaking out through the connector. It will be understood that other configurations, such as providing additional ports similar to ports 4220 and 4230, may be employed.

Tubes 4271 and 4281 allow selected fluids to be introduced into or circulated through the cavity. In some embodiments, tubes 4271 and 4281 may be connected to a pump for circulating fluids through the cavity. In one embodiment, tubes 4271 and 4281 are connected to an agitation system that agitates and circulates fluids through the cavity.

Referring to FIG. 4c, a groove 4215 is optionally formed on the surface 4203 of the flow cell. The dimensions of groove, for example, may be about 2 mm deep and 2 mm wide. According to one embodiment, surface 4203 is mated to the translation stage. Groove 4211 is covered by the translation stage when the flow cell is mated thereto. Groove 4215 communicates with channel 4217 and vacuum fitting 4216 which is connected to a vacuum pump. The pump creates a vacuum in groove 4215 and causes the surface 4203 to adhere to the translation stage. Optionally, additional grooves may be formed to increase the mating force. Alternatively, the flow cell may be mounted on the translation stage by screws, clips, pins, various types of adhesives, or other fastening techniques.

Figure 5:
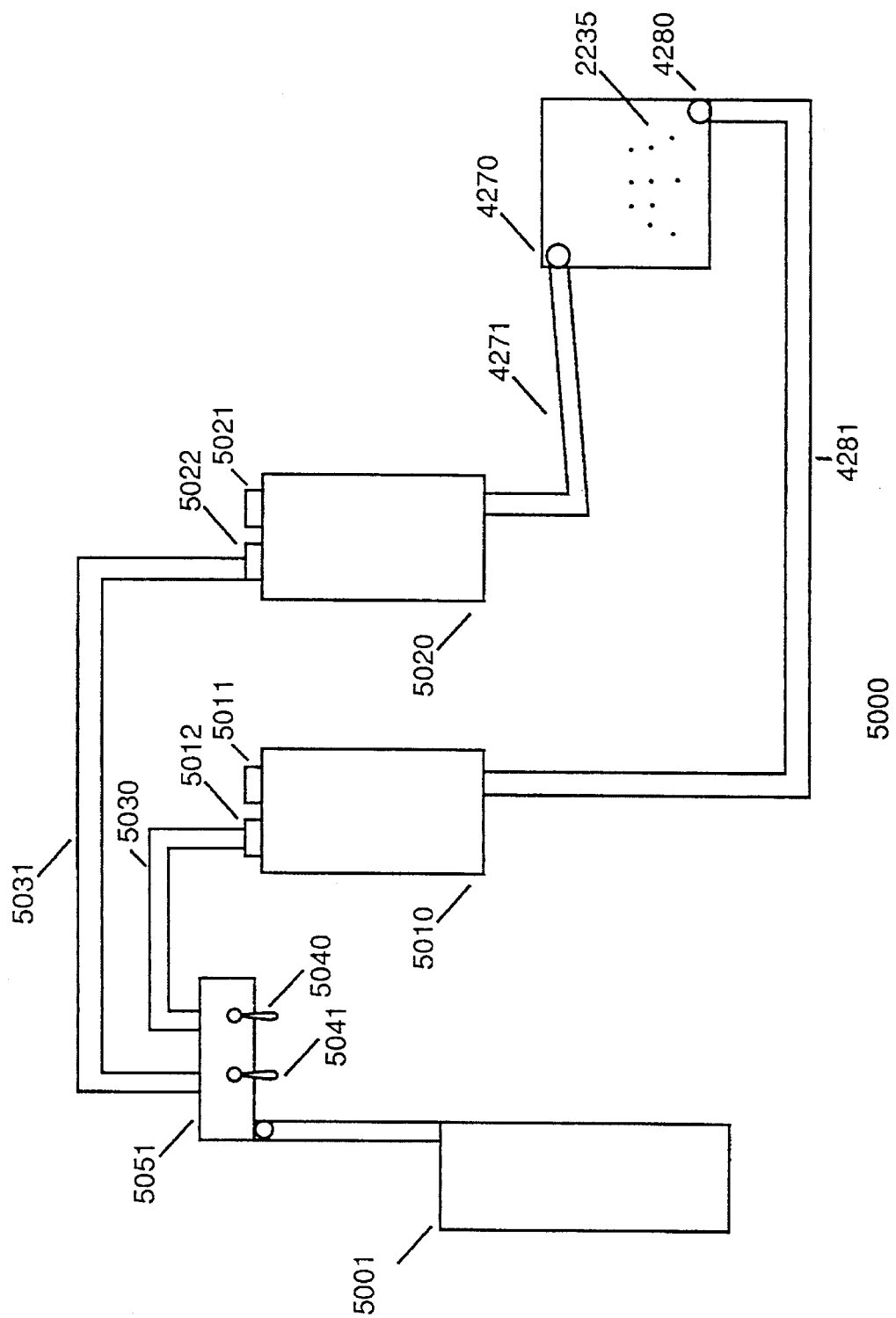
FIG. 5 shows a agitation system.

FIG. 5 illustrates an agitation system in detail. As shown, the agitation system 5000 includes two liquid containers 5010 and 5020, which in the some embodiments are about 10 milliliters each. According to one embodiment, the containers may be centrifuge tubes. Container 5010 communicates with port 4280 via tube 4281 and container 5020 communicates with port 4270 via tube 4271. An inlet port 5012 and a vent port 5011 are located at or near the top of container 5010. Container 5020 also includes an inlet port 5022 and a vent 5021 at or near its top. Port 5012 of container 5010 and port 5022 of container 5020 are both connected to a valve assembly 5051 via valves 5040 and 5041. An agitator 5001, which may be a nitrogen gas ($N_2$) or other gas, is connected to valve assembly 5051. Valves 5040 and 5041 regulate the flow of $N_2$ into their respective containers. In some embodiments, additional containers (not shown) may be provided, similar to container 5010, for introducing a buffer and/or other fluid into the cavity.

In operation, a fluid is placed into container 5010. The fluid, for example, may contain targets that are to be hybridized with probes on the chip. Container 5010 is sealed by closing port 5011 while container 5020 is vented by opening port 5021. Next, $N_2$ is injected into container 5010, forcing the fluid through tube 5050, cavity 2235, and finally into container 5020. The bubbles formed by the $N_2$ agitate the fluid as it circulates through the system. When the amount of fluid in container 5010 nears empty, the system reverses the flow of the fluid by closing valve 5040 and port 5021 and opening valve 5041 and port 5011. This cycle is repeated until the reaction between the probes and targets is completed.

The system described in FIG. 5 may be operated in an alternative manner. According to this technique, back pressure formed in the second container is used to reverse the flow of the solution. In operation, the fluid is placed in container 5010 and both ports 5011 and 5021 are closed. As $N_2$ is injected into container 5010, the fluid is forced through tube 5050, cavity 2235, and finally into container 5020. Because the vent port in container 5020 is closed, the pressure therein begins to build as the volume of fluid and $N_2$ increases. When the amount of fluid in container 5010 nears empty, the flow of $N_2$ into container 5010 is terminated by closing valve 5040. Next, the circulatory system is vented by opening port 5011 of container 5010. As a result, the pressure in container 5020 forces the solution back through the system toward container 5010. In one embodiment, the system is injected with $N_2$ for about 3 seconds and vented for about 3 seconds. This cycle is repeated until hybridization between the probes and targets is completed.

b. Data acquisition

Figure 6:
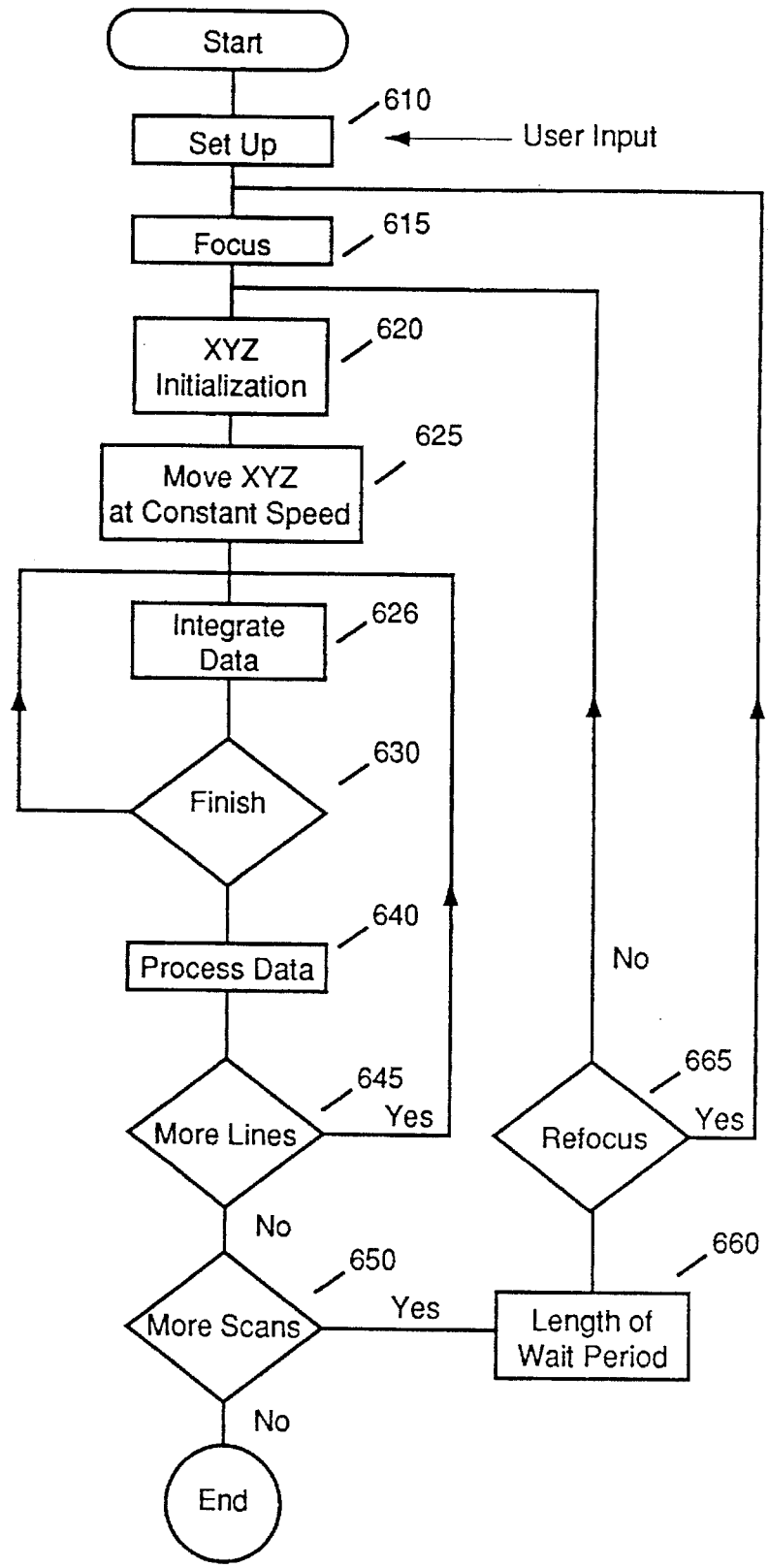
FIG. 6 is a flow chart illustrating the general operation of the imaging system.
Figure 7A:
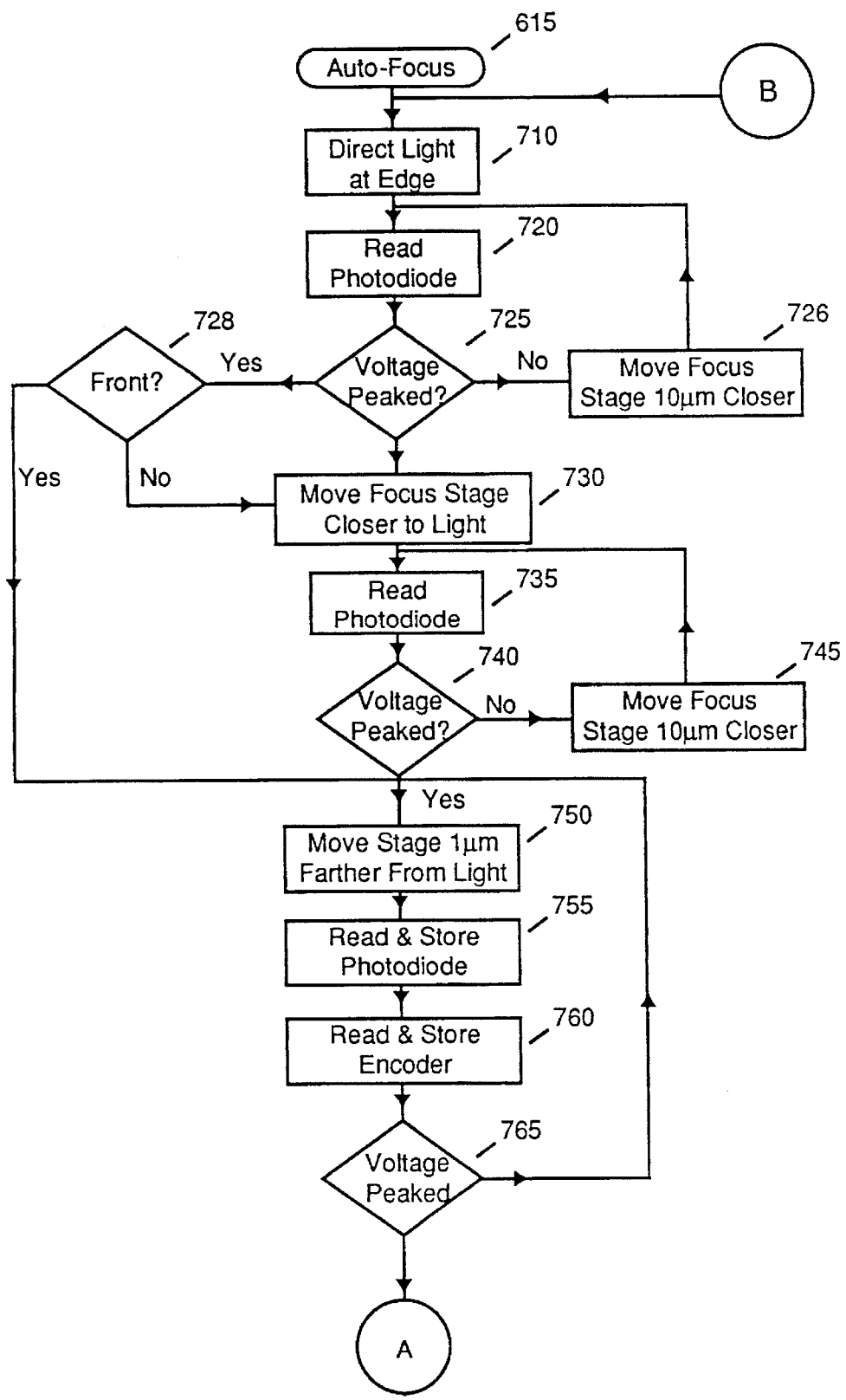
FIGS. 7a–7b are flow charts illustrating the steps for focusing the light at the sample.
Figure 7B:
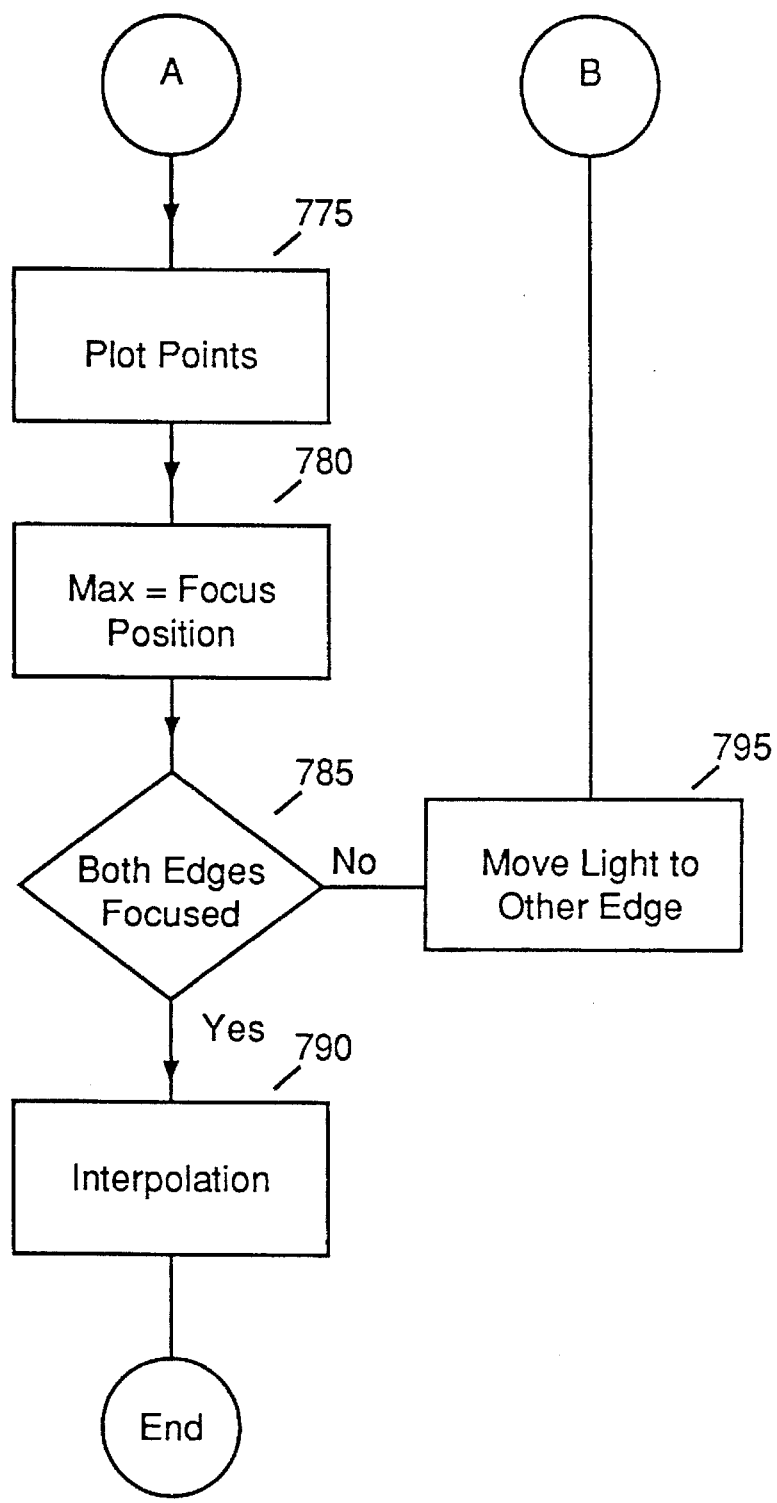
Figure 8:
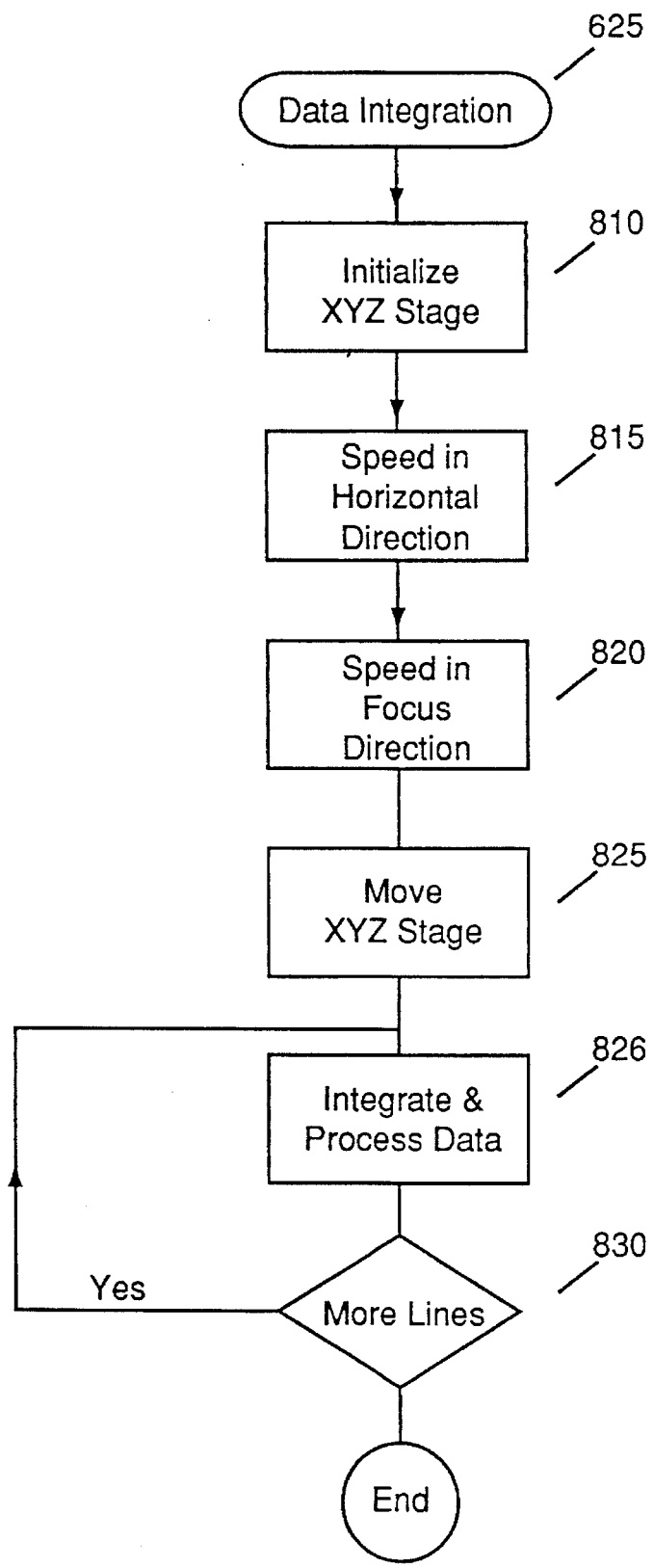
FIG. 8 is a flow chart illustrating in greater detail the steps for acquiring data.

FIGS. 6–8 are flow charts describing one embodiment. FIG. 6 is an overall description of the system's operation. A source code listing representative of the software for operating the system is set forth in Appendix I.

At step 610, the system is initialized and prompts the user for test parameters such as:

a) pixel size;

b) scan speed;

e) scan temperature or temperatures;

c) number of scans to be performed;

d) time between scans;

f) thickness of substrate;

g) surface on which to focus;

h) whether or not to refocus after each scan; and i) data file name.

The pixel size parameter dictates the size of the data points or pixels that compose the image. Generally, the pixel size is inversely related to the image resolution (i.e., the degree of discernable detail). For example, if a higher resolution is desired, the user would choose a smaller pixel size. On the other hand, if the higher resolution is not required, a larger pixel may be chosen. In one embodiment, the user may choose a pixel size that is a multiple of the size of the pixels in the CCD array, which is 14 µm (i.e., 14, 28, 42, 56, etc.).

The scan-speed parameter sets the clock rate in the data acquisition board for controlling CCD array's integration period. The higher the clock speed, the shorter the integration time. Typically, the clock rate is set at 111 KHz. This results in an integration period of 36.9 msec (4096 clock periods per integration period).

The temperature parameter controls the temperature at which the scan is performed. Temperature may vary depending on the materials being tested. The number-of-scans parameter corresponds to the number of times the user wishes to scan the substrate. The time-between-scans parameter controls the amount of time to wait before commencing a subsequent scan. These parameters may vary according to the application. For example, in a kinetics experiment (analyzing the sample as it approaches equilibrium), the user may configure the system to continuously scan the sample until it reaches equilibrium. Additionally, each scan may be performed at a different temperature.

The thickness-of-substrate parameter, which is used by system's auto-focus routine, is equal to the approximate thickness of the substrate that is being imaged. In some embodiments, the user optionally chooses the surface onto which the excitation light is to be focused (i.e., the front or back surface of the substrate). For example, the front surface is chosen when the system does not employ a flow cell. The user may also choose to refocus the sample before beginning a subsequent scan. Other parameters may include specifying the name of the file in which the acquired data are stored.

At step 615, the system focuses the laser at the substrate. At step 620, the system initializes the x-y-z table at its start position. In some embodiments, this position corresponds to the edge of the sample at which the excitation line commences scanning. At step 625, the system begins to translate the horizontal stage at a constant speed toward the opposite edge. At step 626, the CCD begins to integrate data. At step 630, the system evaluates if the CCD integration period is completed, upon which the system digitizes and processes the data at step 640. At step 645, the system determines if data from all regions or lines have been collected. The system repeats the loop beginning at 626 until the sample has been completely scanned. At step 650, the system determines if there are any more scans to perform, as determined by the set up parameters. If there are, the system calculates the amount of time to wait before commencing the next scan at step 660. At step 665, the system evaluates whether to repeat the process from step 615 (if refocusing is desired) or 620 (if refocusing is not desired). Otherwise, the scan is terminated.

FIGS. 7a–7b illustrate focusing step 615 in greater detail. Auto-focusing is accomplished by the system in either two or three phases, depending upon which surface (front or back) the light is to be focused on. In the first phase, the system focuses the laser roughly on the back surface of the substrate. At step 710, the system directs light at one edge of the sample. The substrate reflects the light toward focusing optics which directs it through vertical slit and at a photo-diode. As the substrate is translated through focus, the light moves horizontally across the vertical slit. In response to the light, the photo-diode generates a voltage proportional to the amount of light detected. Since the optics are aligned to locate the light in the middle of the slit when the substrate is in focus, the focus position will generally produce the maximum voltage.

At step 720, the system reads the voltage, and at step 725, compares it with the previous voltage value read. If the voltage has not peaked (i.e., present value less then previous value), the system moves the flow cell closer toward the incident light at step 726. The distance over which the flow cell is moved, for example, may be about 10 µm. Next, the loop beginning at step 720 is repeated until the voltage generated by the photodiode has peaked, at which time, the light is focused roughly on the back surface. Because the flow cell is moved in 10 µm steps, the focal plane of the light is slightly beyond the front surface (i.e., inside the substrate).

At step 728, the system determines at which surface to focus the light (defined by the user at step 610 of FIG. 6). If the front surface is chosen, the system proceeds to step 750 (the third focusing phase), which will be described later. If the back surface is chosen, the system proceeds to step 730 (the second focusing phase).

At step 730, the system moves the flow cell closer toward the incident light. In some embodiments, the distance over which the flow cell is moved is about equal to half the thickness of the substrate. This distance is determined from the value entered by the user at step 610 of FIG. 6. Generally, the distance is equal to about 350 mm, which is about ½ the thickness of a typical substrate.

At step 735, the system reads the voltage generated by the photodiode, similarly as in step 720. At step 740, the system determines whether or not the value has peaked. If it has not, the system moves the flow cell closer toward the incident light at step 745. As in step 726, the distance over which the flow cell is translated may be about 10 µm. The loop commencing at step 735 is repeated until the voltage generated by the photodiode has peaked, at which time, the laser is roughly focused at a point beyond the front surface.

Next, the system starts the third or fine focusing phase, which focuses the light at the desired surface. At step 750, the system moves the flow cell farther from the incident light, for example, in steps of about 1 µm. The computer reads and stores the voltage generated by the photodiode at step 755. At step 760, the encoder indicating the position of the focus stage is read and the resulting data is stored. This value identifies the location of the focus stage to within about 1 µm. At step 765, the system determines if the present voltage value is greater then the previous value, in which case, the loop at step 750 is repeated. According to some embodiments, the process beginning at 750 is repeated, for example, until the photodiode voltage is less than the peak voltage minus twice the typical peak-to-peak photodiode voltage noise. At step 775, the data points are fitted into a parabola, where x = encoder position and y = voltage corresponding to the position. At step 780, the system determines the focus position of the desired surface, which corresponds to the maximum of the parabola. By moving the flow cell beyond the position at which the maximum voltage is generated and fitting the values to a parabola, effects of false or misleading values caused by the presence of noise are minimized. Therefore, this focusing technique generates greater accuracy than the method which merely takes the position corresponding to the peak voltage.

At step 785, the system ascertains whether the opposite edge of the substrate has been focused, in which case the process proceeds to step 790. Otherwise, the system moves the x-y-z translation stage in order to direct the light at the opposite edge at step 795. Thereafter, the process beginning at step 710 is repeated to focus second edge.

At step 790, the system determines the focus position of the other substrate position through linear interpolation using, for example, an equation having the following form: a+bx. Alternatively, a more complex mathematical model may be used to more closely approximate the substrate's surface, such as a+bx+cy+dxy.

By using the focusing method disclosed herein, the laser may be focused on the front surface of the substrate, which is significantly less reflective than the back surface. Generally, it is difficult to focus on a weakly reflective surface in the vicinity of a strongly reflective surface. However, this problem is solved by the present invention.

For embodiments employing a tilt stage, the focusing process can be modified to focus the substrate vertically. The process is divided into two phases similar to the first and third focusing phase of FIGS. 7a–7b.

In the first phase, the tilt stage is initialized at an off-vertical position and rotated, for example, in increments of about 0.1 milliradians (mrad) toward vertical. After each increment, the voltage from photodiode (located behind the horizontal slit) is read and the process continues until the voltage has peaked. At this point, the tilt stage is slightly past vertical.

In the second phase, the tilt stage is rotated back toward vertical, for example, in increments of about 0.01 mrad. After each rotation, the voltage and corresponding tilt stage position are read and stored in memory. These steps may be repeated until the voltage is less than the peak voltage minus twice the typical peak-to-peak photodiode voltage noise. Thereafter, the data are fitted to a parabola, wherein the maximum represents the position at which the substrate surface is vertical.

FIG. 8 illustrates the data acquisition process beginning at step 625 in greater detail. In a specific embodiment, data are collected by scanning the sample one vertical line at a time until the sample is completely scanned. Alternatively, data may be acquired by other techniques such as scanning the substrate in horizontal lines.

At step 810, the x-y-z translation stage is initialized at its starting position. At step 815, the system calculates the constant velocity of the horizontal stage, which is equal to the pixel size divided by the integration period. Typically the velocity is about 0.3 mm/sec.

At step 820, the system calculates the constant speed at which the focusing stage is to be moved in order to maintain the substrate surface in focus. This speed is derived from the data obtained during the focusing phase. For example, the speed may be equal to:

$$(F1-F2)/(P*N)$$

where F1= the focus position for the first edge; F2 is the focus position of the second edge; P= the integration period; and N= the number of lines per scan.

At step 825, the system starts moving the translation stage in the horizontal direction at a constant velocity (i.e., stage continues to move until the entire two-dimensional image is acquired). At 826, the data acquisition board sends clock pulses to the CCD subsystem, commencing the CCD integration period. At step 830, the system determines if the CCD integration period is completed. After each integration period, the CCD subsystem generates an analog signal for each pixel that is proportional to the amount of light sensed thereon. The CCD subsystem transmits the analog signals to the data acquisition board and begins a new integration period.

As the CCD subsystem integrates data for the next scan line, the data acquisition board digitizes the analog signals and stores the data in memory. Thereafter, the system processes the raw data. In some embodiments, data processing may include subtracting a line of dark data, which represents the outputs of the CCD array in darkness, from the raw data. This compensates for the fact that the CCD output voltages may be non-zero even in total darkness and can be slightly different for each pixel. The line of dark data may be acquired previously and stored in the computer's memory. Additionally, if the specified pixel size is greater than 14 µm, the data are binned. For example, if the specified pixel size is 28 microns, the system bins the data 2 fold, i.e., the 1024 data points are converted to 512 data points, each of which represents the sum of the data from 2 adjacent pixels.

After the line of data is processed, it is displayed as a gray scale image. In one embodiment, the gray scale contains 16 gray levels. Alternatively, other gray scale levels or color scales may be used. Preferably, the middle of the scale corresponds to the average amount of emission detected during the scan.

At step 830, the system determines if there are any more lines left to scan. The loop beginning at step 826 is repeated until the sample has been completely scanned.

Figure 9:
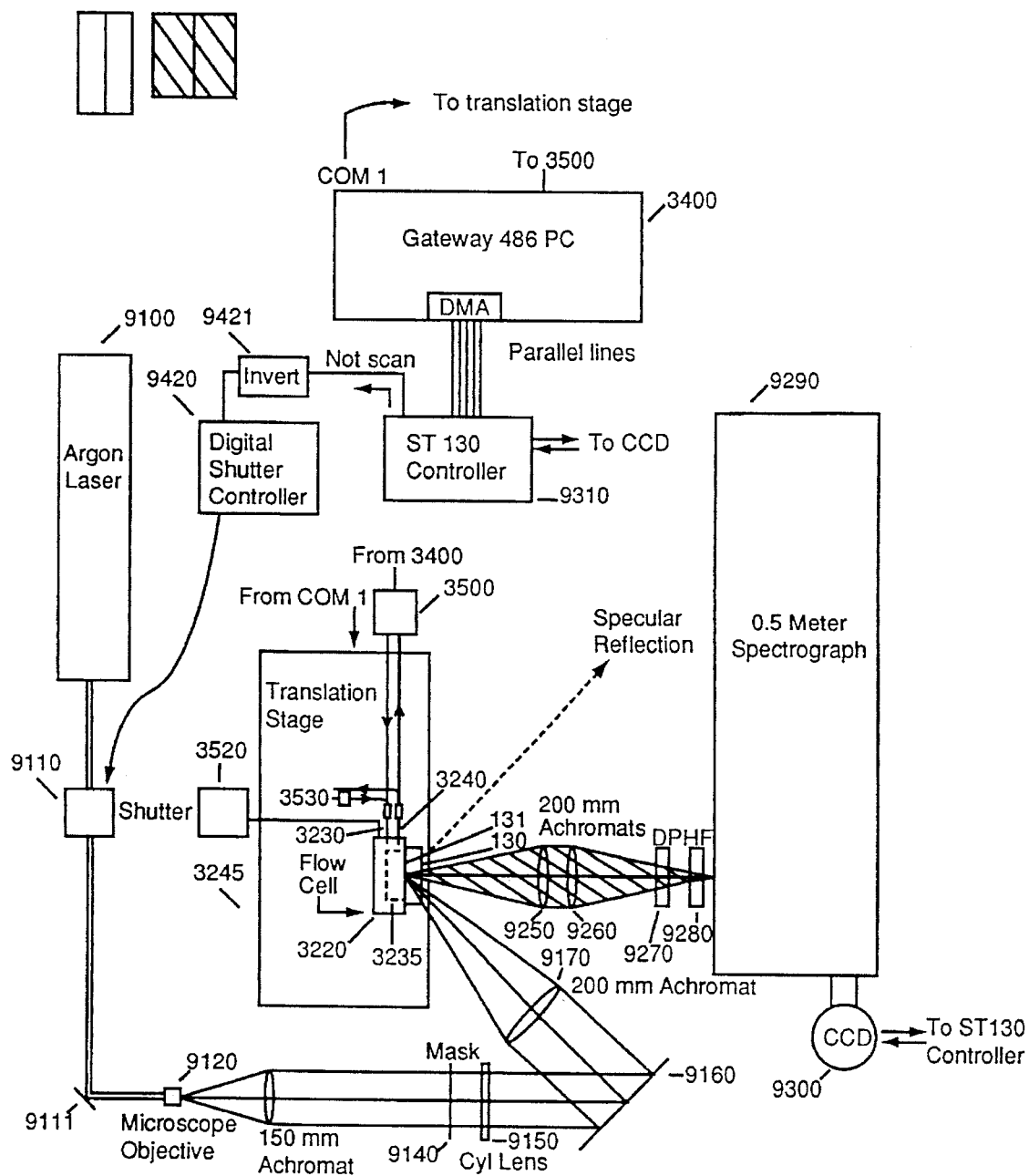
FIG. 9 shows an alternative embodiment of the imaging system.

IV. Detailed Description of an Alternative Embodiment of the Imaging System a. Detection Device FIG. 9 schematically illustrates an alternative embodiment of an imaging system. As depicted, system 9000 comprises components which are common to the system described in FIG. 3. The common components, for example, include the body 3220, fluid pump, vacuum pump, agitation system, temperature controller, and others which will become apparent. Such components will be given the same figure numbers and will not be discussed in detail to avoid redundancy.

System 9000 includes a body 3220 on which a support 130 containing a sample to be imaged is mounted. Depending on the application, the body may be a flow cell as described in FIGS. 4a–4c. The support may be mated to the body by vacuum pressure generated by a pump 3520 or by other mating technique. When attached to the body, the support and body seals the cavity except for an inlet port 3230 and an outlet port 3240. Fluids containing, for example, fluorescently labeled targets (fluorescein) are introduced into cavity through inlet port 3230 to hybridize with the sample. A pump 3530 or any of the other fluid transfer techniques described herein may be employed to flow fluids into the cavity and out through outlet port 3240.

In some embodiments, an agitation system is employed to shorten the incubation period between the probes and targets by breaking up the surface depletion layer above the sample. A temperature controller 3500 may also be connected to the flow cell to enable imaging at the optimal thermal conditions. Computer 3400, which may be any appropriately programmed digital computer such as a Gateway 486DX operating at 33 MHz, operates the temperature controller.

Flow cell 3220 may be mounted on a three-axis (x-y-z) translation table 3245. In some embodiments, the flow cell is mounted to the translation table by vacuum pressure generated by pump 3250. To maintain the top and bottom of the probe sample in the focal plane of the incident light, the flow cell is mounted in a substantially vertical position. This orientation may be achieved by any of the methods described previously.

Movement of the translation table is controlled by a motion controller, which in some embodiments is a single axis motion controller from Pacific Precision Laboratories (PPL). In alternative embodiments, a multi-axis motion controller may be used to auto-focus the line of light on the substrate or to enable other data collection schemes. The motion controller communicates and accepts commands from computer 3400.

In operation, light from an excitation source scans the substrate to obtain an image of the sample. Excitation source 9100 may be a model 2065 argon laser manufactured by Spectra-Physics that generates about a 3.0 mm diameter beam. The beam is directed through excitation optics that transform the beam to a line of about is about 15 mm×50 μm. This excitation geometry enables simultaneous imaging of a row of the sample rather than on a point-by-point basis.

The excitation optics will now be described in detail. From the laser, the 3 mm excitation beam is directed through a microscope objective 9120. For the sake of compactness, a mirror 9111, such as a 2" diameter Newport BD1, may be employed to reflect the incident beam to microscope objective 9120. Microscope objective 120, which has a magnification power of 10, expands the beam to about 30 mm. The beam then passes through a lens 9130. The lens, which may be a 150 mm achromat, collimates the beam.

Typically, the radial intensity of the expanded collimated beam has a Gaussian profile. As previously discussed, scanning the support with a non-uniform beam is undesirable because the edges of the line illuminated probe sample may appear dim. To minimize this problem, a mask 9140 is inserted after lens 9130 for masking the beam top and bottom, thereby passing only the central portion of the beam. In one embodiment, the mask passes a horizontal band that is about 7.5 mm.

Thereafter, the beam passes through a cylindrical lens 150 having a horizontal cylinder axis, which may be a 100 mm f.l. made by Melles Griot. Cylindrical lens 9150 expands the beam spot vertically. Alternatively, a hyperbolic lens may be used to expand the beam vertically while resulting in a flattened radial intensity distribution.

From the cylindrical lens, the light passes through a lens 9170. Optionally, a planar mirror may be inserted after the cylindrical lens to reflect the excitation light toward lens 9170. To achieve the desired beam height of about 15 mm, the ratio of the focal lengths of the cylindrical lens and lens 9170 is approximately 1:2, thus magnifying the beam to about 15 mm. Lens 9170, which in some embodiments is a 80 mm achromat, focuses the light to a line of about 15 mm×50 μm at the sample.

In a preferred embodiment, the excitation light irradiates the sample at an angle. This design decouples the illumination and collection light paths and improves the depth discrimination of the system. Alternatively, a confocal system may be provided by rotating the illuminating path about the collection optic axis to form a ring of illuminating rays (ring illumination).

The excitation light causes the labeled targets to fluoresce. The fluorescence is collected by collection optics. The collection optics may include lenses 9250 and 9260, which, for example, may be 200 mm achromats located nearly back to back at 1× magnification. This arrangement minimizes vignetting and allows the lenses to operate at the intended infinite conjugate ratio.

Collection optics direct the fluorescence through a monochromatic depolarizer 9270, which in some embodiments is a model 28115 manufactured by Oriel. Depolarizer 9270 eliminates the effect of the wavelength-dependent polarization bias of the diffraction grating on the observed spectral intensities. Optionally, a filter 9280, which in some embodiments is a long-pass absorptive filter, may be placed after depolarizer 9270 to prevent any light at the incident wavelength from being detected. Alternatively, a holographic line rejection filter, dichroic mirror, or other filter may be employed.

The fluorescence then passes through the entrance slit of a spectrograph 9290, which produces an emission spectrum. According to one embodiment, the spectrograph is a 0.5 Czerny-Turner fitted with toroidal mirrors to eliminate astigmatism and field curvature. Various diffraction gratings, such a 150/mm ruled grating, and 300/mm and 600/mm holographic gratings are provided with the spectrograph.

Figure 10:
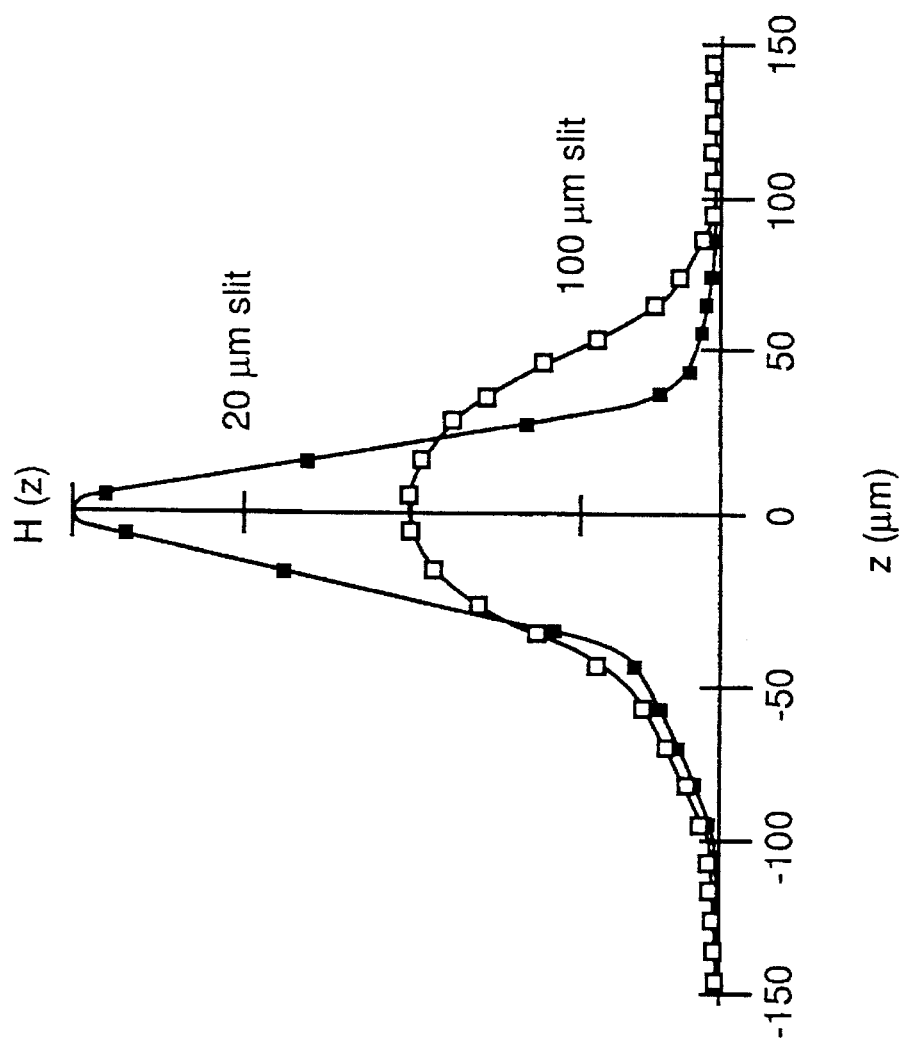
FIG. 10 shows the axial response of the imaging system of FIG. 9.

The spectrograph's entrance slit is adjustable from 0 to 2 mm in increments of 10 microns. By manipulating the width of the entrance slit, the depth of focus or axial response may be varied. FIG. 10 illustrates the axial response of the line scanner as a function of slit width. As shown, a focus depth of about 50 microns is achieved with a slitwidth of 8 microns. In alternative embodiments, transmission gratings or prisms are employed instead of a spectrograph to obtain a spectral image.

Referring back to FIG. 9, the spectrograph images the emission spectrum onto a spectrometric detector 9300, which may be a liquid cooled CCD array detector manufactured by Princeton Instruments. Such CCD array comprises a 512×512 array of 25 μm pixels (active area of 12.8 mm×12.8 mm) and utilizes a back-illuminated chip from Tektronix, thermostatted at −80° C. with 0.01° C. accuracy. Alternatively, a thermoelectrically cooled CCD or other light detector having a rectangular format may be used.

In some embodiments, CCD detector 9300 is coupled to and controlled by a controller 9310 such as a ST 130 manufactured by Princeton Instruments. Controller 9310 interfaces with computer 3400 though a direct memory access (DMA) card which may be manufactured by Princeton Instruments.

A commercially available software package, such as the CSMA software from Princeton Instruments, may be employed to perform data acquisition functions. The CSMA software controls external devices via the serial and/or parallel ports of a computer or through parallel DATA OUT lines from controller 9310. The CSMA software enables control of various data acquisition schemes to be performed, such as the speed in which an image is acquired. The CCD detector integrates data when the shutter therein is opened. Thus, by regulating the amount of time the shutter remains open, the user can manipulate the image acquisition speed.

The image's spatial and spectral resolution may also be specified by the data acquisition software. Depending on the application, the binning format of the CCD detector may be programmed accordingly. For example, maximum spectral and spatial resolution may be achieved by not binning the CCD detector. This would provide spatial resolution of 25 microns and spectral resolution of about 0.4 nm when using the lowest dispersion (150 lines/mm) diffraction grating in the spectrograph (full spectral bandpass of 80 nm at 150 lines/mm grating). Typically, the CCD is binned 2-fold (256 channels) in the spatial direction and 8-fold (64 channels) in the spectral direction, which results in a spatial resolution of 50 μm and spectral resolution of 3 nm.

If targets are labeled with fluorophores, continuous illumination of substrate may cause unnecessary photo-bleaching. To minimize photobleaching, a shutter 9110, which is controlled by a digital shutter controller 9420, is located between the light source and the directing optics. Shutter 9110 operates in synchrony with the shutter inside the CCD housing. This may be achieved by using an inverter circuit 9421 to invert the NOTSCAN signal from controller 9310 and coupling it to controller 9420. Of course, a timing circuit may be employed to provide signals to effect synchronous operation of both shutters. In other embodiments, photobleaching of the fluorophores may be avoided by pulsing the light source on in synchrony with the shutter in the CCD camera.

Optionally, auto-focusing and/or maintaining the sample in the plane of the excitation light may be implemented in the same fashion as the system described in FIG. 3.

b. Data Acquisition

Figure 11A:
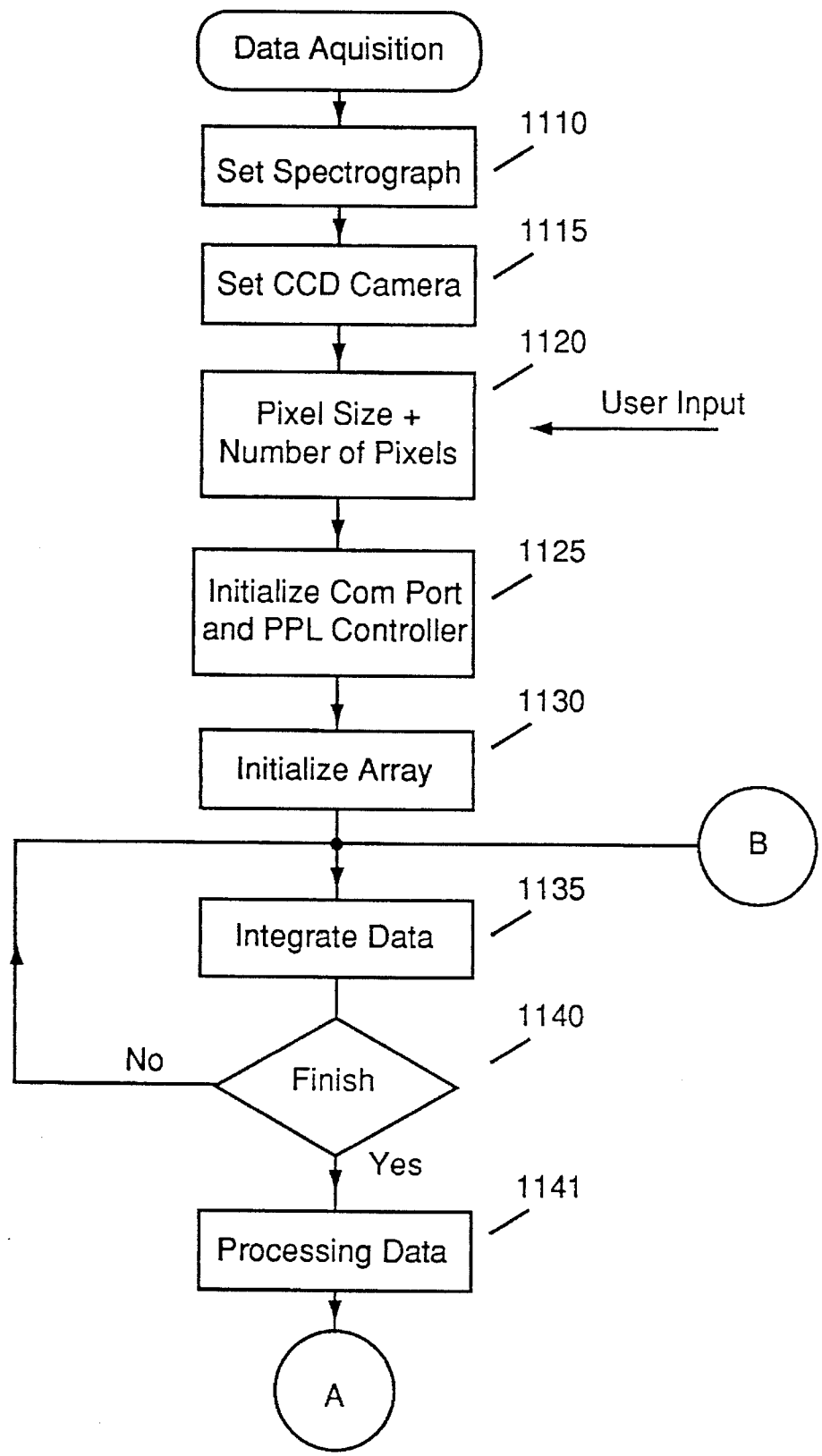
FIGS. 11a–11b are flow charts illustrating the general operations of the imaging system according to FIG. 9.
Figure 11B:
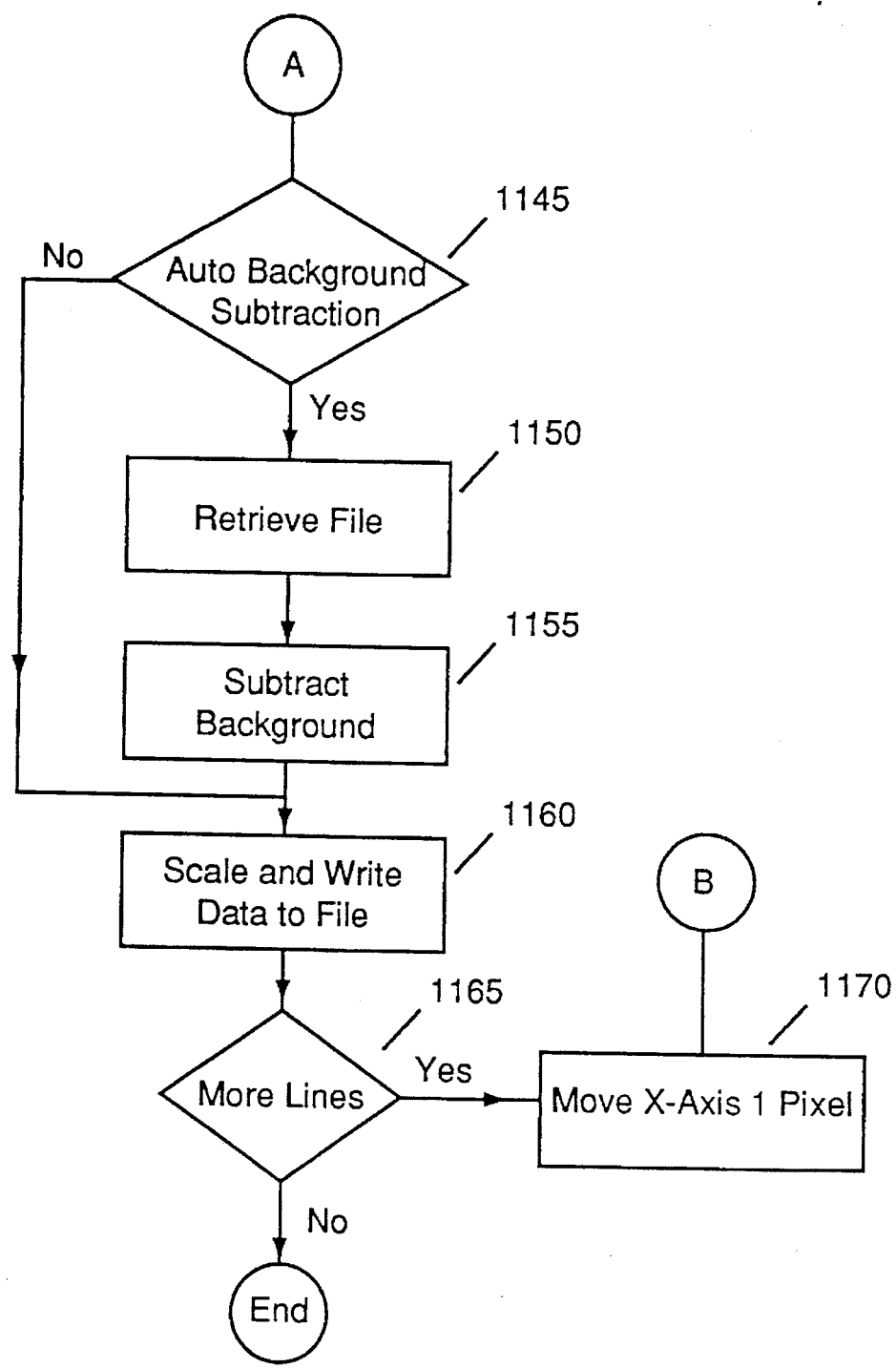

FIGS. 11a–11b are flow charts illustrating the steps for obtaining a full spectrally resolved image. A source code listing representative of the data acquisition software is set forth in Appendix II.

At step 1110, the user configures the spectrograph for data acquisition such as, but not limited to, defining the slit width of the entrance slit, the diffraction grating, and center wavelength of scan. For example the spectrograph may be configured with the following parameters: 150/mm grating, 100 μm slitwidth, and between 570 to 600 nm center wavelength.

At step 1115, the user, through the CSMA data acquisition software and controller 310, formats the CCD detector. This includes:

a) number of x channels;

b) number of y channels;

c) CCD integration time; and d) auto-background subtraction mode.

The number of x and y channels define the spectral and spatial resolution of the image respectively. Typically, the CCD is binned at 256 channels in the spatial direction and 64 in the spectral direction. Using this configuration, the 12.8 mm×50 μm vertical strip from the sample is transformed into a series of 64 monochromatic images, each representing an 12.8 mm×50 μm image as if viewed through a narrow bandpass filter of about 3 nm at a specified center wavelength.

The CCD integration time parameter corresponds to the length of time the CCD acquires data. Typically, the integration period is set between 0.1 to 1.0 seconds. The auto-background subtraction mode parameter dictates whether a background image is subtracted from the acquired data before they are stored in memory. If auto-background image is set, the system obtains a background image by detecting the sample without illumination. The background image is then written to a data file.

Subtracting the background image may be preferable because the CCD arrays used are inherently imperfect, i.e., each pixel in the CCD array generally does not have identical operational characteristics. For example, dark current and ADC offset causes the CCD output to be non-zero even in total darkness. Moreover, such output may vary systematically from pixel to pixel. By subtracting the background image, these differences are minimized.

At step 1120, the user inputs parameters for controlling the translation stage, such as the number of steps and size of each step in which the translation stage is moved during the scanning process. For example, the user defines the horizontal (or x) dimension of each pixel in the image through the step size parameter. The pixel size in the x-direction is approximately equal to the width of the sample divided by the number of spatial channels in the y-direction. As an example, if the CCD is binned at 256 spatial channels and the sample is about 12.8 mm×12.8 mm, then a pixel size of 50 μm should be chosen (12.8 mm/256=50 μm).

At step 1125, the system initializes both the serial communication port of ST130 controller and PPL motion controller. At step 1130, the system defines an array in which the collected data are stored.

At step 1135, the system commences data acquisition by opening both shutter and the CCD shutter. As the light illuminates the sample, the fluorophores emit fluorescence which is imaged onto the CCD detector. The CCD detector will generate a charge that is proportional to the amount of emission detected thereon. At step 1140, the system determines if the CCD integration period is completed (defined at step 1115). The CCD continues to collect emission at step 1135 until the integration period is completed, at which time, both shutters are closed.

At step 1141, the system processes the raw data, Typically, this involves amplification and digitization of the analog signals, which are stored charges. In some embodiments, analog signals are converted to 256 intensity levels, with the middle intensity corresponding to the middle of analog voltages that have been detected.

At step 1145, the system determines if auto-background subtraction mode has been set (defined at step 1115). If auto background subtraction mode is chosen, the system retrieves the file containing the background image at step 1150 and subtracts the background image from the raw data at step 1155. The resulting data are then written to memory at step 1160. On the other hand, if auto-background subtraction mode is not chosen, the system proceeds to step 1160 and stores the data in memory.

At step 1165, the system determines if there are any more lines of data to acquire. If so, the horizontal stage is translated in preparation for scanning the next line at step 1170. The distance over which the horizontal stage is moved is equal to about one pixel width (defined at step 1120). Thereafter, the system repeats the loop beginning 1135 until the entire area of the sample surface has been scanned.

c. Postprocessing of the Monochromatic Image Set

As mentioned above, the spectral line scanner is indispensable to the development of detection schemes such as those which simultaneously utilize multiple labels. A basic issue in any such scheme is how to handle the spectral overlap between the labels. For example, if we examine the fluorophores that are commercially available, we find that any set that may be excited by the argon laser wavelengths will indeed have substantial overlap of the emission spectra. The quantification of the surface coverages of these dyes clearly requires that images acquired at the various observation wavelengths be deconvoluted from one another.

The process of multi-fluorophore image deconvolution is formalized as follows. The emission intensity $I(\lambda_i)$ (photons cm$^{-2}$ s$^{-1}$ nm$^{-1}$) originating from a given region on the surface of the sample at an observation wavelength $\lambda_i$ is defined by:

$$I(\lambda_i) = I_o \Sigma \sigma_{ij} \rho_j$$

The variable $I_o$ is the incident intensity (photons cm$^{-2}$ s$^{-1}$), $\rho_j$ is the surface density (cm$^{-2}$) of the $j^{th}$ fluorophore species, and $\sigma_{ij}$ is the differential emission cross section (cm$^2$ nm$^{-1}$)

of the $j^{th}$ fluorophore at the $i^{th}$ detection wavelength. The system of equations describing the observation of n fluorophore species at n observation wavelengths may be expressed in matrix form as:

$$I = I_o \underline{\sigma} \rho$$

Therefore, the surface density vector ρ (the set of surface densities in molecules/cm² for the fluorescent species of interest) at each point on the image can be determined by using the inverse of the emission cross section matrix:

$$\rho = (1/I_o)\underline{\sigma}^{-1} I$$

Figure 12A:
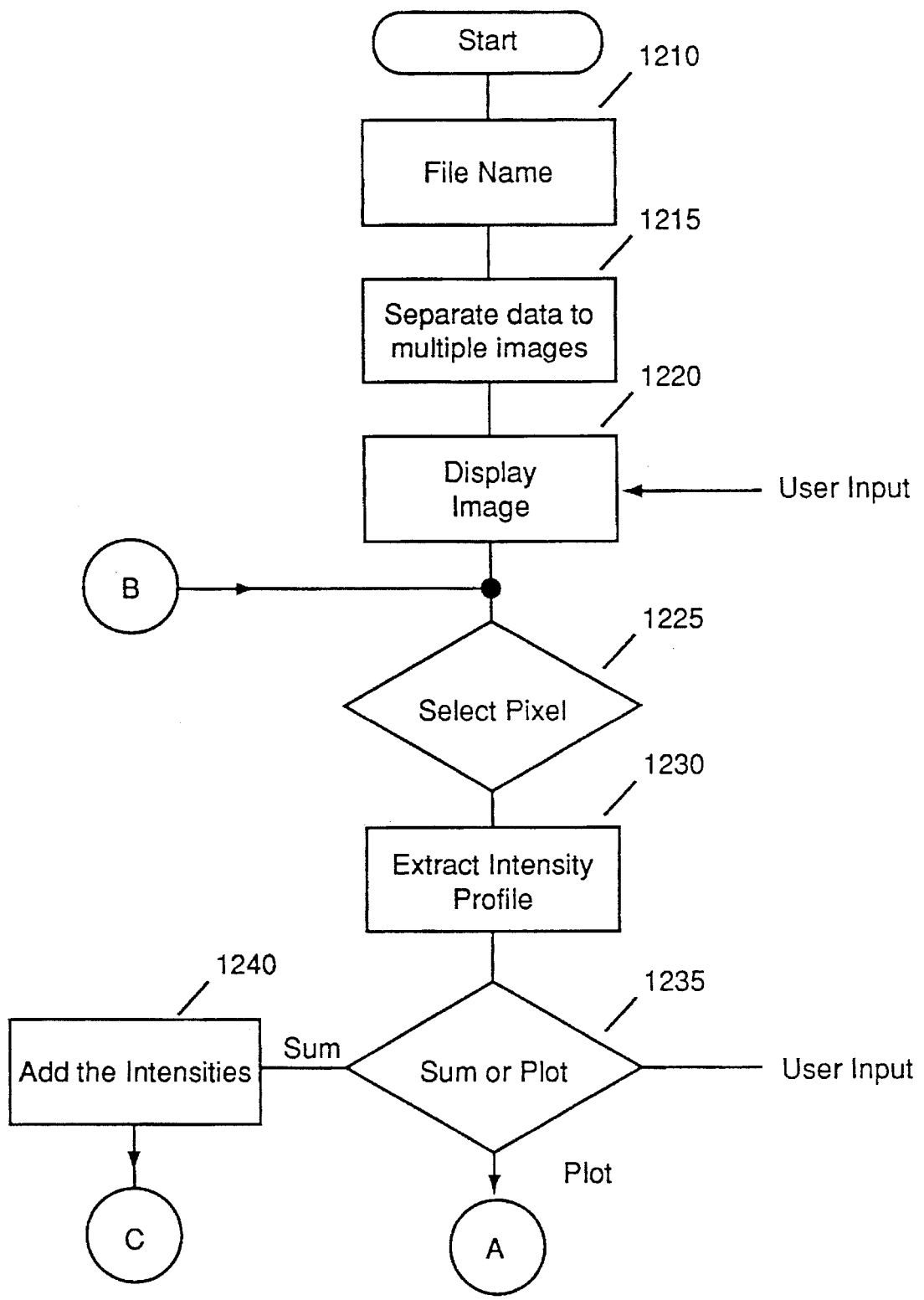
FIGS. 12a–12b are flow charts illustrating the steps for plotting the emission spectra of the acquired image.
Figure 12B:
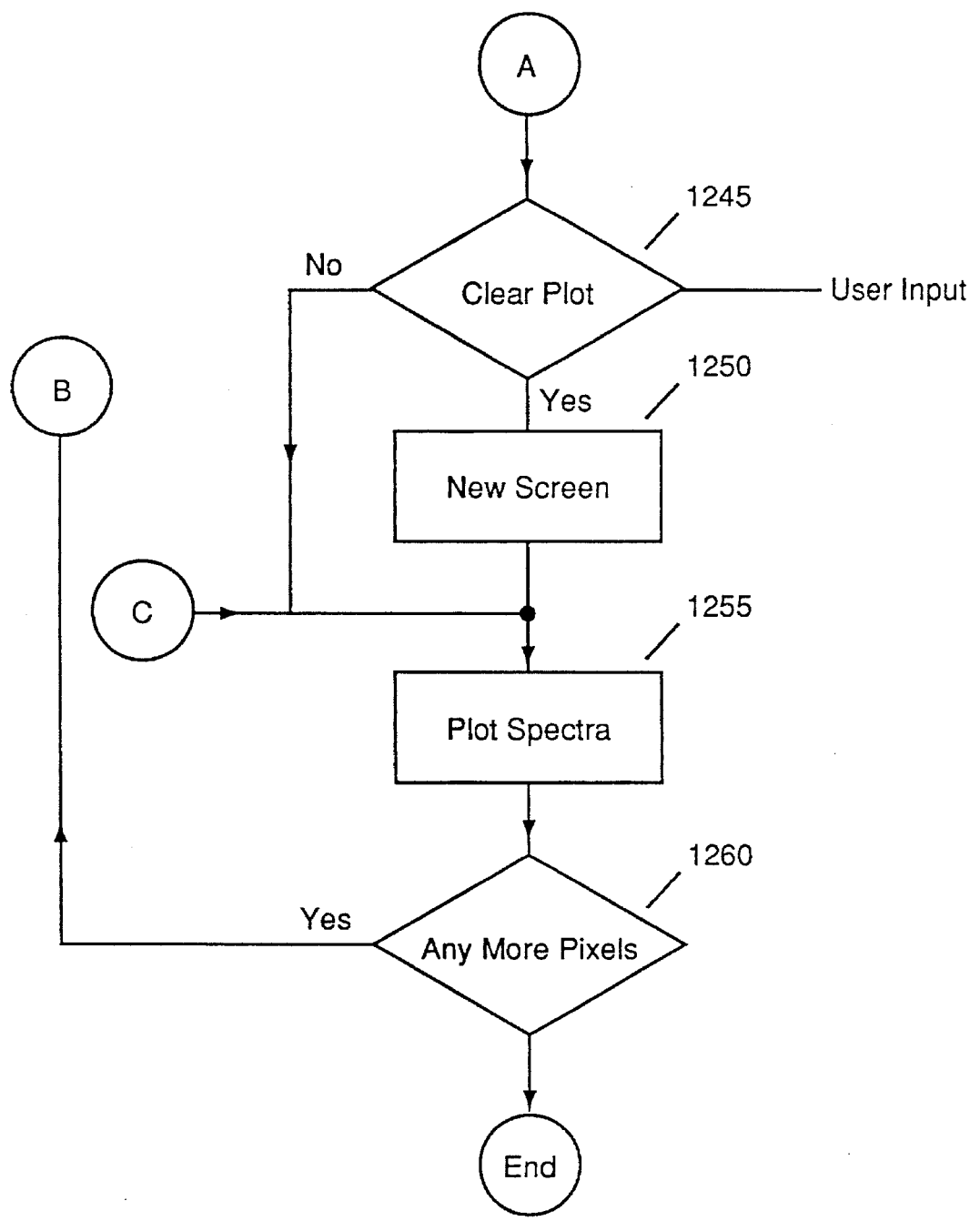

FIGS. 12a–12b are flow charts for deriving the relative cross section matrix element. In particular, the process includes plotting the fluorescent emission spectrum from any region of the image that is obtained from the steps described in FIGS. 11a–11b. A source code listing representative of the software for plotting the emission spectra is set forth in Appendix III.

Figure 12C:
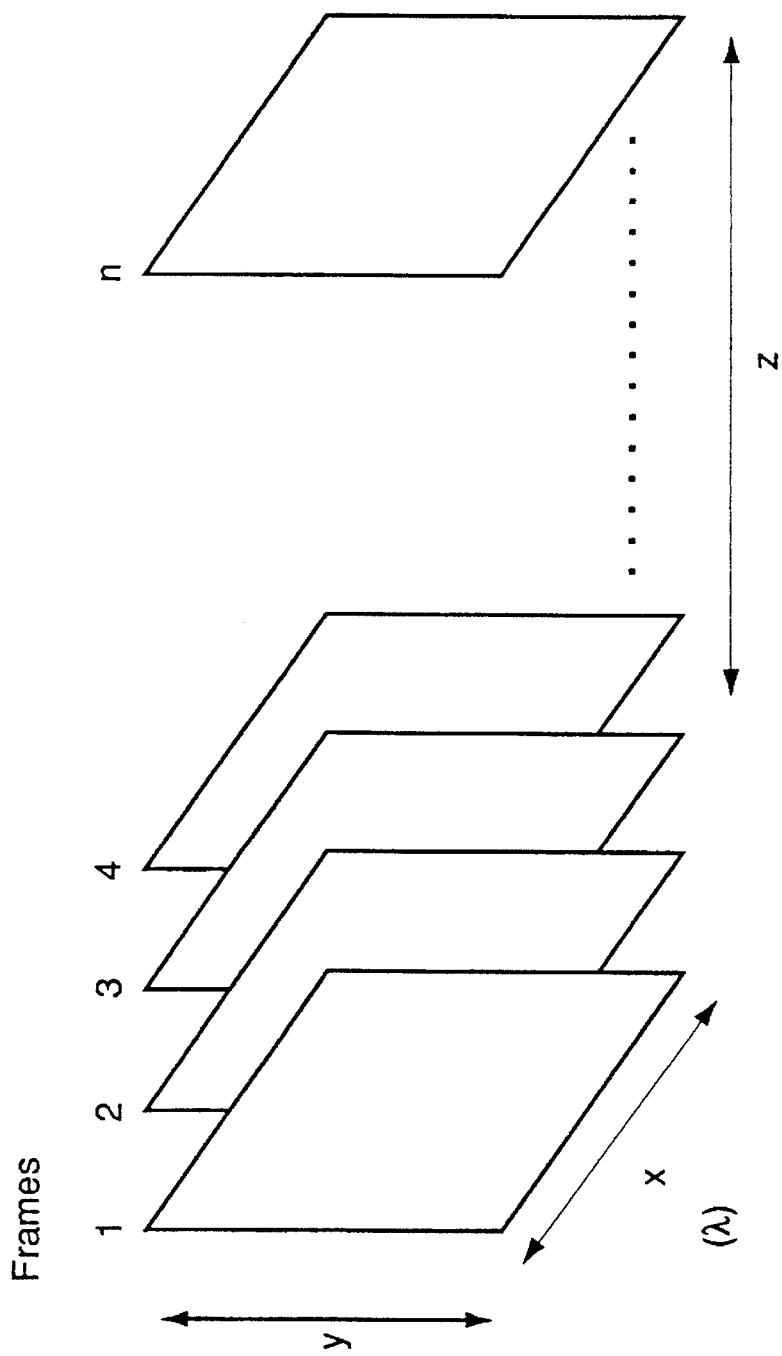
FIG. 12c shows the data structure of the data file according to the imaging system in FIG. 9.

At step 1210, the system prompts the user to input the name of the data file of interest. The system then retrieves the specified data file. The data may be stored as a series of frames which, when combined, forms a three-dimensional image. As shown in FIG. 12c, each frame represents a specific strip (12.8 mm× pixel width) of the sample at various wavelengths. The x-axis corresponds to the spectrum; the y-axis corresponds to the vertical dimension of the sample; and the z-axis represents the horizontal dimension of the sample. By rearranging the x and z indices, so-called monochromatic images of the sample at specified observation wavelengths are obtained. Further, the number of images is determined by the number of spectral channels at which the CCD is binned. At step 1215, the system reads the data file and separates the data into multiple 2-dimensional images, each representing an image of the sample at a specified observation wavelength.

At step 1220, the system displays an image of the sample at a specified observation wavelength, each spatial location varying in intensity proportional to the fluorescent intensity sensed therein. At step 1225, the user selects a pixel or group of pixels from which a plot of the emission spectrum is desired. At step 1230, the system creates the emission spectrum of the selected pixel by extracting the intensity values of the selected regions from each image. Thereafter, the user may either plot the spectrum or sum the values of the present spectrum to the previous spectrum at step 1235.

If the sum option is chosen, the system adds the spectra together at step 1240 and proceeds to step 1245. On the other hand, if the plot option is chosen, the system proceeds to step 1245 where the user may choose to clear the plot (clear screen). Depending on the user's input, the system either clears the screen at step 1250 before plotting the spectrum at step 1255 or superimposes the spectrum onto an existing plot at step 1255. At step 1260, the system prompts the user to either end the session or select another pixel to plot. If the user chooses another pixel to plot, the loop at step 1225 is repeated.

Figure 13:
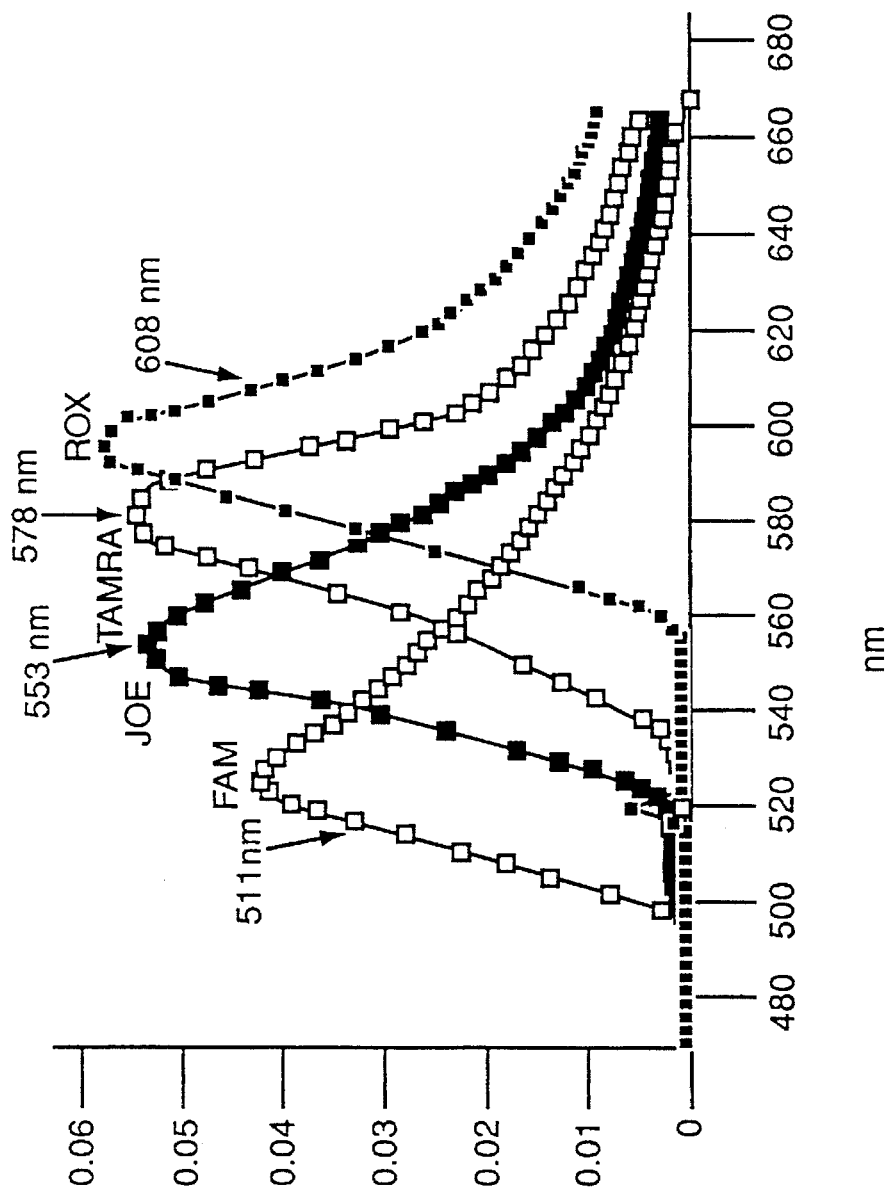
FIG. 13 shows the normalized emission spectra of four fluorophores whose emission spectra are shown in FIG. 17, and scaled according to the steps set forth in FIG. 12 a after they have been normalized.

FIG. 13 illustrates the emission spectra of four fluorophores (FAM, JOE, TAMRA, and ROX) arbitrarily normalized to unit area. The scaling of the spectral intensities obtained from the procedure according to the steps set forth in FIG. 12 are proportional to the product of the fluorophore surface density and the excitation efficiency at the chosen excitation wavelength (here either 488 nm or 514.5 nm). The excitation efficiencies per unit surface density or "unit brightness" of the fluorophores have been determined by arbitrarily scaling the emission spectra to unit area. Consequently, the fluorophore densities obtained therefrom will reflect the arbitrary scaling.

For a four fluorophore system, the values of the emission spectra of each dye at four chosen observation wavelengths form a 4×4 emission cross section matrix which can be inverted to form the matrix that multiplies four chosen monochromatic images to obtain four "fluor surface density images".

Figure 14:
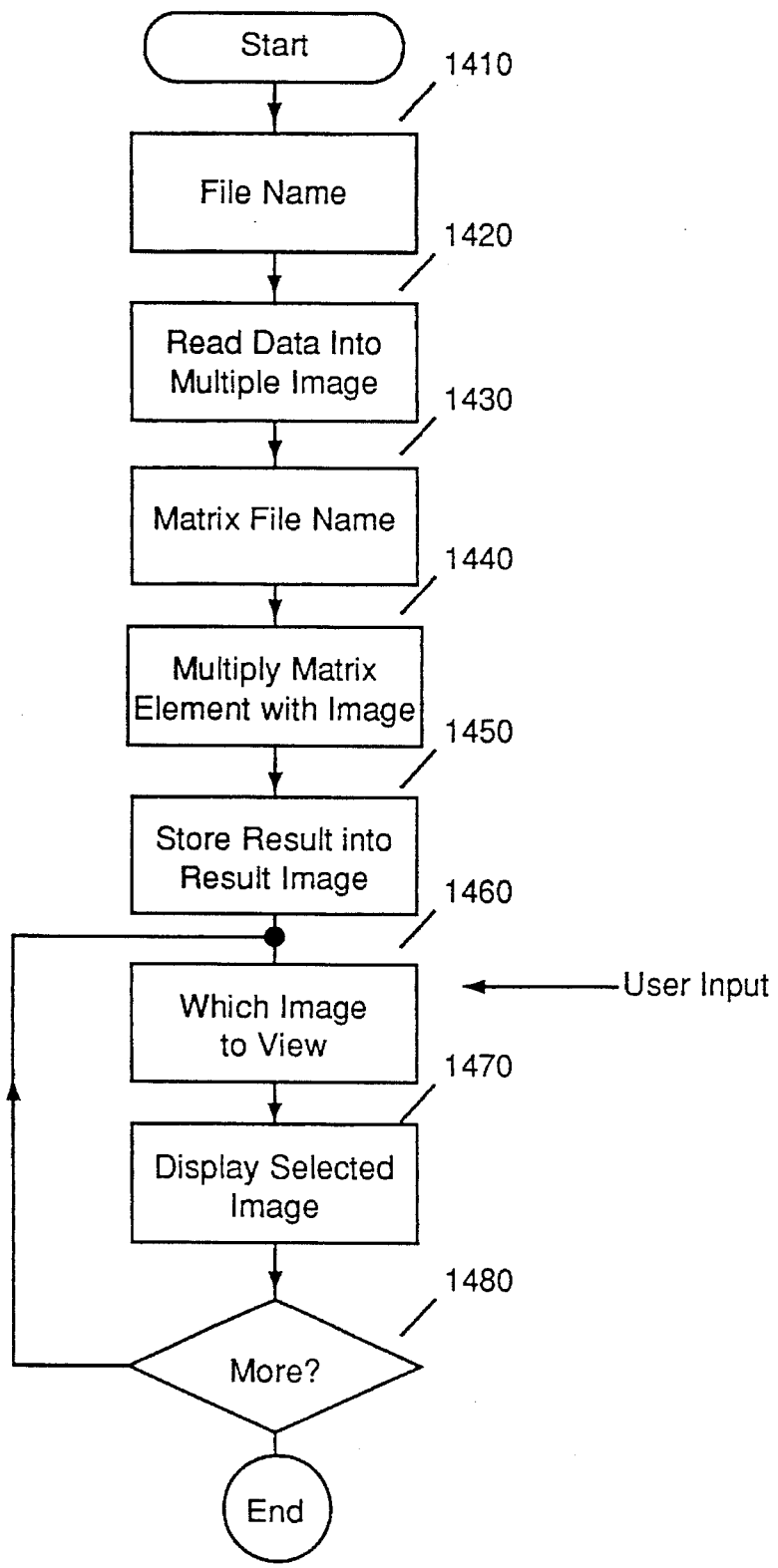
FIG. 14 is a flow chart illustrating the steps for image deconvolution.

FIG. 14 is a flow chart of the steps for spectrally deconvoluting the data acquired during the data acquisition steps, as defined in FIGS. 11a–11b. A source code listing representative of the software for spectral deconvolution is set forth in Appendix III.

Steps 1410 and 1420 are similar to 1210 and 1215 of FIGS. 12a–12b and therefore will not be described in detail. At step 1410, the user inputs the name of the data file from which the emission spectra is plotted. At step 1420, the system retrieves the data file and separates the data into multiple images, each representing an image of the sample at a specified observation wavelength.

At step 1430, the system queries the user for the name of the file containing the inverse emission cross section matrix elements. At step 1440, the system retrieves the matrix file and multiplies the corresponding inverse cross section matrix with the corresponding set of four monochromatic images. The resulting fluor density images are then stored in memory at step 1450. At step 1460, the user may choose which image to view by entering the desired observation wavelength. At step 1470, the system displays the image according to the value entered at step 1460. At step 1480, the user may choose to view an image having a different observation wavelength. If another image is chosen, the loop beginning at 1460 is repeated. In this manner, images depicting the surface densities of any label may be obtained. This methodology enables any spectral multiplexing scheme to be employed.

d. Example of spectral deconvolution of a 4-fluorophore system

Figure 15:
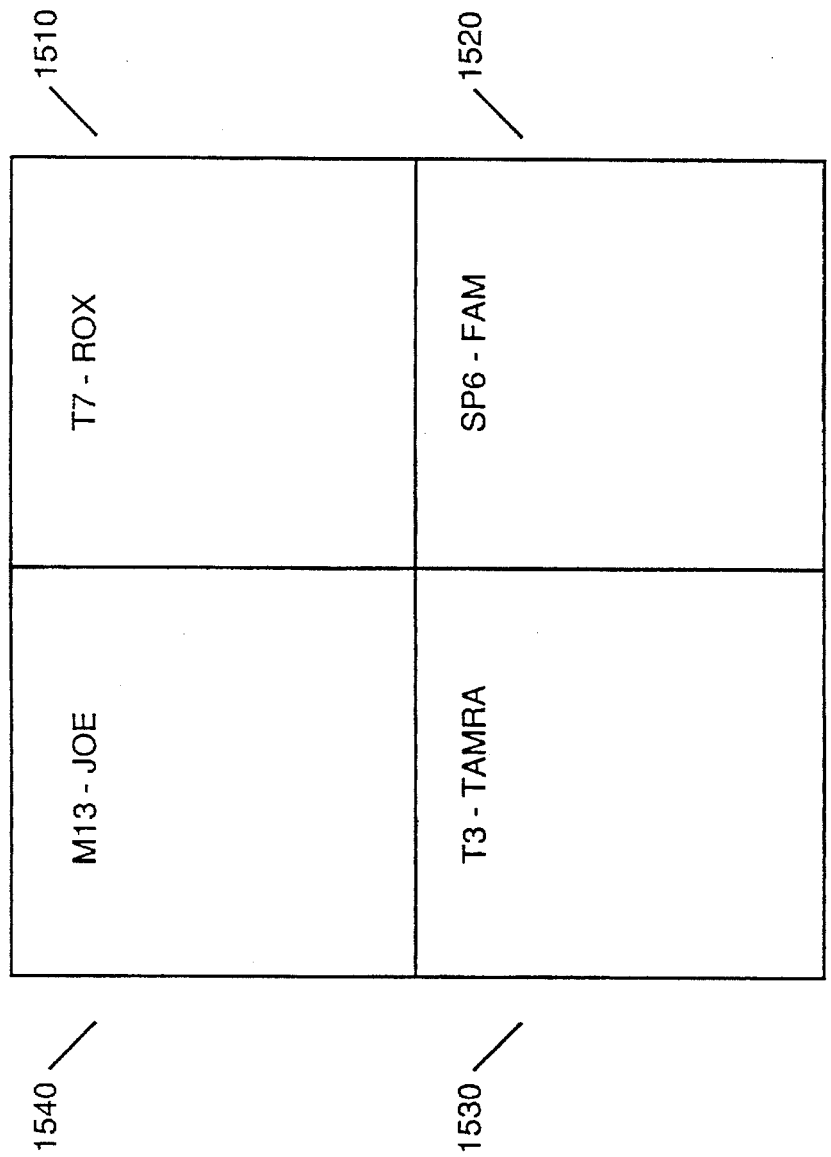
FIG. 15 shows the layout of the probe sample.

FIG. 15 illustrates the layout of a VLSIPS array that was used to demonstrate spectral deconvolution. As shown, the array was subdivided into four quadrants, each synthesized in a checkerboard pattern with a complement to a commercial DNA sequencing primer. For example, quadrant 1510 contains the complement to the T7 primer, quadrant 1520 contains the complement to SP6 primer, quadrant 1530 contains the complement to T3 primer, and quadrant 1540 contains the complement to M13 primer. Further, each primer was uniquely labeled with a different fluorophore from Applied Biosystems (ABI). In this particular experiment, SP6 was labeled with FAM (i.e. fluorescein), M13 was labeled with JOE (a tetrachloro-fluorescein derivative), T3 was labeled with TAMRA (a.k.a. tetramethylrhodamine), and T7 was labeled with ROX (Rhodamine X). In this format, each quadrant of the VLSIPS array was labeled with just one of the fluorophores. The array was then hybridized to a cocktail of the four primers. Following a hybridization period in excess of 6 hours with a target concentration of 0.1 nanomolar, the array was washed with 6X SSPE buffer and affixed to the spectral line scanner flow cell.

The array was scanned twice with 80 mW of argon laser power at 488 nm and at 514.5 nm excitation wavelengths. The beam was focused to a line 50 μm wide by 16 mm high. For each excitation wavelength, a series of 256 frames was collected by the CCD and stored. The camera format was 8-fold binning in the x or spectral direction and twofold binning in the y direction, for a format of (x, y)=(64, 256).

The x-axis motion controller was stepped 50 μm between frame acquisitions. The spectrograph was configured with an entrance slitwidth of 100 μm s, a 150 lines/mm ruled diffraction rating, and a central wavelength setting of 570 nm, producing a spectral bandpass from 480 nm to 660 nm.

The sets of spectral images were rearranged by interchanging the x and spectral indices to form two sets of 64 monochromatic images of the array, each of which is characterized by a unique combination of excitation and observation wavelengths. The spectral bandwidth subsumed by each image is found by dividing the full spectral bandwidth by the number of images, i.e. (600 nm–480 nm)/64=2.8 nm. The monochromatic images were rewritten as 8-bit intensities in the *.TIFF format.

Figure 16:
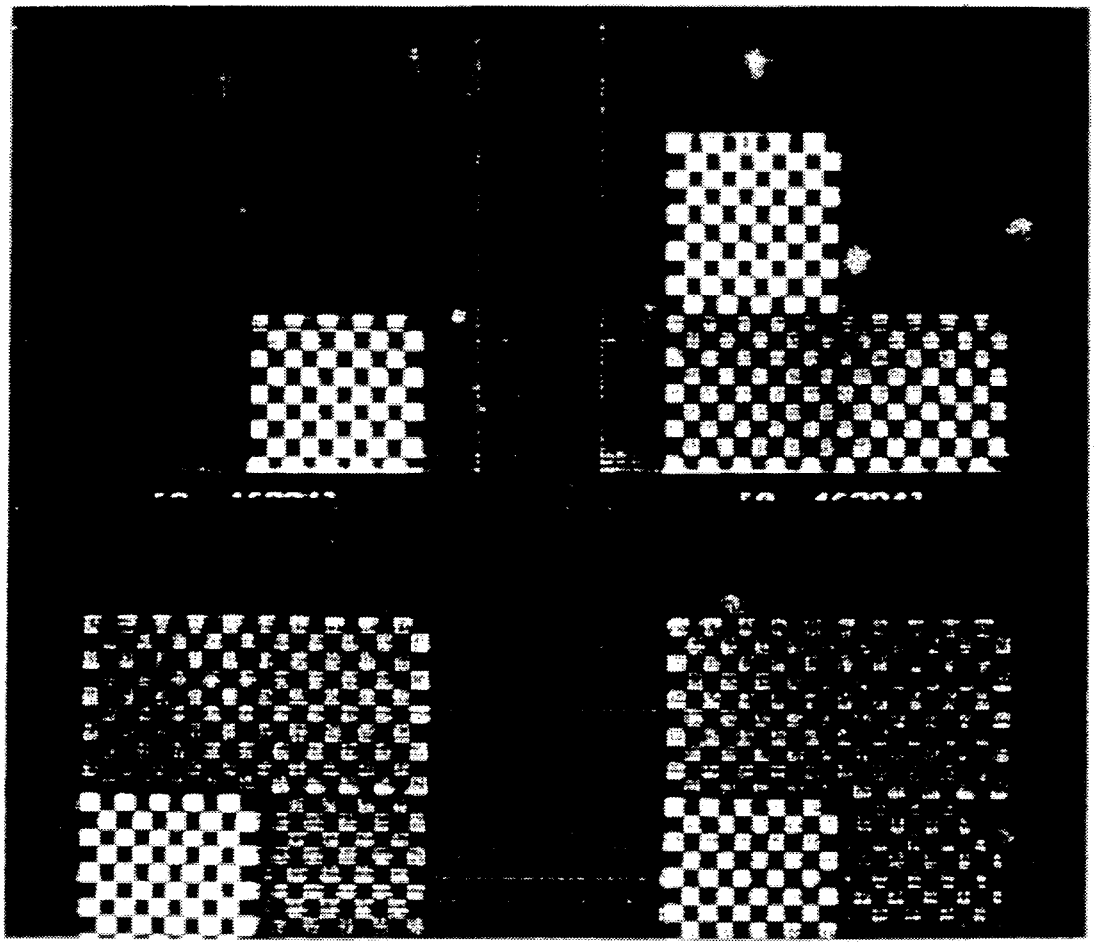
FIG. 16 shows examples of monochromatic images obtained by the imaging system of FIG. 9.

FIG. 16 illustrates a set of four representative monochromatic spectral images obtained from this experiment. Image 1601 was acquired with 488 nm excitation light at an observation wavelength of 511 nm. This image represents the emission generated by FAM. Image 1602, which was acquired with 488 nm excitation light at an observation wavelength of 553 nm, represents the signal emitted by JOE. Image 1603, which depicts the ROX signal, was acquired with a 514.5 nm excitation light at an observation wavelength of 608 nm. As for Image 1604, it was acquired with 514.5 nm excitation light at an observation wavelength of 578 nm. Image 1604 represents the signal emitted by TAMRA.

Figure 17:
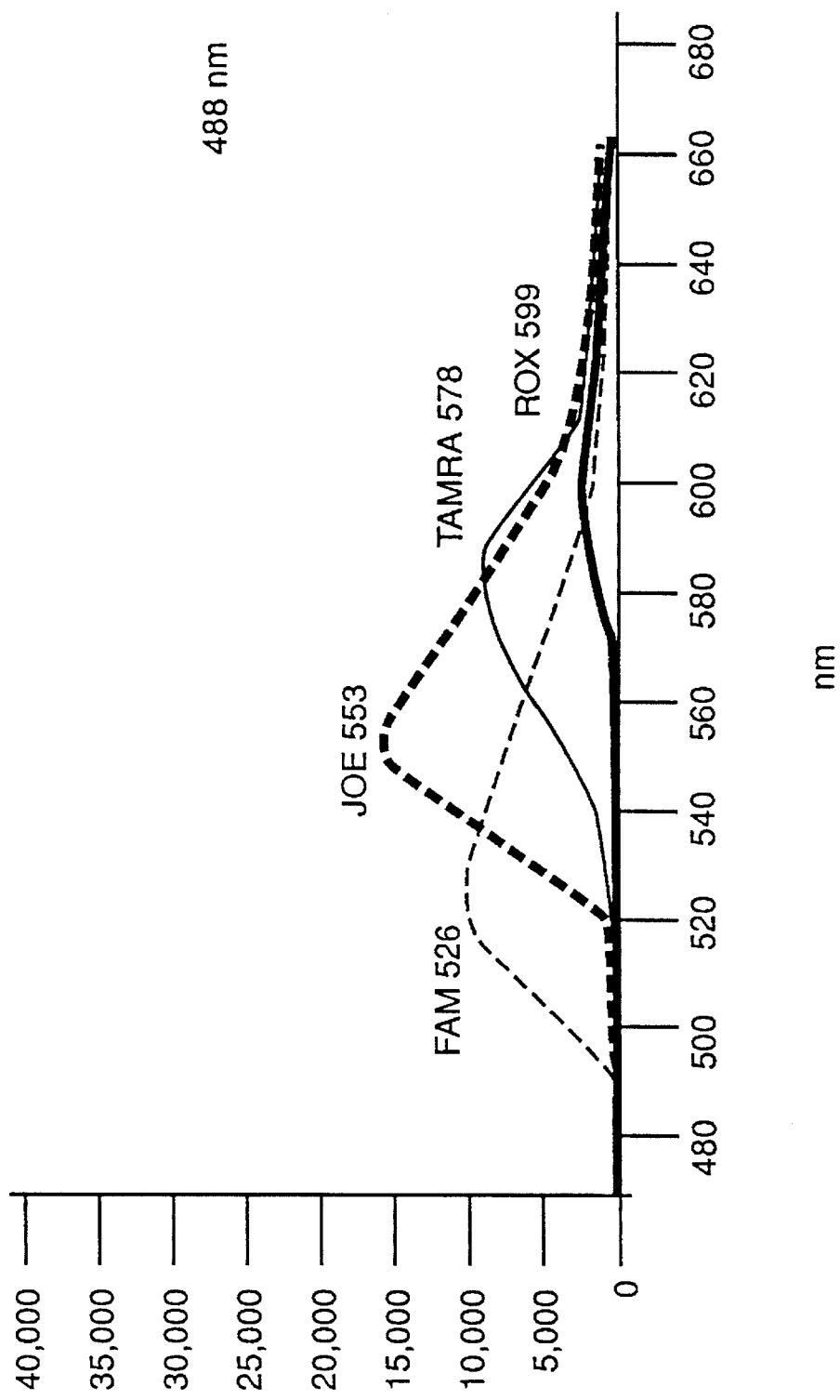
FIGS. 17–18 show the emission spectra obtained by the imaging system of FIG. 9.
Figure 18:
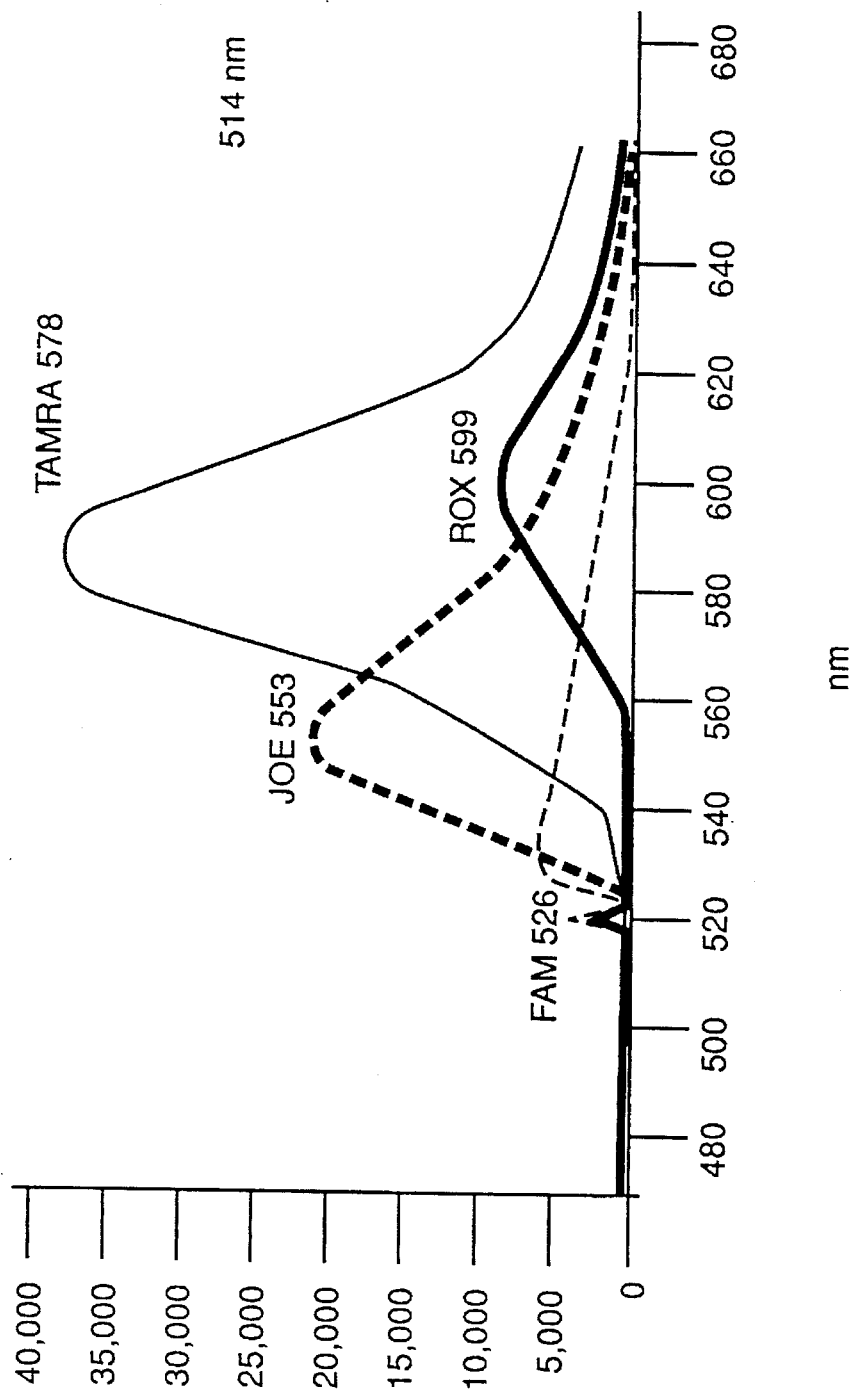

The next step involves obtaining the emission spectrum of each dye. FIGS. 17–18 illustrate the spectra obtained from within each of the 4 quadrants of the array at 488 and 514.5 excitation wavelengths, respectively. Since the labeled target molecules bound mutually exclusively to each quadrant of the array, each spectrum is a pure emission spectrum of just one of the ABI dyes. The observed differences in the integrated areas of the raw spectra result from differences in excitation efficiency and surface density of fluorophores. To increase the value of the signals, the spectra may be normalized. FIG. 13 illustrates the emission spectra of FIG. 17 after it has been normalized to unit area.

Reliable spectral deconvolution may be achieved by choosing four observation wavelengths at or near the emission maxima of each of the fluorophores. Inspecting the images of FIG. 16, it can be seen that the 510 nm image is sensitive only to the FAM dye. The other three are a mixtures of the other three fluors. FIG. 19 is a spreadsheet showing the derivation of the relative inverse cross section matrix from the images of FIGS. 13.

Figure 20:
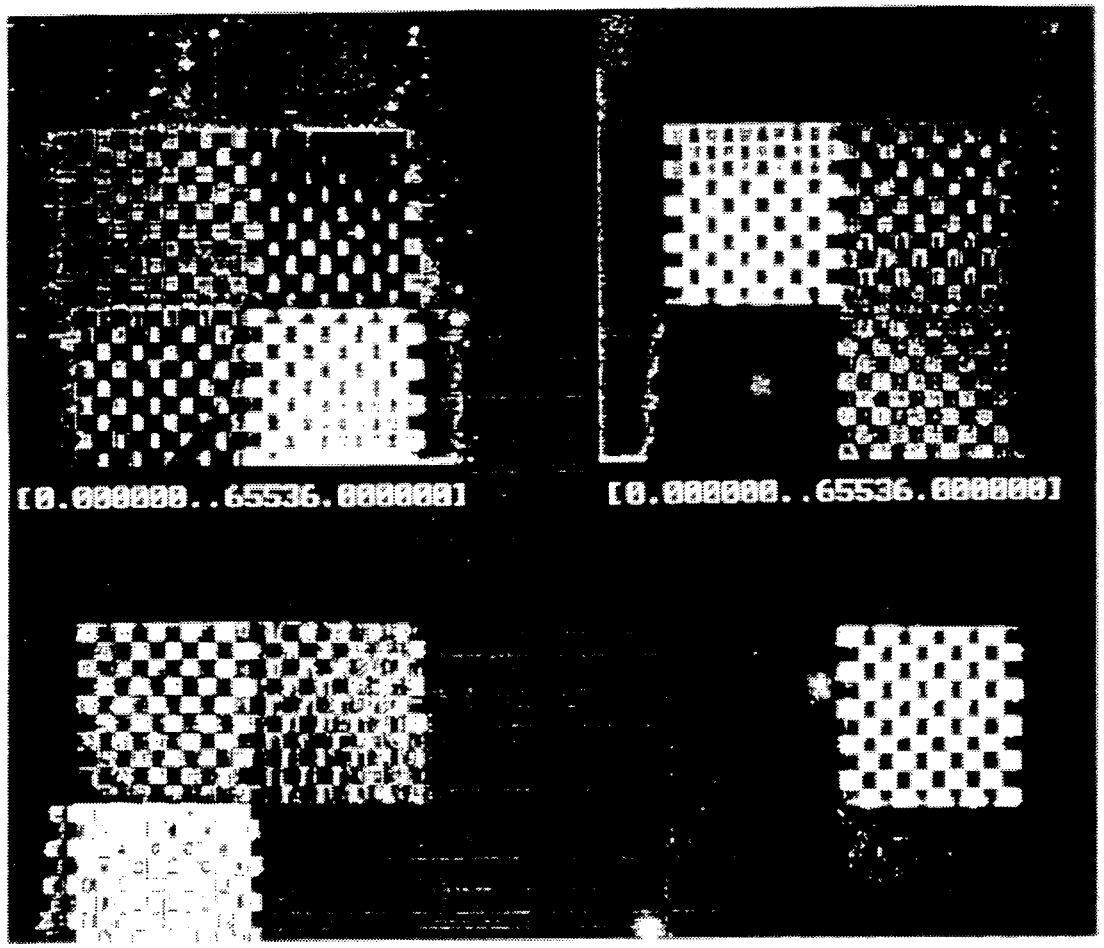
FIG. 20 shows examples of images representing the surface density of the fluorophores.

FIG. 20 illustrates the "fluor surface density images", obtained by multiplying the four chosen monochromatic images by the inverse of the relative emission cross section matrix. Images 2001, 2002, 2003, and 2004 represent the relative surface density of JOE, ROX, TAMRA, and FAM respectively. The signal and background levels in these images are summarized on the Figure. As illustrated, a multi-labeled signal has been deconvolved to provide signals, each substantially representing a unique label.

V. Detailed Description of Another Embodiment of the Imaging System

Figure 21:
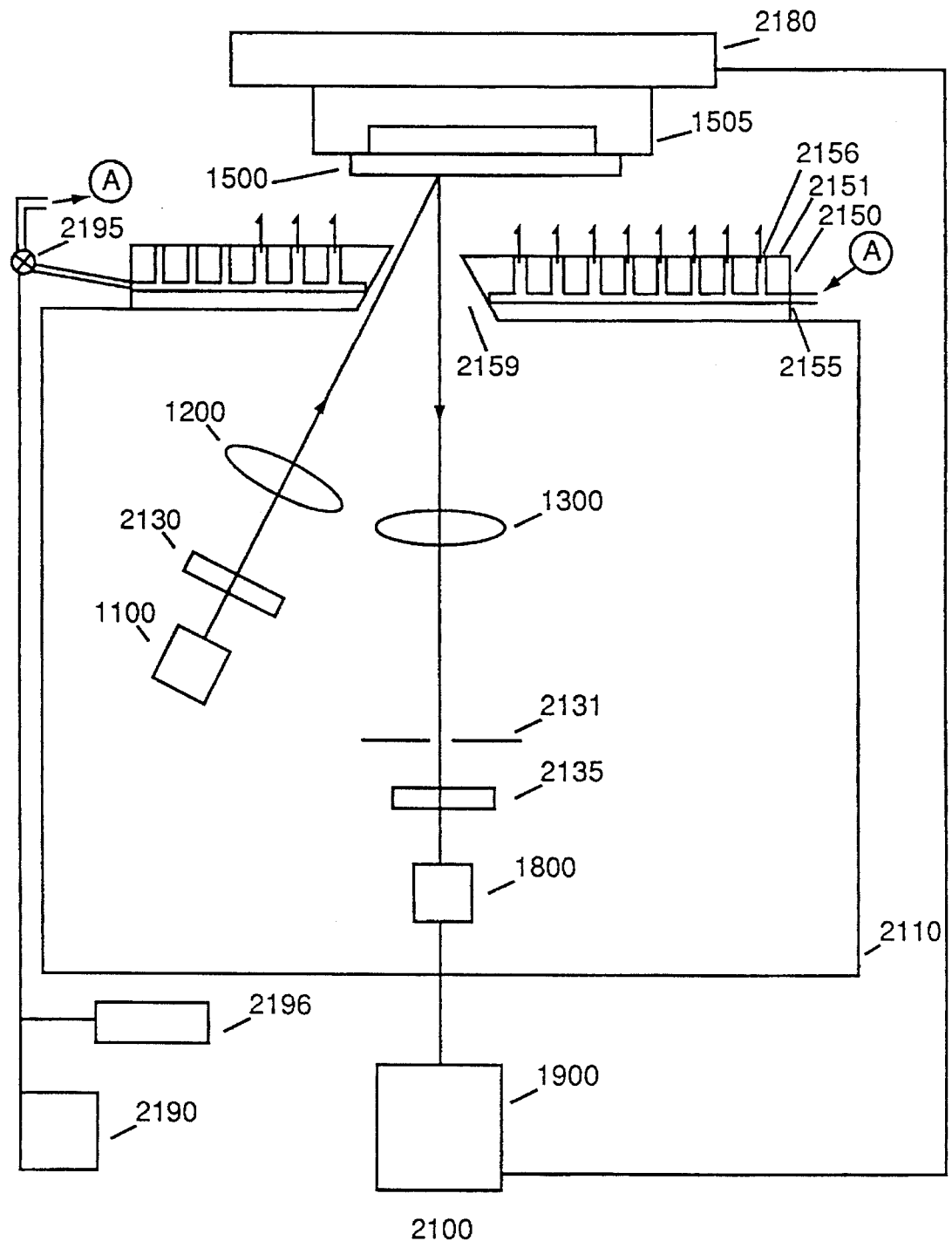
FIG. 21 shows an alternative embodiment of an imaging system.

FIG. 21 illustrates an alternative embodiment of the present invention. The system shown in FIG. 21 employs air bearings to maintain the sample in the plane of the excitation light. System 2100 includes a body 1505 on which a support 1500 containing a sample is mounted. In some embodiments, the body may be a flow cell that is of the type described in FIG. 4a–4d. The body may be mounted to a single-axis translation table so as to move the sample across the excitation light. The translation table may be of the type already discloses in conjunction with the systems in FIGS. 3 and 9. Movement of the translation stage may be controlled by a computer 1900.

An optics head assembly 2110 is located parallel to the sample. The optics head assembly may include components that are common with those described in FIG. 1. The common components are labeled with the same figure numbers. To avoid being redundant, these components will not be discussed here in detail. As shown, the optics head contains a light source 1100 for illuminating a sample 1500. Light source 1100 directs light through excitation optics 1200. The excitation optics transform the beam to a line capable of exciting a row of the sample simultaneously. In some applications, the light produced by the excitation source may be nonhomogeneous, such as that generated by an array of LEDs. In such cases, the excitation optics may employ light shaping diffusers manufactured by Physical Optics Corporation, ground glass, or randomizing fiber bundles to homogenize the excitation light. As the light illuminates the sample, labeled markers located thereon fluoresce. The fluorescence are collected by collection optics 1300. A collection slit 2131 may be located behind collection optics. In one embodiment, the optics head is aligned such that substantially only emission originating from the focal plane of the light pass through the slit. The emission are then filtered by a collection filter 2135, which blocks out unwanted emission such as illumination light scattered by the substrate. Typically, the filter transmits emission having a wavelength at or greater than the fluorescence and blocks emission having shorter wavelengths (i.e., blocking emission at or near the excitation wavelength). The emission are then imaged onto an array of light detectors 1800. Subsequent image lines are acquired by translating the sample relative to the optics head.

The imaging system is sensitive to the alignment between the sample and plane of the excitation light. If the chip plane is not parallel to the excitation line, image distortion and intensity variation may occur.

To achieve the desired orientation, the optics head is provided with a substantially planar plate 2150. The plate includes a slit 2159, allowing the excitation and collection light paths to pass through. An array of holes 2156, which are interconnected by a channel 2155, are located on the surface 2151 of the plate. The channels are connected to a pump 2190 that blows air through the holes at a constant velocity. The flow of air may be controlled via air flow valve 2195. The air creates a pneumatic pressure between the support and the plate. By mounting the optics head or the flow cell on a tilt stage, the pressure can be regulated to accurately maintain the plate parallel to the support. In some embodiments, the air pressure may be monitored and controlled by computer 1900. A ballast 2196 may be provided in the air line to dampen any pressure variations.

In some embodiments, the head unit may be mounted on a single-axis translation stage for focusing purposes. For example, the air pressure may be monitored to accurately locate the sample in the focal plane of the excitation light. Alternatively, the imaging system may employ a multi-axis translation stage, focusing optics, and associated components for focusing and scanning the sample, similar to the system disclosed in FIG. 3.

The present invention provides greatly improved methods and apparatus for imaging a sample on a device. It is to be understood that the above description is intended to be illustrative and not restrictive. Many embodiments will be apparent to those of skill in the art upon reviewing the above description.

Merely as an example, the focal lengths of the optical elements can be manipulated to vary the dimensions of the excitation light or even to make the system more compact. The optical elements may be interchanged with other optical elements to achieve similar results such as replacing the telescope with a microscope objective for expanding the excitation light to the desired diameter. In addition, resolution of the image may be manipulated by increasing or decreasing the magnification of the collection optics.

The scope of the invention should, therefore, be determined not with the reference to the above description, but should instead be determined with reference to the appended claims, along with the full scope of equivalents to which such claims are entitled.

APPENDIX I

LINE SCAN

```
'line scanner

DIM d%(0 TO 13), dat%(-15 TO 1024), ch%(0 TO 1039), dark%(1 TO 1024)
DIM volt(1 TO 250), encoder(1 TO 250)
COMMON SHARED d%(), dat%(), ch%()
DECLARE SUB cio16 (md%, BYVAL dummy%, F%)
'$DYNAMIC
DIM rawdat%(0 TO 2077)
'$STATIC
CHDIR "c:\linescan\data\generic"

'set default scan parameters
nscans% = 1
minutes = 2
bath$ = "n"
tstart% = 20
nscansinit% = 1
tstep% = 2
pixelsize% = 14
speed = 1
gain% = 1
surface$ = "2"
subdir$ = "generic"
filename$ = "test01"
nfilename$ = "test01.dat"
leftfilename$ = "test"
rightfilename$ = "01"
blank$ = "              "
hoffset = 0
voffset = 0
focusoffset = 0
glassthickness% = 700

'draw logo
SCREEN 12
LINE (219, 289)-(219, 189), 2
LINE -STEP(100, 0), 2
LINE -STEP(-100, 100), 2
PAINT (244, 239), 2
LINE (319, 189)-(419, 289), 8
LINE -STEP(0, -100), 8
LINE -STEP(-100, 100), 8
PAINT (394, 239), 8
SLEEP 1

'find number of empty loops needed for 5-msec delay
'time = TIMER
'FOR i = 1 TO 200000: NEXT
'time = TIMER - time
'IF time < 0 THEN time = time + 86400
'ncycles% = 1000 / time start:
CLOSE #2
CLOSE #4
```

```
CLOSE #8
OPEN "com1:9600,n,8,1,cs0,ds0" FOR RANDOM AS #8
ON ERROR GOTO errorhandler
SCREEN 0, 0, 0
SCREEN 0, 1, 1
COLOR 7
PRINT "number of scans:"; nscans%
LOCATE 1, 41
PRINT    "glass    thickness    (microns):    ";    CHR$(247);
LTRIM$(STR$(glassthickness%))
IF nscans% > 1 THEN COLOR 7 ELSE COLOR 8
PRINT "time between start of one scan and start of the next
(minutes):"; minutes
IF nscans% > 1 THEN
   LOCATE 2, 1
   COLOR 6
   PRINT "t"
END IF
COLOR 7
PRINT "   temperature controlled by computer: "; bath$
IF bath$ = "y" THEN COLOR 7 ELSE COLOR 8
GOSUB printbathstrings
COLOR 7
PRINT
PRINT "pixel size (microns):"; pixelsize%
PRINT "relative scan speed:"; speed
PRINT "gain:"; gain%
LOCATE 14, 1
PRINT "surface to focus on: "; surface$
LOCATE 14, 43
PRINT "focus offset (microns):"; focusoffset
PRINT "horizontal offset (microns):            vertical offset
(microns):"; voffset
LOCATE 15, 29
PRINT hoffset
PRINT "subdirectory for data file: "; subdir$
PRINT "file name: "; filename$
LOCATE 17, 43
PRINT "view or edit structured comment"
PRINT "comment: "; LEFT$(comment$, 71)
PRINT MID$(comment$, 72, 80)
LOCATE 20, 1
PRINT "start scan"
LOCATE 20, 41
PRINT "exit to DOS temporarily"
PRINT "quit"
COLOR 6
LOCATE 1, 1
PRINT "n"
LOCATE 1, 41
PRINT "g"
LOCATE 3, 1
PRINT "W"
LOCATE 8, 3
PRINT "x"
LOCATE 9, 16
```

```
PRINT "p"
LOCATE 10, 2
PRINT "a"
'LOCATE 7, 41
'PRINT "k"
LOCATE 14, 3
PRINT "r"
LOCATE 14, 41
PRINT "z"
LOCATE 15, 1
PRINT "h"
LOCATE 15, 41
PRINT "v"
LOCATE 16, 3
PRINT "b"
PRINT "f"
LOCATE 17, 41
PRINT "j"
PRINT "c"
PRINT
PRINT "s"
LOCATE 20, 63
PRINT "y"
PRINT "q"
COLOR 7

'initialize A/D board
d%(0) = 768                                 'CIO16 BASE I/O ADDRESS
d%(1) = 2                                   'INTERRUPT LEVEL
d%(2) = 1                                   'DMA LEVEL
md% = 0
F% = 0
CALL cio16(md%, VARPTR(d%(0)), F%)
IF F% <> 0 THEN PRINT "MODE 0 ERROR # "; F%: STOP OPEN "c:\linescan\setup" FOR INPUT AS #5
'focusfactor=1 for 1-micron encoder, focusfactor=2 for 0.5-micron
encoder
INPUT   #5,   focusmove,   horizmove,   vertmove,   powerfactor,
focusfactor
CLOSE #5 maininputloop:
DO
DO
 a$ = LCASE$(INKEY$)
LOOP WHILE a$ = ""
SELECT CASE a$
CASE "n"
   VIEW PRINT 23 TO 23
   INPUT "number of scans (1 min, 99 max)"; nscans1%
   VIEW PRINT
   IF nscans1% > 0 AND nscans1% < 100 THEN
      nscans% = nscans1%
      LOCATE 1, 17
      PRINT nscans%
```

```
      IF nscans% > 1 THEN COLOR 7 ELSE COLOR 8
      PRINT "time between start of one scan and start of the next
(minutes):"; minutes
      LOCATE 2, 1
      IF nscans% > 1 THEN
        COLOR 6
        PRINT "t"
      END IF
    ELSE BEEP
    END IF
CASE "g"
    VIEW PRINT 23 TO 23
    INPUT "approximate glass thickness in microns (100 min, 9999
max)"; glassthickness1%
    VIEW PRINT
    IF glassthickness1% > 99 AND glassthickness1% < 10000 THEN
      glassthickness% = glassthickness1%
      LOCATE 1, 69
      PRINT "      "
      LOCATE 1, 69
      PRINT LTRIM$(STR$(glassthickness%))
    ELSE BEEP
    END IF
CASE "t"
    IF nscans% > 1 THEN
      VIEW PRINT 23 TO 23
      INPUT "time between start of one scan and start of the next
(minutes):"; minutes1
      VIEW PRINT
      IF minutes1 >= 0 THEN
        minutes = minutes1
        LOCATE 2, 64
        PRINT minutes
      ELSE BEEP
      END IF
    ELSE BEEP
    END IF
CASE "w"
    IF bath$ = "n" THEN
      bath$ = "y"
    ELSE
      bath$ = "n"
      temperature$ = ""
    END IF
    LOCATE 3, 39
    PRINT bath$
    IF bath$ = "y" THEN COLOR 7 ELSE COLOR 8
    GOSUB printbathstrings
CASE "i"
    IF bath$ = "y" THEN
      VIEW PRINT 23 TO 23
      INPUT "initial temperature in degrees C (4 min, 60 max,
integer only)"; tstart1%
      VIEW PRINT
      IF tstart1% > 3 AND tstart1% < 61 THEN
        tstart% = tstart1%
```

```
          LOCATE 4, 33
          PRINT tstart%
        ELSE BEEP
        END IF
      ELSE BEEP
      END IF
   CASE "m"
      IF bath$ = "y" AND nscans% > 1 THEN
        VIEW PRINT 23 TO 23
        INPUT "number of scans at initial temperature"; nscansinit1%
        VIEW PRINT
        IF nscansinit1% > 0 AND nscansinit1% <= nscans% THEN
          nscansinit% = nscansinit1%
          LOCATE 5, 40
          PRINT nscansinit%
        ELSE BEEP
        END IF
      ELSE BEEP
      END IF
   CASE "e"
      IF bath$ = "y" AND nscans% > nscansinit% THEN
        VIEW PRINT 23 TO 23
        INPUT "temperature step in degrees C (integer only)"; tstep1%
        VIEW PRINT
        tfinal% = tstart% + (nscans% - 1) * tstep1%
        IF tfinal% > 3 AND tfinal% < 61 THEN
          tstep% = tstep1%
          LOCATE 6, 30
          PRINT tstep%
        ELSE
          VIEW PRINT 23 TO 25
          PRINT "With the parameters that you have chosen,"
          PRINT "the final temperature is <4 or >60 " + CHR$(248) +
"C."
          PRINT "Try again.  Press any key to continue";
          DO: LOOP WHILE INKEY$ = ""
          CLS 2
          VIEW PRINT
        END IF
      ELSE BEEP
      END IF
   CASE "x"
      VIEW PRINT 23 TO 23
      INPUT "pixel size in microns (14, 28, 42, or 56)"; pixelsize1%
      VIEW PRINT
      IF pixelsize1% = 14 OR pixelsize1% = 28 OR pixelsize1% = 42 OR
pixelsize1% = 56 THEN
        pixelsize% = pixelsize1%
        LOCATE 8, 22
        PRINT pixelsize%
      ELSE BEEP
      END IF
   CASE "p"
      VIEW PRINT 23 TO 23
      INPUT "relative scan speed (1, .5, .25, or .125)"; speed1
      VIEW PRINT
```

```
    IF speed1 = 1 OR speed1 = .5 OR speed1 = .25 OR speed1 = .125
THEN
       speed = speed1
       LOCATE 9, 21
       PRINT blank$
       LOCATE 9, 21
       PRINT speed
    ELSE BEEP
    END IF
 CASE "a"
    VIEW PRINT 23 TO 23
    INPUT "gain (1, 2, 4, or 8)"; gain1%
    VIEW PRINT
    IF gain1% = 1 OR gain1% = 2 OR gain1% = 4 OR gain1% = 8 THEN
       gain% = gain1%
       LOCATE 10, 6
       PRINT gain%
    ELSE BEEP
    END IF
 CASE "r"
    IF surface$ = "1" THEN surface$ = "2" ELSE surface$ = "1"
    LOCATE 14, 22
    PRINT surface$
 CASE "z"
    VIEW PRINT 23 TO 23
    INPUT "focus offset (microns)"; focusoffset
    VIEW PRINT
    LOCATE 14, 66
    PRINT blank$
    LOCATE 14, 66
    PRINT focusoffset
 CASE "h"
    VIEW PRINT 23 TO 23
    INPUT "horizontal offset (microns)"; hoffset
    VIEW PRINT
    LOCATE 15, 29
    PRINT blank$
    LOCATE 15, 29
    PRINT hoffset
 CASE "v"
    VIEW PRINT 23 TO 23
    INPUT "vertical offset (microns)"; voffset
    VIEW PRINT
    LOCATE 15, 67
    PRINT blank$
    LOCATE 15, 67
    PRINT voffset
 CASE "b"
    SCREEN 0, 2, 2
    CLS
    PRINT "The following subdirectories exist:"
    OPEN "c:\linescan\subdir.lst" FOR INPUT AS #1
    DO UNTIL EOF(1)
       INPUT #1, a$
       PRINT a$; "  ";
    LOOP
```

```
    CLOSE #1
    PRINT
asksubdir:
    INPUT "subdirectory for data file"; subdir$
    CHDIR "c:\linescan\data\" + subdir$
    SCREEN 0, 1, 1
    LOCATE 16, 29
    PRINT blank$
    LOCATE 16, 29
    PRINT subdir$
    SCREEN 0, 2, 2
    slide$ = ""
    seqfile$ = ""
    projseqstrand$ = ""
    targettype$ = ""
    targetconc$ = ""
    flowcellsoln$ = ""
    temperature$ = ""
    opname$ = ""
    other$ = ""
    GOTO listfiles
CASE "f"
    SCREEN 0, 2, 2
    CLS
listfiles:
    PRINT "Subdirectory " + subdir$ + " contains the following
files:"
    FILES "*.dat"
askfilename:
    DO
    IF nscans% > 1 THEN
        PRINT "Last 2 characters in filename must be a number less
than ";
        num$ = LTRIM$(STR$(101 - nscans%))
        IF 101 - nscans% < 10 THEN num$ = "0" + num$
        PRINT num$
        PRINT "and will be incremented by 1 for each scan."
    END IF
    DO
        INPUT "filename (8 characters maximum)"; filename$
        filename$ = LTRIM$(RTRIM$(filename$))
        length% = LEN(filename$)
        IF length% > 8 OR (length% < 3 AND nscans% > 1) OR length%
< 1 THEN
            PRINT "Too many or too few characters.  Try again."
        ELSEIF nscans% > 1 OR LEN(filename$) > 2 THEN
            rightfilename$ = RIGHT$(filename$, 2)
            leftfilename$ = LEFT$(filename$, length% - 2)
            nonnumeric% = 0
            IF nscans% > 1 THEN
            IF    ASC(LEFT$(rightfilename$,    1))   <   48   OR
ASC(LEFT$(rightfilename$, 1)) > 57 OR ASC(RIGHT$(rightfilename$,
1)) < 48 OR ASC(RIGHT$(rightfilename$, 1)) > 57 THEN
                PRINT "Last 2 characters must be numbers.  Try again"
                nonnumeric% = 1
            ELSEIF VAL(rightfilename$) > 100 - nscans% THEN PRINT "Last
```

```
2 characters must be a number less than"; num$
      END IF
        END IF
      END IF
  LOOP UNTIL length% > 0 AND length% < 9 AND (nscans% = 1 OR
(nonnumeric% = 0 AND VAL(rightfilename$) < 101 - nscans% AND
length% > 2))
  nfilename$ = filename$ + ".dat"
  OPEN nfilename$ FOR BINARY AS #2
  IF LOF(2) = 0 THEN
     CLOSE #2
     EXIT DO
  END IF
  DO
     INPUT "file already exists - overwrite (y or n)"; a$
     a$ = LCASE$(a$)
     IF a$ <> "y" AND a$ <> "n" THEN PRINT "type a single
character, either y for yes or n for no"
  LOOP UNTIL a$ = "y" OR a$ = "n"
  CLOSE #2
  IF a$ = "y" THEN
     KILL nfilename$
     EXIT DO
  END IF
  LOOP
  SCREEN 0, 1, 1
  LOCATE 17, 12
  PRINT blank$
  LOCATE 17, 12
  PRINT filename$
CASE "j"
  SCREEN 0, 2, 2
structuredcomments:
  CLS
  COLOR 8
  PRINT "file name: "; nfilename$
  COLOR 7
  PRINT "slide number: "; slide$
  PRINT "sequence file name: "; seqfile$
  PRINT "project/sequence/strand: "; projseqstrand$
  PRINT "target type: "; targettype$
  PRINT "target concentration: "; targetconc$
  PRINT "hybridization time and temperature: "; hybtimetemp$
  PRINT "flow cell solution: "; flowcellsoln$
  IF bath$ = "y" THEN
     COLOR 8
     temperature$ = LTRIM$(STR$(tstart%))
  END IF
  PRINT "scan temperature: "; temperature$
  COLOR 7
  PRINT "operator name: "; opname$
  PRINT "other comments: "; other$
  COLOR 8
  PRINT "rows:"; nlines%
  PRINT "columns:"; ngoodpixels%
  PRINT "x pixel size:"; pixelsize; "microns"
```

```
PRINT "y pixel size:"; linespacing%; "microns"
PRINT "scan speed:"; scanspeed; "mm/sec"
PRINT "laser power: "; power%
PRINT "date: "; DATE$
PRINT "time: "; TIME$
COLOR 7
PRINT
PRINT "erase all structured comments"
PRINT "return to main menu"
COLOR 6
LOCATE 2, 1
PRINT "s"
LOCATE 3, 3
PRINT "q"
PRINT "p"
LOCATE 5, 8
PRINT "t"
LOCATE 6, 8
PRINT "c"
PRINT "h"
PRINT "f"
IF bath$ = "n" THEN
   LOCATE 9, 8
   PRINT "m"
END IF
LOCATE 10, 10
PRINT "n"
PRINT "o"
LOCATE 21, 1
PRINT "e"
PRINT "r"
COLOR 7
DO
DO
   COLOR 8
   LOCATE 18, 7
   PRINT DATE$
   LOCATE 19, 7
   PRINT TIME$
   GOSUB powermeasure
   LOCATE 17, 13
   PRINT power%; "    "
   COLOR 7
   GOSUB shortdelay
   a$ = LCASE$(INKEY$)
LOOP WHILE a$ = ""
SELECT CASE a$
CASE "s"
   VIEW PRINT 24 TO 24
   INPUT "slide number"; slide$
   IF LEN(slide$) > 20 THEN slide$ = LEFT$(slide$, 20)
   VIEW PRINT
   LOCATE 2, 15
   PRINT blank$
   LOCATE 2, 15
   PRINT slide$
```

```
      CASE "q"
        VIEW PRINT 24 TO 24
        INPUT "sequence file name"; seqfile$
        IF LEN(seqfile$) > 20 THEN seqfile$ = LEFT$(seqfile$, 20)
        VIEW PRINT
        LOCATE 3, 21
        PRINT blank$
        LOCATE 3, 21
        PRINT seqfile$
      CASE "p"
        VIEW PRINT 24 TO 24
        LINE INPUT "project/sequence/strand? "; projseqstrand$
        projseqstrand$ = LTRIM$(RTRIM$(projseqstrand$))
        IF   LEN(projseqstrand$)   >   20   THEN   projseqstrand$   =
LEFT$(projseqstrand$, 20)
        VIEW PRINT
        LOCATE 4, 26
        PRINT blank$; blank$
        LOCATE 4, 26
        PRINT projseqstrand$
      CASE "t"
        VIEW PRINT 24 TO 24
        LINE INPUT "target type? "; targettype$
        targettype$ = LTRIM$(RTRIM$(targettype$))
        IF    LEN(targettype$)    >    20    THEN    targettype$    =
LEFT$(targettype$, 20)
        VIEW PRINT
        LOCATE 5, 14
        PRINT blank$; blank$
        LOCATE 5, 14
        PRINT targettype$
      CASE "c"
        VIEW PRINT 24 TO 24
        LINE INPUT "target concentration? "; targetconc$
        targetconc$ = LTRIM$(RTRIM$(targetconc$))
        IF    LEN(targetconc$)    >    20    THEN    targetconc$    =
LEFT$(targetconc$, 20)
        VIEW PRINT
        LOCATE 6, 23
        PRINT blank$; blank$
        LOCATE 6, 23
        PRINT targetconc$
      CASE "h"
        VIEW PRINT 24 TO 24
        LINE   INPUT   "hybridization   time   and   temperature?   ";
hybtimetemp$
        hybtimetemp$ = LTRIM$(RTRIM$(hybtimetemp$))
        IF    LEN(hybtimetemp$)    >    20    THEN    hybtimetemp$   =
LEFT$(hybtimetemp$, 20)
        VIEW PRINT
        LOCATE 7, 37
        PRINT blank$; blank$
        LOCATE 7, 37
        PRINT hybtimetemp$
      CASE "f"
        VIEW PRINT 24 TO 24
```

```
      LINE INPUT "flow cell solution? "; flowcellsoln$
      flowcellsoln$ = LTRIM$(RTRIM$(flowcellsoln$))
      IF   LEN(flowcellsoln$)   >   20   THEN   flowcellsoln$   =
LEFT$(flowcellsoln$, 20)
      VIEW PRINT
      LOCATE 8, 21
      PRINT blank$; blank$
      LOCATE 8, 21
      PRINT flowcellsoln$
    CASE "m"
      IF bath$ = "n" THEN
        VIEW PRINT 24 TO 24
        LINE INPUT "scan temperature? "; temperature$
        temperature$ = LTRIM$(RTRIM$(temperature$))
        IF   LEN(temperature$)   >   20   THEN   temperature$   =
LEFT$(temperature$, 20)
        VIEW PRINT
        LOCATE 9, 19
        PRINT blank$
        LOCATE 9, 19
        PRINT temperature$
      ELSE BEEP
      END IF
    CASE "n"
      VIEW PRINT 24 TO 24
      LINE INPUT "operator name? "; opname$
      IF LEN(opname$) > 20 THEN opname$ = LEFT$(opname$, 20)
      VIEW PRINT
      LOCATE 10, 16
      PRINT blank$
      LOCATE 10, 16
      PRINT opname$
    CASE "o"
      VIEW PRINT 24 TO 24
      LINE INPUT "other comments? "; other$
      other$ = LTRIM$(RTRIM$(other$))
      IF LEN(other$) > 40 THEN other$ = LEFT$(other$, 40)
      VIEW PRINT
      LOCATE 11, 17
      PRINT blank$; blank$; blank$; blank$
      LOCATE 11, 17
      PRINT other$
    CASE "e"
      VIEW PRINT 24 TO 24
      INPUT "Do you really want to erase all of these comments (y
or n)"; a$
      VIEW PRINT
      IF LCASE$(a$) = "y" THEN
        slide$ = ""
        seqfile$ = ""
        projseqstrand$ = ""
        targettype$ = ""
        targetconc$ = ""
        hybtimetemp$ = ""
        flowcellsoln$ = ""
        temperature$ = ""
```

```
        opname$ = ""
        other$ = ""
        GOTO structuredcomments
      END IF
    CASE "r"
      SCREEN 0, 1, 1
      GOTO maininputloop
    CASE ELSE
      BEEP
    END SELECT
    LOOP
  CASE "c"
    VIEW PRINT 23 TO 25
    LINE INPUT "comment (up to 151 characters)? "; comment$
    comment$ = LTRIM$(RTRIM$(comment$))
    comment$ = LEFT$(comment$, 151)
    CLS 2
    VIEW PRINT
    LOCATE 18, 10
    PRINT SPACE$(71)
    PRINT SPACE$(80)
    LOCATE 18, 10
    PRINT LEFT$(comment$, 71)
    PRINT MID$(comment$, 72, 80)
  CASE "s"
    EXIT DO
  CASE "y"
    SCREEN 0, 2, 2
    CLS
    DO
      SHELL "cd"
      LINE INPUT "enter a DOS command (or enter 'done')>"; dosstring$
      dosstring$ = LTRIM$(RTRIM$(LCASE$(dosstring$)))
      IF dosstring$ = "done" THEN EXIT DO
      IF dosstring$ = "scan" OR dosstring$ = "linescan" THEN
        BEEP
      ELSE IF dosstring$ <> "" THEN SHELL dosstring$
      END IF
      PRINT
    LOOP
    SHELL "c:"
    SHELL "c:\logout.bat"
    CHDIR "c:\linescan\data\" + subdir$
    SCREEN 0, 1, 1
  CASE "q"
    SYSTEM
  CASE ELSE
    BEEP
  END SELECT
  COLOR 7
LOOP
SCREEN 0, 2, 2
CLS IF   nscans%   >   1   AND   (LEN(filename$)   <   3   OR
```

```
ASC(LEFT$(rightfilename$, 1)) < 48 OR ASC(LEFT$(rightfilename$,
1)) > 57 OR ASC(RIGHT$(rightfilename$, 1)) < 48 OR
ASC(RIGHT$(rightfilename$, 1)) > 57 OR VAL(rightfilename$) > 100
- nscans%) THEN
   DO: LOOP UNTIL INKEY$ = ""
   PRINT "If you want to do"; nscans%; "scans, you must choose
another file name."
   PRINT "Press any key to return to menu."
   DO: LOOP WHILE INKEY$ = ""
   GOTO start
END IF
OPEN nfilename$ FOR BINARY AS #2
IF LOF(2) > 0 THEN
   DO
      PRINT "file " + filename$ + " already exists - overwrite (y
or n)";
      INPUT a$
      a$ = LCASE$(a$)
      IF a$ <> "y" AND a$ <> "n" THEN PRINT "type a single
character, either y for yes or n for no"
   LOOP UNTIL a$ = "y" OR a$ = "n"
   CLOSE #2
   IF a$ = "y" THEN
      KILL nfilename$
   ELSE
      CLOSE #8
      GOTO start
   END IF
END IF
CLOSE #2 dataline$ = SPACE$(2048)
IF pixelsize% = 28 THEN dataline$ = SPACE$(1024)
IF pixelsize% = 42 THEN dataline$ = SPACE$(682)
IF pixelsize% = 56 THEN dataline$ = SPACE$(512)

IF bath$ = "y" THEN
   DO
      OPEN "com2:2400,n,8,1,cs0,ds0" FOR RANDOM AS #4
      delaytime = .2
      GOSUB delay
      PRINT #4, "#1r0"
      GOSUB delay
      a$ = INPUT$(LOC(4), #4)
      IF INSTR(a$, "#1r0= ") > 0 THEN EXIT DO
      GOSUB delay
      PRINT #4, "#1r0"
      GOSUB delay
      a$ = INPUT$(LOC(4), #4)
      IF INSTR(a$, "#1r0= ") > 0 THEN EXIT DO
      CLOSE #4
      GOSUB delay
      PRINT "Computer can not communicate with temperature
controller."
      PRINT "Make sure controller is turned on and RS-232 cable is
connected."
```

```
      PRINT "Press any key when ready to try again."
      DO: LOOP WHILE INKEY$ = ""
   LOOP
END IF SHELL "dir c:\empty>c:\dir.dir"
OPEN "c:\dir.dir" FOR INPUT AS #9
DO
   LINE INPUT #9, a$
   a% = INSTR(a$, "bytes free")
LOOP UNTIL a% > 0
CLOSE #9
bytesfree& = VAL(LEFT$(a$, a% - 1))
bytesneeded& = (512& + 411041792 \ pixelsize% \ pixelsize%) *
nscans%
IF bytesfree& < bytesneeded& THEN
   DO: LOOP UNTIL INKEY$ = ""
   BEEP
   PRINT
   PRINT "There is not enough space on the disk for your file";
   IF nscans% > 1 THEN PRINT "s." ELSE PRINT "."
   PRINT "You need"; bytesneeded&; "bytes but there are only";
bytesfree&; "bytes available."
   PRINT
   PRINT "Press any key to return to menu."
   CLOSE #2
   CLOSE #4
   CLOSE #8
   DO: LOOP WHILE INKEY$ = ""
   GOTO start
END IF
IF bytesfree& < 5000000 THEN
   BEEP
   PRINT
   PRINT "There are only"; bytesfree&; "bytes free on the hard
disk."
   PRINT "Delete some files soon."
   BEEP
   SLEEP 1
END IF

ON ERROR GOTO 0 scanspeed = .00534 * speed * pixelsize%         '.006007 at 125
kHz
scanspeed$ = ".       "
FOR i% = 1 TO 5
   IF scanspeed < 10 ^ (i% - 6) THEN EXIT FOR
   scanspeed = scanspeed * 10
   MID$(scanspeed$, i% + 1, 1) = LTRIM$(STR$(INT(scanspeed)))
   scanspeed = scanspeed - INT(scanspeed)
NEXT i%
scanspeed$ = RTRIM$(scanspeed$)
PRINT
PRINT "scanspeed$="; scanspeed$
'PRINT "ncycles%="; ncycles%
```

```
PRINT
PRINT "Stages are moving to their home positions.  Please wait.":
PRINT "Press the F1 key for emergency stop."
KEY(1) ON
ON KEY(1) GOSUB emergencystop
PRINT #8, "mn j0 fsa0 fsb1 fsc0 a80 d-999999 2d999999 v4 g "
INPUT #8, echo$
'wait for stages to run into limit switches
DO
   PRINT #8, "3r "
   GOSUB readr
   GOSUB shortdelay
LOOP UNTIL INSTR(r$, "3r *S") > 0
DO
   PRINT #8, "2r "
   GOSUB readr
   GOSUB shortdelay
LOOP UNTIL INSTR(r$, "2r *S") > 0
DO
   PRINT #8, "1r "
   GOSUB readr
   GOSUB shortdelay
LOOP UNTIL INSTR(r$, "1r *S") > 0
'set encoder counts to 0
PRINT #8, "pz "
INPUT #8, echo$ 'GOSUB powermeasure
PRINT
'PRINT "power="; power%; "uW"
'PRINT USING "noise= #.## mV"; noise * 1000
'GOSUB shortdelay
'PRINT
DO: LOOP UNTIL INKEY$ = ""
PRINT "Load sample.  Press any key when done."
'cursorline% = CSRLIN
'cursorline% = cursorline% - 4
DO
'   GOSUB powermeasure
'   LOCATE cursorline%, 7
'   PRINT power%; "uW          "
'   LOCATE cursorline% + 1, 7
'   PRINT USING " #.## mV"; noise * 1000
LOOP WHILE INKEY$ = ""
'LOCATE CSRLIN + 2, 1
PRINT "Stages are moving. Please wait."
horizmove = INT(horizmove - voffset)
vertmove = INT(vertmove + hoffset)
a$ = LTRIM$(STR$(focusmove + (700 - glassthickness%) * focusfactor))
PRINT #8, "v6 1d" + a$ + " 1g 2d" + LTRIM$(STR$(horizmove)) + " 2g "
INPUT #8, echo$
PRINT #8, "3d" + LTRIM$(STR$(vertmove)) + " 3g fsb0 "
INPUT #8, echo$
GOSUB waitloop1
```

```
GOSUB waitloop2
GOSUB waitloop3

FOR scannumber% = 1 TO nscans%
IF bath$ = "y" THEN
   PRINT
   PRINT "changing temperature";
   t% = tstart%
   IF scannumber% > nscansinit% THEN t% = tstart% + (scannumber%
- nscansinit%) * tstep%
   PRINT #4, "#1m1 " + LTRIM$(RTRIM$(STR$(t%))) + ".0"
   delaytime = .2
   GOSUB delay
   LINE INPUT #4, echo$
   PRINT echo$;
   GOSUB delay
   DO
      PRINT #4, "#1r0"
      SLEEP 1
      LINE INPUT #4, tnow$
      a% = INSTR(tnow$, "=")
      tnow$ = MID$(tnow$, a% + 3)
      tnow$ = LEFT$(tnow$, LEN(tnow$) - 1)
      IF VAL(tnow$) < 10 THEN tnow$ = MID$(tnow$, 2)
      IF scannumber% > 1 THEN LOCATE 30, 1
      PRINT
      PRINT tnow$ + CHR$(248) + "C ";
      SLEEP 4
   LOOP UNTIL ABS(VAL(tnow$) - t%) <= .1
   PRINT
END IF IF scannumber% > 1 AND bath$ = "y" THEN
   IF surface$ = "1" THEN
      PRINT #8, "1v10 1d-2000 1g "
      INPUT #8, echo$
      GOSUB waitloop1
   ELSE
      PRINT #8, "1v10 1d-4000 1g "
      INPUT #8, echo$
      GOSUB waitloop1
   END IF
   SLEEP 1
END IF IF scannumber% > 1 THEN
   rightfilename$ = LTRIM$(STR$(VAL(rightfilename$) + 1))
   IF VAL(rightfilename$) < 10 THEN rightfilename$ = "0" +
rightfilename$
   filename$ = leftfilename$ + rightfilename$
   nfilename$ = filename$ + ".dat"
END IF IF scannumber% = 1 OR bath$ = "y" THEN
   OUT 779, 7
   focusmax = 0
```

```
focusmin = 199999
misfocusthreshold = 50
'find focus at 2 sides of area to be scanned
PRINT
PRINT "Finding focus.  Please wait.";
logfile$ = "c:\linescan\linescan.log"
OPEN logfile$ FOR APPEND AS #3
PRINT #3, " "
PRINT #3, subdir$, nfilename$, DATE$, TIME$
CLOSE #3
GOSUB findfocus
secondfocus = focus
OPEN logfile$ FOR APPEND AS #3
PRINT #3, "focus   x0     ";
PRINT #3, USING "##### ###.#    "; focus / focusfactor; x0;
CLOSE #3
IF surface$ = "1" THEN
   PRINT #8, "1v10 1d-1000 1g "
ELSE
   steps$ = "3000"
   IF glassthickness% > 700 THEN steps$ = LTRIM$(STR$(3000 +
(glassthickness% - 700) * 5 / 1.5))
   PRINT #8, "1v10 1d-" + steps$ + " 1g "
END IF
INPUT #8, echo$
PRINT #8, "2a80 2v10 2d70550 2g "
INPUT #8, echo$
GOSUB waitloop2
GOSUB findfocus
firstfocus = focus
OPEN logfile$ FOR APPEND AS #3
PRINT #3, USING "##### ###.#    "; focus / focusfactor; x0
CLOSE #3
PRINT
PRINT "focus positions vary by"; focusrange / focusfactor;
"microns";
PRINT
scantime = 469.7 / speed / pixelsize%
focussteps = INT(5 * (secondfocus - firstfocus) / focusfactor)
focussteps$ = LTRIM$(STR$(focussteps))
focusspeed = ABS(focussteps / scantime / 25000)
focusspeed$ = ".         "
FOR i% = 1 TO 5
   IF focusspeed < 10 ^ (i% - 6) THEN EXIT FOR
   focusspeed = focusspeed * 10
   MID$(focusspeed$, i% + 1, 1) = LTRIM$(STR$(INT(focusspeed)))
   focusspeed = focusspeed - INT(focusspeed)
NEXT i%
focusspeed$ = RTRIM$(focusspeed$)
  PRINT "focussteps$="; focussteps$, "focusspeed$="; focusspeed$;
ELSE
  PRINT #8, "2a80 2v10 2d70550 2g "
  INPUT #8, echo$
  GOSUB waitloop2
END IF
```

```
'move focus stage to starting position
IF firstfocus < secondfocus THEN
   PRINT #8, "1a10 1v1 1d-4000 1g "
   INPUT #8, echo$
   GOSUB waitloop1
   PRINT #8, "1d3000 1g "
   INPUT #8, echo$
   GOSUB waitloop1
   GOSUB read1
   PRINT #8, "1d" + LTRIM$(STR$(5 * (firstfocus - VAL(a$)) /
focusfactor - 100)) + " 1g "
   INPUT #8, echo$
ELSE
   PRINT #8, "1a10 1v1 1d4000 1g "
   INPUT #8, echo$
   GOSUB waitloop1
   PRINT #8, "1d-3000 1g "
   INPUT #8, echo$
   GOSUB waitloop1
   GOSUB read1
   PRINT #8, "1d" + LTRIM$(STR$(5 * (firstfocus - VAL(a$)) /
focusfactor + 100)) + " 1g "
   INPUT #8, echo$
END IF
GOSUB read1
PRINT #8, "1d" + LTRIM$(STR$(5 * (firstfocus - VAL(a$)) /
focusfactor)) + " 1g "
INPUT #8, echo$
GOSUB waitloop1
PRINT #8, "1d" + focussteps$ + " 1v" + focusspeed$ + " 2a2
2d-75787 2v" + scanspeed$ + " "
INPUT #8, echo$ 'set voltage for LED
'D/A board (Computer Boards Inc, CIO-DAC02) is at base address
640 (&H280)
'out 641, 0 --> 0 V
'out 641, 255 --> 4.98 V
SELECT CASE speed
CASE 1
   d%(1) = 9
   OUT 641, 135
CASE .5
   d%(1) = 18
   OUT 641, 112
CASE .25
   d%(1) = 36
   OUT 641, 98
CASE .125
   d%(1) = 72
   OUT 641, 89
END SELECT md% = 17                            'DETERMINE CLOCK RATE
'clock rate = 10 MHZ / (d%(0) * d%(1))
d%(0) = 5
```

```
CALL cio16(md%, VARPTR(d%(0)), F%)
IF F% <> 0 THEN PRINT "ERROR IN SETTING TIMER RATE. ERROR # ";
F%: STOP d%(0) = 0
d%(1) = 0
md% = 1
CALL cio16(md%, VARPTR(d%(0)), F%)
IF F% <> 0 THEN PRINT "ERROR IN SETTING CHANNEL LIMITS # "; F%:
STOP OUT 779, 4                              '0-.625 V
IF gain% = 2 THEN OUT 779, 5            '0-1.25 V
IF gain% = 4 THEN OUT 779, 6            '0-2.5 V
IF gain% = 8 THEN OUT 779, 7            '0-1.25 V OPEN "d:tempfile.dat" FOR BINARY AS #2
a$ = " "
FOR i% = 1 TO 100
   PUT #2, i%, a$
NEXT
a$ = STRING$(1, 0)
FOR i% = 101 TO 512
   PUT #2, i%, a$
NEXT
a$ = CHR$(252)
PUT #2, 1, a$
cols% = 14336 \ pixelsize%
PUT #2, , cols%
rows% = 14336 \ pixelsize%
PUT #2, , rows%
totalpoints& = 1& * rows% * cols%
PUT #2, , totalpoints&
OPEN logfile$ FOR APPEND AS #3
b$ = "CLS=" + LTRIM$(STR$(cols%))
PUT #2, 34, b$
PRINT #3, b$ + " ";
b$ = "RWS=" + LTRIM$(STR$(rows%))
PUT #2, 43, b$
PRINT #3, b$ + " ";
b$ = "SIZ=" + LTRIM$(STR$(pixelsize%))
PUT #2, 52, b$
PRINT #3, b$ + " ";
b$ = "VE=" + scanspeed$
PUT #2, 59, b$
PRINT #3, b$ + " ";
IF bath$ = "y" THEN
   b$ = "TMP=" + LTRIM$(STR$(t%))
   PUT #2, 72, b$
   PRINT #3, b$ + " ";
END IF
'b$ = LTRIM$(STR$(power%))
'PUT #2, 79, b$
PRINT #3, ' "power=" + b$
CLOSE #3
b$ = MID$(DATE$, 1, 6) + MID$(DATE$, 9, 2)
```

```
PUT #2, 83, b$
b$ = TIME$
PUT #2, 92, b$ delim$ = " " + CHR$(20) + " "
IF comment$ = "" THEN comment$ = " "
PUT #2, 101, comment$
IF slide$ <> "" OR seqfile$ <> "" OR projseqstrand$ <> "" OR
targettype$ <> "" OR targetconc$ <> "" OR hybtimetemp$ <> "" OR
flowcellsoln$ <> "" OR opname$ <> "" OR other$ <> "" OR
(temperature$ <> "" AND bath$ = "n") THEN
   PUT #2, , delim$
   PUT #2, , slide$
   PUT #2, , delim$
   PUT #2, , seqfile$
   PUT #2, , delim$
   PUT #2, , projseqstrand$
   PUT #2, , delim$
   PUT #2, , targettype$
   PUT #2, , delim$
   PUT #2, , targetconc$
   PUT #2, , delim$
   PUT #2, , hybtimetemp$
   PUT #2, , delim$
   PUT #2, , flowcellsoln$
   PUT #2, , delim$
   PUT #2, , temperature$
   PUT #2, , delim$
   PUT #2, , opname$
   PUT #2, , delim$
   PUT #2, , other$
   PUT #2, , delim$
END IF
CLOSE #2

IF scannumber% > 1 THEN
   time0 = scanstarttime
   time1 = time0 + minutes * 60
   DO
      SLEEP 1
      timenow = TIMER
      IF timenow < time0 THEN time1 = time1 - 86400
      timeleft = time1 - timenow
      PRINT
      IF timeleft > 0 THEN PRINT "next scan will start in " +
LTRIM$(STR$(INT(timeleft))) + " seconds";
      time0 = timenow
   LOOP UNTIL timeleft < 1
END IF IF scannumber% = 1 THEN
   SCREEN 12
   CLS
   VIEW PRINT 30 TO 30
   FOR i% = 0 TO 15
      PALETTE i%, 263172 * i%
```

```
      NEXT
   END IF

GOSUB takedata
   PRINT
   PRINT highclip&; "pixels clipped high,"; lowclip&; "pixels
clipped low";
   SHELL "copy d:tempfile.dat c:" + nfilename$ + " >d:junk"
   SHELL "del d:tempfile.dat"
NEXT scannumber%
DO: LOOP UNTIL INKEY$ = ""
DO
   PRINT
   PRINT "Done with scan.  Press any key to continue.";
   time = TIMER
   DO
      IF TIMER < time THEN time = time - 86400
   LOOP UNTIL TIMER > time + 1
   IF INKEY$ <> "" THEN EXIT DO
   PRINT
   PRINT highclip&; "pixels clipped high,"; lowclip&; "pixels
clipped low";
   time = TIMER
   DO
      IF TIMER < time THEN time = time - 86400
   LOOP UNTIL TIMER > time + 1
LOOP
CLOSE #4
PRINT
DO
   INPUT "move stage up so you can remove the sample (y or n)";
y$
   y$ = LCASE$(y$)
LOOP UNTIL y$ = "y" OR y$ = "n"
IF y$ = "y" THEN
   PRINT #8, "3v6 3d-700000 3g "
   INPUT #8, echo$
END IF
DO
   INPUT "quit (y or n)"; y$
   y$ = LCASE$(y$)
LOOP UNTIL y$ = "y" OR y$ = "n"
CLOSE #8
IF y$ = "n" THEN GOTO start
SYSTEM 'dead code starts here
sum = 0
FOR i% = 1 TO 100
   'status = AI.VRead(1, 0, 20, voltage#)
   sum = sum + voltage#
NEXT
power% = INT(sum * 10 * powerfactor + .5)
PRINT
PRINT
PRINT power%; "uW";
```

```
'END IF
IF focussteps <> 0 THEN PRINT #8, "1v" + focusspeed$ + " 1d" +
focussteps$ + " "
INPUT #8, echo$ PRINT #8, "1j1 2j1 "
CLOSE #8
DO: LOOP UNTIL INKEY$ <> ""
'end of dead code coarsefocus:
'scan through peak
delaytime = .2
GOSUB delay
vmax = -1
PRINT #8, "1fsa0 1fsb0 1fsc0 1v.2 1d25 "
INPUT #8, echo$
DO
   PRINT #8, "1g "
   INPUT #8, echo$
   GOSUB waitloop1
   sum = 0
   FOR i% = 1 TO 100
      CALL cio16(md%, VARPTR(d%(0)), F%)      'read voltage
      sum = sum + d%(0)
   NEXT
   'PRINT sum;
   'time = TIMER
   'DO: LOOP UNTIL TIMER > time + .1
   IF sum > vmax THEN vmax = sum
LOOP WHILE sum + 500 > vmax
PRINT #8, "1g "
INPUT #8, echo$
GOSUB waitloop1
RETURN findfocus:
'set A/D board multiplexer to channel 7
md% = 1
d%(0) = 7
d%(1) = 7
CALL cio16(md%, VARPTR(d%(0)), F%)
md% = 3
OUT 779, 3    '-625 to 625 mV
'find surface 1
GOSUB coarsefocus
'find surface 2 if necessary
IF surface$ = "2" THEN
   PRINT #8, "1d" + LTRIM$(STR$(INT(glassthickness% * 2.14))) +
" 1g "
   INPUT #8, echo$
   GOSUB waitloop1
   GOSUB coarsefocus
END IF
GOSUB delay
'scan back through focus in 1 micron steps
```

```
PRINT #8, "1d-5 "
INPUT #8, echo$
vmax = -1
nstep = 0
DO
   PRINT #8, "1g "
   INPUT #8, echo$
   GOSUB waitloop1
   nstep = nstep + 1
   voltsum = 0
   FOR k% = 1 TO 100
      CALL cio16(md%, VARPTR(d%(0)), F%)
      voltsum = voltsum + d%(0)
   NEXT k%
   IF voltsum > vmax THEN
      vmax = voltsum
      npeak = nstep
   END IF
   volt(nstep) = voltsum
   GOSUB read1
   encoder(nstep) = VAL(a$)
LOOP WHILE voltsum + 500 > vmax
GOSUB read1
posnow = VAL(a$)
GOSUB fitparabola
RETURN fitparabola:
xsum# = 0
ysum# = 0
xysum# = 0
x2sum# = 0
x2ysum# = 0
x3sum# = 0
x4sum# = 0
numpoints = 2 * (nstep - npeak) + 1
PRINT
FOR n = nstep - numpoints + 1 TO nstep
   y = volt(n)
   PRINT n, y
   xsum# = xsum# + n
   ysum# = ysum# + y
   xysum# = xysum# + n * y
   x2sum# = x2sum# + n * n
   x2ysum# = x2ysum# + n * n * y
   x3sum# = x3sum# + n * n * n
   x4sum# = x4sum# + n * n * n * n
NEXT
factor# = x3sum# - x2sum# * xsum# / numpoints
denom# = x2sum# - xsum# * xsum# / numpoints
quotient# = (xysum# - xsum# * ysum# / numpoints) / denom#
quotient2# = factor# / denom#
anum# = x2ysum# - x3sum# * quotient# - x2sum# / numpoints *
(ysum# - xsum# * quotient#)
adenom# = x4sum# - x3sum# * quotient2# + x2sum# / numpoints *
(xsum# * quotient2# - x2sum#)
```

```
a# = anum# / adenom#
b# = (xysum# - a# * factor# - xsum# * ysum# / numpoints) / denom#
x0 = -b# / 2 / a#
focus = encoder(INT(x0 + .5)) + focusoffset * focusfactor
PRINT "x0="; x0, "focus="; focus / focusfactor;
IF scannumber% = 1 THEN
   IF x0 < 10 THEN
      PRINT
      PRINT
      PRINT "Autofocus error:   x0 < 10."
      PRINT "c = continue anyway, t = try again, s = stop."
      DO: LOOP UNTIL INKEY$ = ""
      DO
         INPUT "c, t, or s"; a$
         a$ = LCASE$(a$)
         IF a$ <> "c" AND a$ <> "t" AND a$ <> "s" THEN PRINT "Enter
a single character, either c or t or s."
      LOOP UNTIL a$ = "c" OR a$ = "t" OR a$ = "s"
      IF a$ = "s" THEN
         CLOSE #2
         CLOSE #4
         CLOSE #8
         GOTO start
      ELSEIF a$ = "t" THEN
         IF surface$ = "1" THEN
         PRINT #8, "1v10 1d-1000 1g "
         INPUT #8, echo$
         ELSE
         PRINT #8, "1v10 1d-3000 1g "
         INPUT #8, echo$
         END IF
         SLEEP 1
         GOTO findfocus
      END IF
   END IF
   IF focus > focusmax THEN focusmax = focus
   IF focus < focusmin THEN focusmin = focus
   focusrange = focusmax - focusmin
   IF focusrange / focusfactor > misfocusthreshold THEN
      PRINT
      PRINT
      IF focusrange < 100 THEN PRINT "Possible a"; ELSE PRINT "A";
      PRINT "utofocus error.  Focus positions vary by"; focusrange
/ focusfactor; "microns."
      DO: LOOP UNTIL INKEY$ = ""
      DO
         INPUT "Continue anyway (y or n)"; a$
         a$ = LCASE$(a$)
         IF a$ <> "y" AND a$ <> "n" THEN PRINT "Enter a single
character, either y for yes or n for no."
      LOOP UNTIL a$ = "y" OR a$ = "n"
      IF a$ = "y" THEN
         misfocusthreshold = focusrange / focusfactor
      ELSE
         CLOSE #2
         CLOSE #4
```

```
        CLOSE #8
        GOTO start
      END IF
    END IF
END IF
RETURN waitloop1:
'wait for stage to stop moving
DO
   r$ = SPACE$(10)
   PRINT #8, "1r "
   GOSUB readr
LOOP UNTIL INSTR(r$, "1r *R") > 0
RETURN waitloop3:
DO
   r$ = SPACE$(10)
   PRINT #8, "3r "
   GOSUB readr
LOOP UNTIL INSTR(r$, "3r *R") > 0
RETURN waitloop2:
DO
   r$ = SPACE$(10)
   PRINT #8, "2r "
   GOSUB readr
LOOP UNTIL INSTR(r$, "2r *R") > 0
RETURN readr:
INPUT #8, r$, junk$
'DO
'   nchars% = LOC(8)
'   FOR i = 1 TO ncycles%: NEXT    '5 msec delay
'LOOP UNTIL LOC(8) = nchars% AND nchars% > 0
'r$ = INPUT$(LOC(8), 8)
RETURN read1:
PRINT #8, "1x4 "
INPUT #8, echo$, a$
RETURN read3:
b$ = SPACE$(20)
PRINT #8, "3x4 "
INPUT #8, echo$, b$
RETURN errorhandler:
IF ERR = 76 THEN
   DO
      INPUT "subdirectory does not exist - create it (y or n)"; a$
```

```
      a$ = LCASE$(a$)
      IF a$ <> "y" AND a$ <> "n" THEN PRINT "enter a single
character, either y for yes or n for no"
      LOOP UNTIL a$ = "y" OR a$ = "n"
      IF a$ = "y" THEN
         MKDIR "c:\linescan\data\" + subdir$
         OPEN "c:\linescan\subdir.lst" FOR APPEND AS #1
         PRINT #1, subdir$
         CLOSE #1
         CHDIR "c:\linescan\data\" + subdir$
         RESUME NEXT
      ELSE RESUME asksubdir
      END IF
   ELSEIF ERR = 53 THEN
      PRINT "none"
      RESUME NEXT
   ELSE ON ERROR GOTO 0
   END IF shortdelay:
time = TIMER
DO
   IF TIMER < time THEN time = time - 86400
LOOP UNTIL TIMER > time + .1
RETURN delay:
time = TIMER
DO
   IF TIMER < time THEN time = time - 86400
LOOP UNTIL TIMER > time + delaytime
RETURN emergencystop:
PRINT #8, "s "
INPUT #8, echo$
KEY(1) OFF
PRINT
DO: LOOP UNTIL INKEY$ = ""
PRINT "Scan interrupted by user.  Press any key to return to
menu.";
DO: LOOP WHILE INKEY$ = ""
PRINT
IF logfile$ = "c:\linescan\linescn.log" THEN
   OPEN logfile$ FOR APPEND AS #3
   PRINT #3, "scan interrupted by user at "; TIME$
   CLOSE #3
END IF
CLOSE #2
CLOSE #4
CLOSE #8
SHELL "copy d:tempfile.dat c:" + nfilename$ + " >d:junk"
SHELL "del d:tempfile.dat"
RETURN start printbathstrings:
```

```
   LOCATE 4, 1
   PRINT "initial temperature (degrees C):"; tstart%
   PRINT "number of scans at initial temperature:"; nscansinit%
   PRINT "temperature step (degrees C):"; tstep%
   IF bath$ = "y" THEN
      COLOR 6
      LOCATE 4, 1
      PRINT "i"
      LOCATE 5, 3
      PRINT "m"
      LOCATE 6, 2
      PRINT "e"
      COLOR 7
   END IF
RETURN powermeasure:
'find laser power
sum = 0
FOR i% = 1 TO 100
   'status = AI.VRead(1, 0, 20, voltage#)
   sum = sum + voltage#
NEXT
power% = INT(sum * 10 * powerfactor + .5)
gain% = 100
IF power% > 15 THEN gain% = 50
IF power% > 30 THEN gain% = 20
FOR i% = 1 TO 100
   'status = AI.VRead(1, 1, gain%, voltage#)
NEXT i%

'find noise
max = -1
min = 1
FOR i% = 1 TO 100
   'status = AI.VRead(1, 1, gain%, voltage#)
   IF voltage# > max THEN max = voltage#
   IF voltage# < min THEN min = voltage#
NEXT i%
noise = max - min
IF noise < .0001 THEN noise = .0001
RETURN takedata:
OPEN "d:tempfile.dat" FOR BINARY AS #2
a$ = " "
PUT #2, 512, a$
OPEN "c:\das16jr\dark" + LTRIM$(RTRIM$(STR$(INT(1 / speed + .01)))) + LTRIM$(RTRIM$(STR$(pixelsize%))) + "a.dat" FOR BINARY AS #3
FOR i% = 1 TO 1024
GET #3, , a%
dark%(i%) = a%
NEXT
CLOSE #3
```

```
ave% = 1000
sum& = 0 lowclip& = 0
highclip& = 0
OPEN logfile$ FOR APPEND AS #3
scanstarttime = TIMER
PRINT #3, "starting scan at "; TIME$
CLOSE #3
PRINT #8, "2g 1g "
FOR j% = 1 TO rows%
  max% = 0
  min% = 9999
  jj% = j% MOD 928
  IF pixelsize% = 28 THEN jj% = j% MOD 464
  jj2% = jj% \ 2 md% = 7                              'DISABLE DMA
  CALL cio16(md%, VARPTR(d%(0)), F%)

d%(0) = 1040            'TOTAL # OF CONVERSIONS
  d%(1) = VARSEG(rawdat%(0))   'QUICK BASIC SETS DATA SEGMENT
  d%(2) = 0               '1 = INTERNAL TIMER
  d%(3) = 0               '0 = ONE PASS OF 'N' CONVERSIONS
  md% = 6                 'DMA DRIVEN A/D CONVERSIONS
  CALL cio16(md%, VARPTR(d%(0)), F%)
  IF F% <> 0 THEN PRINT "ERROR IN DMA MODE = "; F%: SLEEP 10:
STOP md% = 13
  d%(0) = 9
  CALL cio16(md%, VARPTR(d%(0)), F%)

md% = 8
  DO
    CALL cio16(md%, VARPTR(d%(0)), F%)
  LOOP UNTIL d%(2) = 1040 md% = 13
  d%(0) = 0
  CALL cio16(md%, VARPTR(d%(0)), F%)

d%(0) = 1040                        ' # OF CONVERSIONS TO RETRIEVE
  d%(1) = VARSEG(rawdat%(0))          ' DATA SEGMENT WHERE ARRAY IS
  d%(2) = 0                           ' BEGIN WITH FIRST CONVERSION
  d%(3) = VARPTR(dat%(-15))           ' DATA SEG. OF DAT%(*) ARRAY
  d%(4) = VARPTR(ch%(0))              ' DATA SEG. OF CHAN%(*) ARRAY
  md% = 9
  CALL cio16(md%, VARPTR(d%(0)), F%)
  IF F% <> 0 THEN PRINT "MODE 9 TRANSFER ERROR # "; F%: SLEEP 10:
STOP
```

```
FOR i% = 1 TO 512
  SWAP dat%(i%), dat%(1024 - i%)
NEXT
linesum& = 0
DEF SEG = VARSEG(dataline$)
address% = SADD(dataline$) - 2
SELECT CASE pixelsize%
CASE 14
  FOR i% = 1 TO 1024
    IF dat%(i%) = 4095 THEN highclip& = highclip& + 1
    dat%(i%) = dat%(i%) - dark%(i%)
    a% = dat%(i%)
    IF a% < 0 THEN
    a% = 0
    lowclip& = lowclip& + 1
    END IF
    IF a% > max% THEN max% = a%
    IF a% < min% THEN min% = a%
    linesum& = linesum& + a%
    POKE address% + 2 * i%, PEEK(VARPTR(a%))
    POKE address% + 2 * i% + 1, PEEK(VARPTR(a%) + 1)
  NEXT i%
  IF 2 * jj2% = jj% THEN
    FOR i% = 2 TO 512 STEP 2
    color1% = dat%(i%) * 5 \ ave%
    IF color1% > 15 THEN color1% = 15
    PSET (i% \ 2, jj2%), color1%
    NEXT
  ELSE
    jj2% = jj2% + 1
    FOR i% = 514 TO 1024 STEP 2
    color1% = dat%(i%) * 5 \ ave%
    IF color1% > 15 THEN color1% = 15
    PSET (i% \ 2, jj2%), color1%
    NEXT
  END IF
  'MID$(dataline$, 2 * i% - 1, 1) = CHR$(a% MOD 256)
  'MID$(dataline$, 2 * i%, 1) = CHR$(a% \ 256)
CASE 28
  FOR i% = 2 TO 1024 STEP 2
    a% = dat%(i% - 1) + dat%(i%)
    IF dat%(i% - 1) = 4095 OR dat%(i%) = 4095 THEN highclip& = highclip& + 1
    a% = a% - dark%(i%)
    IF a% < 0 THEN
    a% = 0
    lowclip& = lowclip& + 1
    END IF
    IF a% > max% THEN max% = a%
    IF a% < min% THEN min% = a%
    linesum& = linesum& + a%
    POKE address% + i%, PEEK(VARPTR(a%))
    POKE address% + i% + 1, PEEK(VARPTR(a%) + 1)
    color1% = 5& * a% \ ave%
    IF color1% > 15 THEN color1% = 15
    PSET (i% \ 2, jj%), color1%
```

```
      NEXT
    CASE 42
      FOR i% = 3 TO 1023 STEP 3
        a% = dat%(i% - 2) + dat%(i% - 1) + dat%(i)
        IF dat%(i% - 2) = 4095 OR dat%(i% - 1) = 4095 OR dat%(i%)
= 4095 THEN highclip& = highclip& + 1
        a% = a% - dark%(i%)
        IF a% < 0 THEN
      a% = 0
      lowclip& = lowclip& + 1
        END IF
        IF a% > max% THEN max% = a%
        IF a% < min% THEN min% = a%
        linesum& = linesum& + a%
        i23% = (i% * 2) \ 3
        POKE address% + i23%, PEEK(VARPTR(a%))
        POKE address% + i23% + 1, PEEK(VARPTR(a%) + 1)
        color1% = 5& * a% \ ave%
        IF color1% > 15 THEN color1% = 15
        PSET (i% \ 3, jj%), color1%
      NEXT
    CASE 56
      FOR i% = 4 TO 1024 STEP 4
        a% = dat%(i% - 3) + dat%(i% - 2) + dat%(i% - 1) + dat%(i)
        IF dat%(i% - 3) = 4095 OR dat%(i% - 2) = 4095 OR dat%(i%
- 1) = 4095 OR dat%(i%) = 4095 THEN highclip& = highclip& + 1
        a% = a% - dark%(i%)
        IF a% < 0 THEN
      a% = 0
      lowclip& = lowclip& + 1
        END IF
        IF a% > max% THEN max% = a%
        IF a% < min% THEN min% = a%
        linesum& = linesum& + a%
        POKE address% + i% \ 2, PEEK(VARPTR(a%))
        POKE address% + i% \ 2 + 1, PEEK(VARPTR(a%) + 1)
        color1% = 5& * a% \ ave%
        IF color1% > 15 THEN color1% = 15
        PSET (i% \ 4, jj%), color1%
      NEXT
    END SELECT
    sum& = sum& + linesum&
    lineave = linesum& / cols%
    ave% = sum& \ cols% \ j% + 1
    PRINT
    PRINT USING "####    ##### max    ##### min    #####.# line ave
scan ave                  ##"; j%; max%; min%; lineave;
ave%; scannumber%;
    PUT #2, , dataline$
NEXT j%
OPEN logfile$ FOR APPEND AS #3
PRINT #3, "done with scan at "; TIME$
PRINT #3, highclip&; "pixels clipped high,"; lowclip&; "pixels
clipped low"
CLOSE #3
INPUT #8, echo$
```

```
CLOSE #2 md% = 7                                      'DISABLE DMA
CALL cio16(md%, VARPTR(d%(0)), F%)
RETURN
```

APPENDIX II

SLIT SCAN

SLITSCAN SOURCE LISTING

```
REM  A program to acquire and rapidly write multiple
REM  frames of data to disk, moving PPL
REM  stepper motor on 1 axis in between reads.

rem  Receive and parse the number
rem  of steps and stepper motor step size.
rem  (1 um/step in closed loop, 0.2 um in open loop).

int ctr
int  numstep
long stepdist
let numstep = 256
let stepdist = 50
inp numstep,stepdist rem  Convert microns to steps for open loop mode.

let stepdist = 5*stepdist long left
int stepdig(8)

let ctr = 8
let left = 0
while ctr > 0
        let stepdig(ctr) = (stepdist-left)/power(10,ctr-1)
       let left = left + stepdig(ctr)*power(10,ctr-1)
      let ctr = ctr-1
wend REM  Initialize serial port & PPL motion controller let tmp = SERIALINIT(1, 9600, 0, 8,1)

let tmp = COMSEND(1,"e")
       let tmp = COMSEND(1," ")

let tmp = COMSEND(1,"m")
       let tmp = COMSEND(1,"n")
       let tmp = COMSEND(1," ")

let tmp = COMSEND(1,"j")
       let tmp = COMSEND(1,"0")
       let tmp = COMSEND(1," ")
```

```
rem  Set up accel (turns/sec^2) & vel. values (turns/sec).
rem  Any value from 1 - 50 and 1 - 10, respectively,
rem  is acceptable.

let tmp = COMSEND(1,"a")
     let tmp = COMSEND(1,"1")
     let tmp = COMSEND(1," ")

let tmp = COMSEND(1,"v")
     let tmp = COMSEND(1,"1")
     let tmp = COMSEND(1," ")

rem  Set up step distance.

let tmp = COMSEND(1,"d")
      let tmp = COMSEND(1,stepdig(8)+48)
      let tmp = COMSEND(1,stepdig(7)+48)
      let tmp = COMSEND(1,stepdig(6)+48)
      let tmp = COMSEND(1,stepdig(5)+48)
      let tmp = COMSEND(1,stepdig(4)+48)
      let tmp = COMSEND(1,stepdig(3)+48)
      let tmp = COMSEND(1,stepdig(2)+48)
      let tmp = COMSEND(1,stepdig(1)+48)
     let tmp = COMSEND(1," ")

rem   INITIALIZE ARRAYS, etc int a
let a = 0
int xprog
int yprog int fastread
int proglines
int progstrips let rundone =
GETPROGXY(xprog,yprog,fastread,proglines,progstrips)

unint image(yprog,xprog)
float imflot(yprog,xprog)
float bkflot(yprog,xprog)

rem  If we are in auto backgd subtraction mode, read
rem  it from disk.
let backsup = GETPIV AR(97)
if backsub = 1 then
        int backfile
        let tmp - GETASCII(25,backfile)
         open backfile for input as 2
         unint bkg(yprog,xprog)
        read 2, bkg
         if header(2,7) = 0 then
             let bkg = UNSCRAMBLE(bkg)
        endif
```

```
close 2
endif rem BEGIN DATA ACQUISITION int outfilenum
let outfilenum = 1
open EXPNAME for output as outfilenum
print "                        ",0,0,0,11

FOR framectr = 1 to numstep
      print "Collecting data" ,0,0,0,11
      print framectr
     let tmp = INIT1FRAME
     let tmp = START130
    let a = WAIT1FRAME
    if a = 1 then
           let tmp = STOP130
           let tmp = GETFULLFRAME(image)
            if backsub = 1 then
                   let imflot = image
                   let bkflot = bkg
                    let imflot = ABS(imflot - bkflot)
                   let image = imflot
           endif
             let tmp = WRITEFRAME(outfilenum,image)
     endif rem   Move stepper motor.
     let tmp = COMSEND(1,"g")
     let tmp = COMSEND(1," ")

NEXT framectr rem WRITE HEADER INFO rem   Image written as unsigned integer data:
let a = SETHEADER(outfilenum,3,3)

Rem   Store # of x points:
let a = SETHEADER(outfilenum,4,xprog)

float totalstrips
let totalstrips = (1.0*yprog)*(1.0*numstep)
let a = SETHEADER(outfilenum,5,totalstrips)

Rem   Store # of y points:
let a = SETHEADER(outfilenum,6,yprog)

Rem   Image scrambled before storage:
let a = SETHEADER(outfilenum,7,1)

close outfilenum

REM Return stepper to starting position long dist
let dist = numstep*stepdist+1000
let ctr = 6
```

```
let left = 0 while ctr > 0
        let stepdig(ctr) = (dist-left)/power(10,ctr-1)
        let left = left + stepdig(ctr)*power(10,ctr-1)
        let ctr = ctr-1
wend let tmp = COMSEND(1,"d")
let tmp = COMSEND(1,"-")
let tmp = COMSEND(1,stepdig(8)+48)
let tmp = COMSEND(1,stepdig(7)+48)
let tmp = COMSEND(1,stepdig(6)+48)
let tmp = COMSEND(1,stepdig(5)+48)
let tmp = COMSEND(1,stepdig(4)+48)
let tmp = COMSEND(1,stepdig(3)+48)
let tmp = COMSEND(1,stepdig(2)+48)
let tmp = COMSEND(1,stepdig(1)+48)
let tmp = COMSEND(1," ")

let tmp = COMSEND(1,"g")
let tmp = COMSEND(1," ")

let tmp = COMSEND(1,"d")
let tmp = COMSEND(1,"1")
let tmp = COMSEND(1,"0")
let tmp = COMSEND(1,"0")
let tmp = COMSEND(1,"0")
let tmp = COMSEND(1," ")

let tmp = COMSEND(1,"g")
let tmp = COMSEND(1," ")

print"                           ",0,0,0,11
print "Data acquisition complete",0,0,0,11
```

APPENDIX III

SPECTRAL ANALYSIS

```c
/*==============================================================
SPECTRA.C */
/*
Copyright (c) 1987-1992 by Automated Visual Inspection. All
rights reserved.
*/
#include <stdio.h>
#include <string.h>
#include <dos.h>
#include <stdio.h>/**/
#include <alloc.h>
#include "fb.h"
#include "fkeys.h"

#include "ACCULIB.H"
#include "ACCULIB2.H"
#include "ACCULIB3.H"
#include "affy.h"

#define PI 3.141592654
define DEGRAD 57.296 /* Convert radians to degrees */ extern int maxcineframes, ncineframes, useallmemory;
extern int newcinecols, newcinerows, cinecols, cinerows,
*cine_imlist;
extern char PRDsuffix[];

void framecompare1(int *, int, int);
void test(), readspectfile(), cineprofile(), spectplot();
void display_seq(), readcelfile();
int spectransform();
char bdlistname[40] = "am"; /* Command name for bd list */
char bdlistexplan[60] = "Affymetrix functions"; /* Explanation
for bd list */
struct optlist bdlist[] = {
    {"sequence","Display sequence",(int *)display_seq,'*',0,0},
    {"readcel","Read a CEL file",(int *)readcelfile,'*',0,0},
    {"PRDsuffix","PRD   /   Sequence   file   extension",(int
*)PRDsuffix,'w',-4,0},
    {"profile","create profile image",(int *)cineprofile,'*',0,0},
    {"read-SPE","Read SPE file",(int *)readspectfile,'*',0,0},
    {"transform","Perform color transformation on 4 frames",(int
*)spectransform,'*',0,0},
    {"plot","Plot   the   spectra   at   given   points",(int
*)spectplot,'*',0,0},
     {"writecelfile","Write   binary   cel   file",(int
*)writebincelfile,'*',0,0},
    {(char *)-1,0,(int *)0,0,0,0}
};

#define MAXPLANES 128 /* Maximum allowed spectral planes */
#define SCALE 64     /* Scale factor to convert float to int */
/***********************************************************
spectransform */
/* Given the frame numbers, and coefficients, compute new frames
*/
```

```c
int spectransform(){
   FILE *fp;
   int ncoeff = 4, nresults = 4, *src;
   int i, c, r, y;
   int flist[MAXPLANES];
   register int x, factor;
   char paramfile[81] = "transfrm.dat";
   char buf[MAXCOLS], *ptr;
   long *lbuf;
   double *coeff[ MAXPLANES ], *cbuf;

/* Get set up info */
   fbgetword(paramfile,-80,"Coefficient file name");
   /* Open file, malloc buffers, read data */
   fp = fopen(paramfile,"rt");
   if( !fp ){
      seterror(FILE_DIDNT_OPEN,paramfile);
      return 0;
   } do { fgets(buf,80,fp); } while( *buf==';');
   sscanf(buf, "%d %d\n", &nresults, &ncoeff);

src = malloc(sizeof(int) * nresults );
   cbuf = malloc(sizeof(double) * ncoeff * nresults );
   lbuf = malloc(sizeof( long ) * cinecols );
   if( malloctest(lbuf,"spectransform") ) return 0;
   for( i = 0; i < nresults; i++ ){
      coeff[i] = &cbuf[i*ncoeff];
   } do { fgets(buf,80,fp); } while( *buf==';');
   ptr = strtok( buf, " \t," );
   for( c = 0; c < ncoeff; c++ ){
      src[c] = atoi(ptr);
      ptr = strtok( NULL, " \t," );
   }
   for( i = 0; i < nresults; i++ ){
      do { fgets(buf,80,fp); } while( *buf==';');
      ptr = strtok( buf, " \t," );
      for( c = 0; ptr && c < ncoeff; c++){
         coeff[i][c] = atof(ptr);
         ptr = strtok( NULL, " \t," );
      }
   }
#if 0
   for( i = 0; i < nresults; i++ ){
      do { fgets(buf,80,fp); } while( *buf==';');
      ptr = strtok( buf, " \t," );
      src[i] = atoi(ptr);
      ptr = strtok( NULL, " \t," );
      coeff[i] = &cbuf[i*ncoeff];
      for( c = 0; ptr && c < ncoeff; c++){
         coeff[i][c] = atof(ptr);
         ptr = strtok( NULL, " \t," );
      }
```

```
        }
#endif
        /* PRINT OUT COEFFICIENTS */
        for( c = 0; c < ncoeff; c++ ){
            printf( "\nSource plane %3d: ", src[c]);
            for( i = 0; i < nresults; i++){
                printf( "%5.2f", coeff[i][c] );
            }
        }
        /* perform image processing */

/* For each result image */
        for(r = 0; r < nresults; r++){

/* For each row */
            for( y = 0; y < cinerows && geterror(NULL,0)==0; y++ ){

/* Add each coefficient row */
                memset( lbuf, 0, sizeof( long ) * cinecols);
                for( c = 0; c < ncoeff; c++ ){
                    fgetrow(0, y, buf, cinecols, cine_imlist[src[c]] );
                    factor = coeff[r][c] * SCALE;
                    for( x = 0; x < cinecols; x++ ) lbuf[x] += buf[x] *
factor;
                }
                factor = factor * ncoeff;
                for( x  =  0;  x  <  cinecols;  x++  )  buf[x]  =
(*pixclip)(lbuf[x] / factor);
                fputrow(0, y, buf, cinecols, r+1 );
                putrow( 0, y, buf, cinecols); /* for progress monitor
*/
            }
        } free( src );
        free( coeff );
        free( lbuf );
        errorprintf("Results are in frames starting at #2");
        setwindowroi(0, 0, cinecols, cinerows );
        for( i = 0; i < nresults; i++) flist[i] = i+1;
        framecompare1( flist, nresults, 1 );
        return 1;
}

/********************************************************
cineprofile */
/* plot the profile of a row in the cine space */
void cineprofile(){
    int rownum = cinerows/2;
    char buf[MAXCOLS];
    int ulx = (NCOLS-cinecols) / 2;
    int uly = (NROWS-cinerows) / 2;
    int i;
    if( ncineframes==0 ){
        errorprintf("No images in memory yet. Use cine-acquire or
```

```
bd-spectra\n");
        return;
    }
    setwindowroi(ulx, uly, ulx+cinecols-1, uly+ncineframes);
    while( 1 ) {
        fbgetint(&rownum, -1, cinerows-1, "Row number (-1 to quit)");
        if( rownum<0 ) break;
        erase(30);
        for( i = 0; i < ncineframes; i++ ){
            fgetrow(0, rownum, buf, cinecols, cine_imlist[i]);
            putrow(ulx, uly+i, buf, cinecols);
        }
    }
}
int displayframe = 25;
static int boxsizex = 5, boxsizey = 5, dispdx, dispdy;
static int scalefactor = 1, nsum;
/*******************************************************
getspectrum */
getspectrum(int xorg, int yorg, char *buf ){
    int i, y, hx = boxsizex/2, hy = boxsizey/2;
    int total = boxsizex*boxsizey;
    register int x, isum;
    char rowbuf[MAXPLANES];
    for(i = 0; i < ncineframes; i++){
        isum = 0;
        for( y = 0; y<boxsizey; y++){
            fgetrow(xorg-hx,   yorg-hy+y,   rowbuf,   boxsizex,
cine_imlist[i]);
            for( x = 0; x < boxsizex; x++ ) isum += rowbuf[x];
        }
        buf[i] = isum * scalefactor / total;
    }
}

/*******************************************************
checkspect */
/* Do real time spectrum measurment */
void checkspect(int x, int y, int none){
    char buf[MAXPLANES];
    int maxval, hmax, maxi, i, first, last;
    x -= dispdx; y -= dispdy;
    if( x<0 || y<0 || x>=cinecols||y>=cinerows) {
        maxval = maxi = last = first = 0;
    }
    else {
        getspectrum( x, y, buf );
        for( i = maxval = 0; i< ncineframes; i++){
            if( buf[i] >= maxval ) { maxi = i; maxval = buf[i];}
        }
        hmax = maxval/2;
        for( i = 0; i< ncineframes && buf[i]<hmax ; i++);
        first = i;
        for( i = ncineframes-1; i<0 && buf[i]<hmax ; i--);
        last = i;
```

```c
    }
    gotoxy(1,1);
    printf("Max: %3d at plane %3d, FWHM=%2d    boxsize=%d,%d scale=%d N-sums=%d",
        maxval/scalefactor, maxi, last-first, boxsizex, boxsizey, scalefactor, nsum);
    abs(none);
}
/**************************************************************
rectcursor */
/* Rectangle cursor defined by boxsize */
static void rectcursor(int x, int y, int up ){
    int ulx, uly;
    ulx = x-boxsizex/2;
    uly = y-boxsizey/2;
    abs(up);
    drawbox(ulx, uly, ulx+boxsizex, uly+boxsizey, -1 );
}

/********************************************************** spectplot
*/
/* Plot the spectrum at a given point */
void spectplot(){
    FILE *fp = 0;
    int i, oldctype = cursortype;
    int x, y;
    int autoscale = 0;
    int plotgrid = TRUE;
    int plotcolor = I_RED;
    int textcolor = I_RED-1; /* This gray-white allows inversion
*/
    char c, cbuf[MAXPLANES];
    char excelname[80] = "";
    long *lbuf = malloc( ncineframes * sizeof(long) );

nsum = 0;
    dispdx = 0;
    dispdy = charsize.y*3;
    erase(I_WHITE); /* X */
    displayframe = ncineframes/2;
    getint(&displayframe,0,ncineframes-1,"Image to display");
    setroitype( FULLFRAME_ROI );
    roicopy( cine_imlist[displayframe], framenum, dispdx, dispdy);

replot:
    setupgraph(cinecols, ulmargin.y + charsize.y*2, lrmargin.x, lrmargin.y*2/3,
        0 /*128*/,textcolor,"Spectra"); /* X */
            scalegraphL( NULL ,
0,0.,ncineframes,intensitycal(0.),intensitycal(NLEVELS-1));
    graphxaxis("plane",plotgrid,1);
    graphyaxis("Intensity",plotgrid,1);
    buttonhelp( "Add profile", "Clear plot", "Save to Excel file");
    gotoxy(1,2);
    printf("a: toggle auto-scale; b: set box size; c: color f:
```

```
        scale-factor\n");
           printf("s: sum this to next plot\n");
           while( 1 ) {
               extern void (*cursorfcn)(int x, int y, int up);
/*             cursortype = 1;/**/
               cursortype = 2;
               cursorfcn = rectcursor;
               c = movecursor(checkspect);/**/ cursortype = oldctype;
               if( c >2 && c < 8) goto replot;
               if(c=='a') autoscale = !autoscale;
               if(c=='b') {
#if 0
               w0.x = p0.x -dispdx - boxsizex/2;
               w0.y = p0.y -dispdy - boxsizey/2;
               w1.x = w0.x + boxsizex-1;
               w1.y = w0.y + boxsizey-1;
               c = wmov();
               boxsizex = w1.x+1-w0.x;
               boxsizey = w1.y+1-w0.y;
#else
               fbgetint(&boxsizex, 0, 0, "averaging box size(x)");
               fbgetint(&boxsizey, 0, 0, "averaging box size(y)");
#endif
               }
               if(c=='c') {
                   if( plotcolor==0 ) plotcolor = I_WHITE;
                   plotcolor++;
/*                 if( plotcolor==I_WHITE) plotcolor = 0;/* X */
               }
               if(c=='f') fbgetint(&scalefactor, 0, 0, "scale factor");
               if( scalefactor < 1) scalefactor = 1;
               if( boxsizex < 1) boxsizex = 1;
               if( boxsizey < 1) boxsizey = 1;
               if( plotcolor >= NLEVELS ) plotcolor = maxgray+1;
               if(c=='x' || c=='^[' || (c>8 && c<32)) break;
               x = MIN( p0.x - dispdx, cinecols);
               y = MIN( p0.y - dispdy, cinerows);

getspectrum( x, y, cbuf );
               if( nsum ) for(i = 0; i < ncineframes; i++) lbuf[i] +=
cbuf[i];
               else for(i = 0; i < ncineframes; i++) lbuf[i] = cbuf[i];
               if( c=='s'){
                   nsum++;
                   continue;
               }
               if( nsum ) for(i = 0; i < ncineframes; i++) lbuf[i] /=
(nsum+1);
               nsum = 0;

scalegraphL(lbuf, ncineframes,0.,0.,0.,autoscale?0:255.);
               grapharrayL(lbuf, ncineframes,plotcolor, PT_CONNECT);/**/
               if( c == 2 ){ /* WRITE EXCEL FILE */
                   fbgetword(excelname,-80,"Excel file name");
```

```c
        fp = fopen(excelname,"at");
        if( fp ) {
            for(i=0;i<ncineframes;  i++)   fprintf(fp,   "%d\n",
cbuf[i]);
            fclose( fp );
            fp = 0;
        }
        else {
            if(  *excelname)  errorprintf("File  %s  didn't
open",excelname);
        }
    }
    free( lbuf );
} define HEADLEN 4100
define NOSCAN 34
#define FACCOUNT 42
#define STRIPE 656
#define LNOSCAN 664

/*******************************************************
readspectfile */
/* Read a spectra file into cine images */
void readspectfile(){
    FILE *fp;
    char *bhead = (char *)malloc(HEADLEN);
    long noscan, nstripes;
    int ncols, nrows, nplanes, maxplanes = 13;
    int firstplane = 0, lastplane;
    static int iscale = 4;
    char path[81], name[80], mask[20] = "*.SPE";

/*strcpy(fileprefix,"c:\\temp");/**/ if(!getmousedir(fileprefix,mask,name)   ||   name[0]=='\0')
return;
    sprintf(path,"%s%s",fileprefix,name);
    fp = fopen(path, "rb");
    if (!fp ) printf("Input file %s didn't open\n", path);
    if (!fp || !bhead) return;
    fread( bhead, 1, HEADLEN, fp);
    nstripes = *(int *)(bhead + STRIPE);
    noscan   = *(int *)(bhead + NOSCAN);
    if (noscan == -1) {
        noscan = *(long *)(bhead + LNOSCAN);
    }
    nplanes = *(int *)(bhead + FACCOUNT);
    nrows = noscan / nstripes;
    ncols = nstripes;
    printf("       Input file %s: cols = %d, rows = %d, planes = %d\n",
        path, ncols, nrows, nplanes);
    fbgetint(&iscale,0,0,"Intensity division factor");
    gotoxy(1,1);
```

```
{ /* Read the data, and write it */
    char **obuf, *optr;
    int y, p, *ibuf, *iptr, maxframes;
    unsigned len;
    register int x;

obuf = malloc( nplanes * sizeof( char *));
    ibuf = malloc( nplanes * sizeof( int  ) * ncols );
    if( malloctest(ibuf,"spectra") ) return;

maxplanes = nplanes;
    lastplane = firstplane + maxplanes;
    if( lastplane > nplanes) {
        lastplane = nplanes;
        maxplanes = nplanes - lastplane;
    } cinefreeframes(); /* FREE OLD FRAMES */
    newcinecols = ncols;
    newcinerows = nrows;

/* MAKE SURE WE HAVE ENOUGH MEMORY */
    if( (maxframes = computemaxframes()) < nplanes){
        errorprintf("Only    enough    memory    for    %d frames\n",maxframes);
        lastplane = maxframes;
    }
    useallmemory = 0;
    maxcineframes = lastplane;
    cineallocframes(); /* Allocate as many frames as memory allows */
    ncineframes = lastplane;

for(p = firstplane; p < lastplane; p++) {
        obuf[p] = malloc( ncols );
        if( malloctest(obuf[p],"" )) return;
    }
    lastplane = p;
    printf("\n");

fseek(fp, HEADLEN, 0);

for( y = 0; y < nrows; y++ ){ /* For each input/output row */
        len = fread( ibuf, sizeof(int) * nplanes, ncols, fp );
        if( len != ncols ){
            errorprintf("Failure to read file (len=%d; %d expected)\n",len,ncols);
        }
        for( p = firstplane; p < lastplane; p++ ){ /* For each in-col/out-plane */
            iptr = &ibuf[p];
            optr = obuf[p];
            for( x = 0; x < ncols; x++ ){
                optr[x] = iptr[x*nplanes] / iscale;
            }
```

```c
        if(p==displayframe) putrow( 0, y+charsize.y*2, optr, ncols);
            fputrow( 0, y, optr, ncols, cine_imlist[p] );/**/
        }
        showprogress(y,nrows);
        if( userbreak(1) ) break;
    }
    showprogress(0,0); /* Clear progress monitor */
    for(p = firstplane; p < lastplane; p++) {
        free( obuf[p] );
    }
    free(obuf);
    free(ibuf);
    }
    return;
}

/*==========================================================
ACCULIB.H */
#undef AFFY
#define AFFY       /* AFFYMETRIX  And make this file Read Only...
*/
/*************************************************************
ACCULIB.H */
/* Definitions for ACCUWARE LIBRARY */
/*
        Copyright (c) Automated Visual Inspection 1991, 1992
        All Rights Reserved.
*/
/* 5/9/92  Peter Fiekowsky */ ifndef __ACCULIB
define __ACCULIB include "error.h"
include <math.h>
#ifdef __TURBOC__
#include <alloc.h>
#else
#include <malloc.h>
void *farmalloc( unsigned long );
void farfree( void * );
#endif
include <stdio.h> define LIBRARY
ifndef __TURBOC__
#include "tc-msc.h"
endif define BIGENDIAN 0 /* THIS IS AN INTEL PROCESSOR */
/* #define BIGENDIAN 1 /* THIS IS MOTOROLA OR MIPS */

/* PIXEL VALUE DEFINITIONS */
enum {
I_RED = 252,
I_GREEN,
```

```
    I_BLUE,
    I_WHITE = 255
};
#define WTDWHITE (-3)

define MODE_RGB 3 define MAXLEVELS 256
ifdef __TURBOC__
#define MAXCOLS 2048
#else
#define MAXCOLS 1024
#endif
define MAXROWS 1024 define MAXFRAMES 50

/* IMAGE TYPES */
#define I_FAST 0
#define I_DOS  1
#define I_EMM  2
#define I_XMS  4
#define I_FILE 8
#define I_FRAMEBUFFER 16

/* ROI TYPES */
enum {
    FULLFRAME_ROI = 0,
    WINDOW_ROI,
    POLYGON_ROI,
    SCANLIST_ROI
};

/* getlivecap returns */
enum {
    LIVE_NODIG = -1,
    LIVE_SNAPONLY,
    LIVE_LIVE,
    LIVE_CAPTURE,
};

/* CLIPPING MODES */
enum {
    CLIP_NONE, /* No clipping */
    CLIP_NORM, /* Simple clip between 0,maxgray */
    CLIP_ABS,  /* take abs value of values <0, clip those above
to maxgray */
    CLIP_OFFSET, /* Add NLEVELS/2 and then clip 0..maxgray */
    CLIP_DIV_OFFSET, /* Divide by 2, add NLEVELS/2, then clip
0..maxgray */
    CLIP_SIGNED, /* clip to -128-+127 */
    CLIP_DIV_SIGNED /* clip to -128-+127 */
};
```

```c
/* DEFLICKER MODES */
enum {DEFLICKER_AV = -1, DEFLICKER_EVEN, DEFLICKER_ODD};

/* GRAPHING ROUTINES */
enum pointtypes {
    PT_FILLEDBOX = -5,
    PT_BOX,
    PT_CROSS,
    PT_DOT,
    PT_CONNECT = 0
};

enum filetypes {
FILE_NONE, FILE_TIFF, FILE_RAW, FILE_PAC, FILE_UNKNOWN
};

#define TRUE 1
#define FALSE 0
#define BOOL int
#define ULONG unsigned long
#define UINT unsigned int
#define UCHAR unsigned char
define SCHAR signed char define MAX(a,b)        (((a) > (b)) ? (a) : (b))
define MIN(a,b)        (((a) < (b)) ? (a) : (b))
#define CLIP(a,b,c)       (((a) < (b)) ? (b) : (MIN(a,c)))

#define coord COORD
#define fcoord DCOORD
typedef struct _xy {int x,y;} COORD;
typedef struct _longxy {long lx,ly;} LCOORD; /* long coord */
typedef struct _dblxy {double fx,fy;} DCOORD; /* floating coord
*/

/* ROI DEFINITIONS */
#define MAXPOLYDIM 32 /* This is for data.c only */
#define NPOLYS 20
#define MAXPOLYSIZE 100
#define MAXSCANLIST 3000
define BLOBTABLESIZE 256 typedef struct {
    int newnum;
    long sum,sumi,sumx,sumy;
} blob;
/*extern blob huge *blobtable;*/ if 0
/* GLOBAL VARIABLES */
extern char progpath[]; /* path to directory for finding system
files */
/* Frame buffer Driver */
extern int NCOLS,NROWS,NLEVELS,NFRAMES,framenum, cameranum;
extern int diggain,digoffset, maxdiggain, maxdigoffset;
extern int normdiggain, normdigoffset, genlockmode,interlace;
```

```c
extern int color,bgrndcolor,overlaycolor,colormode;
extern int maxgray, fbtype;
extern double xyratio;
extern int checkcoordsflag;
endif extern char ROIfilename[]; /* Default ROI filename read when ROIs
are initialized */ enum fbtypes {
I_CORTEX1,   /* IMAGENATION CORTEX 1 */
I_CORTEXVGA,/* IMAGENATION CORTEX 1 */
I_DIPIX,    /* Dipix P360 (and P360F) +VGA */
I_DIPIXF,   /* Dipix P360F +VGA */
I_DT2851,   /* Set for Data Translation 2851 */
I_DT2856,   /* Also SB1956. Line Scan board. +VGA */
I_DT2862,   /* Set for Data Translation 2862 */
I_DT2867,   /* Set for Data Translation 2867 */
I_EPIX4M,   /* EPIX 4MEG-Video */
I_EPIXSV,   /* EPIX Silicon Video Mux */
I_FG100,    /* Set for ITI FG100 and VFG100 */
I_HRT,      /* High Res Technologies' HRT 512-8 */
I_IMAGE1280,/* Matrox Image 1280, */
I_IMAGE640, /* Matrox Image 640, */
I_IMAGELC,  /* Matrox Image LC */
I_IP8,      /* Set up for MATROX's IP-8 */
I_ITI,      /* Set for ITI PCVISION */
I_MVP,      /* Matrox MVP */
I_OCULUS,   /* CORECO boards w/ OCULUS DRIVER */
I_OFG100,   /* ITI OFG-100 */
I_PIP,      /* Set up for PIP 1024 or 512 */
I_REDCOLOR,/* Redlake NTSC (color version) */
I_REDLAKE,  /* Redlake NTSC+M (B/W version) */
I_SB4256,   /* EG&G Reticon 4256 high speed camera */
I_SCORPION,/* Univision Scorpion */
I_TARGAP,   /* Set for Truevision TargaPlus */
I_V16,      /* EVEREX VISION 16 */
I_VGA,      /* VGA */
I_VISION8   /* EVEREX VISION 8 */
};

#endif
#ifdef NEWNAMES
#include "accushnm.h"
#endif
#include "accushnm.h"
#include "accuprot.h"
```

```
/*==========================================================
ACCULIB2.H */
/* NAMES USED BY ACCUWARE LIBRARY, BUT HIDDEN FROM APPLICATIONS
*/
#ifndef __ACCULIB2
#define __ACCULIB2
/* #include "prot.h"/* all prototypes */ define textcolor _itextcolor
define textsize  _itextsize

/* MAKE THESE ILLEGAL STRINGS TEMPORARILY 12/27/93 */
#define RED 1x2c3zI_RED
#define GREEN 1x2c3zI_GREEN
#define BLUE 1x2c3zI_BLUE
define WHITE 1x2c3zI_WHITE /* ROI DEFINITIONS */
define MAXPOLYDIM 32
#define NPOLYS 20
#define NKERNELS 1

/* GLOBALS (HIDDEN FROM USERS) */
extern BOOL roiflag,polygonflag,dontmkscanlist;
extern int scanlistlen, polydim;
extern coord polygon[],*scanlist, w0,w1;
extern coord destoffset;
extern coord charsize, textpos;
extern int centertext;
extern UCHAR *_rlut,*_glut,*_blut, *gammalut;
extern int statscolor;
extern int screenprintf;
extern int maximages;
extern int imautoclear;
extern int clipmode;

/* GLOBAL VARIABLES */
extern char progpath[]; /* path to directory for finding system
files */
/* Frame buffer Driver */
extern  int   NCOLS,NROWS,NLEVELS,NFRAMES,framenum,  cameranum,
fbplanar;
extern int overlaydisplay; /* True if overlay plane is being
displayed */
extern int overlaywrite;
extern int graphicsoverlay;
extern int keyingcolor;
extern int mapaftersnap;

extern int diggain,digoffset, maxdiggain, maxdigoffset;
extern int triggermode, triggerlevel;
extern int normdiggain, normdigoffset, genlockmode,interlace;

extern int saturationval, hueval, maxsaturationval, maxhueval;
```

```
extern int normsaturationval, normhueval;

extern int color,bgrndcolor,overlaycolor,colormode;
extern int maxgray, fbtype;
extern double xyratio;
extern int checkcoordsflag;

extern int cinecols, cinerows, cineulx, cineuly, cinesnapflag;

extern void (*SendDispLUT)(UCHAR *, UCHAR *, UCHAR *);

extern int (*hw_drawrect)(int ulx,int uly,int lrx,int lry,int
color,int frame);
extern int (*hw_cursor)(int x, int y, int up, int color, int
length, int frame);
extern int (*hw_drawline)(int x1, int y1, int x2, int y2, int fs,
int fd);
extern int (*hw_histogram)(unsigned long *histogram,int frame);
extern int (*hw_lutmap)(UCHAR *lut,int fs,int fd);
extern int (*hw_convolve)(int kernx,int kerny,int *kernel,int
divisor, int clipmode, int fs, int fd);
extern int (*hw_sobel)(int fs, int fd);
extern int (*hw_median)(int fs, int fd);
extern int (*hw_erode)(int takemin, int fs, int fd);
extern int (*hw_frameavg)(int navg,int frame, double scale);
extern int (*hw_rectcopy)(int sulx, int suly, int fs, int dulx,
int duly, int fd, int cols, int rows);
extern int (*hw_divideimage)(int fs1,int fs2,int fout,int
multscale);
extern int (*hw_2imageop)(int fs1,int fs2,int fout,int oper);
endif void fillicaltable(int *index, float *energy, int nentries);
double intensitycal(double x);
double intensityuncal(double x);
float *geticaltable();
void initcaltable();
int rint(double);

/* DATA STRUCTURE FOR ADDING NEW IMAGE TYPES */
/* IMAGE.C */
typedef struct _imagetype {
   int (*getrow)(int, int, UCHAR *, int),
       (*putrow)(int, int, UCHAR *, int),
       (*getrawrow)(int, int, void *, int),
       (*putrawrow)(int, int, void *, int),
       (*getrawblock)(int, int, int, int, void *),
       (*putrawblock)(int, int, int, int, void *);
   void *(*getptr)(int, int, unsigned *, int *);
   int (*setframe)(void *);
   int (*getconv)(UCHAR *, void *, int ),
       (*putconv)(void *, UCHAR *, int ); /* Convert from/to Raw
pixels */
   int planar;
   long (*alloc)(int); /* Allocate the given frame, return its
```

```
ptr/handle */
    void (*free)(void *); /* Free the pixel memory (fclose(), or
farfree() or extfree() */
    int  (*getsize)(int *cols, int *rows, int *pixbytes,int n);
    int  (*getnframes)(void), nframes;
    int  *openflags; /* When all frames are closed, reset nframes
to 0 */
} IMAGEtype;
```

```
/***********************************************************
ACCULIB3.H */
/* USER INTERFACE VARIABLES AND TYPE DEFS */
#include "3dplot.h"
#include "math.h"
#define LIBRARY
#define textcolor _itextcolor
#define textsize _itextsize
extern int scanlistlen;
extern coord *scanlist;
extern int dontmkscanlist;
struct optlist {
    char *label;      /* Name to call command */
    char *explanation;  /* Explanation, prompt, and keywords for help */
    int *n;           /* Pointer to variable, string, structure, or procedure */
    char type;        /* 'i'nteger, 'f'loat, 's'tring,'*'procedure,
                         'C'oord structure, 'a'rray of int, or 'm'acro */
    int lo,hi;        /* Range limits for int, float; dimensions of array,
                         lo=maxlen of string or lo=macro# for creating file# */
};
typedef struct optlist OPTLIST;
long    dcstr(),  lmin(),lmax(),  lclip(),   rlong(),   labs(),
motposition();
double    fmin(),fmax(),   fclip(),     fcdist(),    fdist(),
funitvect(),unitvect(), coordatan2();
double gettextsize();
double settextsize(double);
char *measureline();
void *malloc(), swapint(int *a, int *b), swapcoord(coord *a,coord *b);
void swapchar(char *a, char *b), swaplong(long *a, long *b),
swapfloat(double *a, double *b);
int move2D(char *prompt, char *fmt, int *xparam, int *yparam,
   int minval, int maxval, int normx, int normy,
   void (*fcn)(int,int), int *factors, int calflag);
void printdata(char *title,char buftype, void *buf,int buflen,int ncols, char *fmt,...);
int errorprintf(char *fmt,...);

extern void (*idleproc)();
extern struct optlist options[];
extern int printtime,pdelay,debug,fromtty;
extern char pstr[];
extern coord normclip;
extern int demoflag;
extern int kernels[][9];
extern int kernelnum;

/* INSPECTION APPLICATION VARIABLES */
extern int displaymode;
```

```
extern fcoord milsppix;
extern double xyratio;
extern char distanceunits[],intensityunits[];
extern int cameranum,sharpfactor,sharpwidth;
extern int equalizemax, smoothzoom;

/* frame buffer variables */
extern char imagefile[];
extern   char   fileprefix[],filesuffix[],   menufilename[],
progpath[], serialroot[];
extern int serialnameflag, serialfilecounter, serialnplaces;
extern int framenum, lastemframe, cameranum;
extern  int  contrast,brightness,  maxcontrast,  maxbrightness,
genlockmode,interlace;
extern int CCIRmode;
extern int color,bgrndcolor,overlaycolor,colormode,brightfeature;
extern int pixelwidth, maxgray;
extern int autobright,autothreshflag, threshline;
extern int sthresh, dthresh[2], threshpcnt;
extern    int    cursorcolor,    cursortype,    activecursor,
polydim,polydims[],polynum;
extern void (*cursorfcn)(int x, int y, int up);
extern int fcsmooth;
extern double gammacrt;
e x t e r n    c o o r d    f w 0 , f w 1 ,    w 0 ,    w 1 ,
p0,p1,polygon[],polys[][MAXPOLYDIM];
extern coord w0s[NPOLYS*2];
extern unsigned long histogram[MAXLEVELS];
extern int histmin,histmax;
extern unsigned char *lut,*_rlut,*_glut,*_blut,*gammalut;
extern int roiflag, polygonflag;
extern int cursorsize, lflashtime;
extern    int    asksd,    mousemacro,    batchmode,
source_dest[2],ssource_dest[3],textscreen;
extern int batchmode;
extern int nundoframes, undoframe, dataprint;

/* Printer variables */
extern char printfile[], printername[];
extern int draftmode, printernum;

extern int menuflag, menulines, menuup,helpup, nopopup;
extern int framewidth, framecolor;
extern coord popuppos;
extern int DefaultChooseItem;
extern coord textpos, textend, ulmargin, lrmargin;
extern double textsize, menusize, labelsize;
extern  int  fbtoo,  textcolor,  textbcolor,  texttype,  centerx,
centertext;
extern char fontname[];
extern coord charsize;
extern int _mousebutton, mbutton, mousefactor;

extern int temp;

extern coord edgeoffset;
```

```c
/* MOUSELIST STRUCTURE: Mouse Menu option list. */
typedef struct {
      char *label; char *explanation; int *n; char type; int lo,hi;
      coord ulc,lrc; int level, color;
} mouselist ;

extern int brightfeature;

extern int lastblob;
extern int bloblevello,bloblevelhi;
extern unsigned int blobarealo,blobareahi;

void printdata(char *title,char buftype, void *buf,int buflen,int ncols,char *fmt,
      ... );

/* CINE PARAMETERS */
extern int cineimagetype, maxcineframes, ncineframes;
extern int cinecols, newcinecols, cinerows, newcinerows;

/* Application-specific option lists */
extern struct optlist bdlist[], bdlist2[];
extern char bdlistname[40],bdlistname2[]; /* Command name for bd list */
extern char bdlistexplan[60],bdlistexplan2[]; /* Explanation for bd list */

/* wmov and other move params */
extern int smoothzoom; /* Smoothing for scalewindow */
extern int mousemacro; /* Take mouse move commands from source input */
                     /* Also used in swzoom, but shouldn't be. */
extern int cmov_addpts; /* Set up cmov mouse buttons for add-points */
extern int wmov_showsize; /* Display position in wmov? */
extern int wmov_constsize; /* Wmov can only move the window. */
extern int wmov_constratio; /* Wmov must keep xyratio constant. */
extern void (*wmovprintf)( char *); /* sprintf formatter for wmov */
```

LANGUAGE: 'C'
Compiler: Borland TurboC 2.0

```c
/*==============================================================
COUNT.C */
/* COUNT CELLS */
#include <string.h>
#include <stdlib.h>
#include <stdio.h>
#include <alloc.h>
#include <math.h>
#include "data.h"
#include "affy.h"
/*#include "accuprot.h"/**/

/* 11/01/93  "fixed" bug where countcells output only 0s when cell cols*rows
            >2048.  Possible Fixes: MAXCOLS=4096, or scancells:
            int    rbuf[3*MAXCOLS],   or   remove   fprintf,   or
x+=..offset, or
            getpeptidestring() call.  Don't know why it started working
            again!

*/
define SHIFT 16 define DEGRAD 57.2958 /* COnversion of degrees to radians */
define AUTOSENSITIVITY 9  /* ratio of largest to smallest peak used */ extern int datimage; /* Handle for 8 or 16 bit .dat image */
extern unsigned int datimagemax; /* Maximum value in raw datimage */
extern char datfilename[];
extern int mbutton;
int rawdata; /* Indicate that datimage is 16, not 8 bits/pixel */
unsigned int rawdatmax = MAXLEVELS-1; /* Maximum value in raw datimage */ extern char PRDsuffix[];

if 0 /* This is affy.h now */
typedef struct { /* RELEVENT INFORMATION ABOUT GRID */
   fcoord ulc,urc,lrc,llc; /* CORNERS OF THE GRID (image coords) */
   int nx,ny/*,ulx,uly,lrx,lry/**/;
   int offx, offy, totx, toty;
} griddescr;
#endif
griddescr griddesc;

int cellimage, cellimage2;
```

```
int pre_aligned = 0;
int ignorewidth = 1;
static int ncellsx=32,ncellsy=32;
static int dont_clip_beep;

int hsmooth = 25,invertX=0,invertY=0, swapxy = 0;

static int noprompt = 0; /* Whether or not to prompt in
countcells */ double countscale=1.;

scalewindow1(coord *sulc, coord *slrc, coord *dulc, coord *dlrc,
int fixXY, int f1,int f2);
void drawgrid(int *ncellsx, int *ncellsy, int width);
int celloutput(FILE *fp,int x, int y, unsigned long histogram[],
int, int );
scancells(FILE *fp,int ncellsx,int ncellsy, int width, int
srcimg);

int srcimg,xmapoff,ymapoff;
double xmapscale=1.,ymapscale=1.;
char prcfile[81];
char *get_peptide_string (int x, int y, char *prc_name, int maxx,
int maxy, char *fluff);
#include <setjmp.h>
extern jmp_buf jumper;
/*****************************************************************
linearcalibrate */
/* Set up a linear intensity calibration, where grayval 0 means
pixlo,
grayval 255 means pixhi */
void linearcalibrate(double pixlo, double pixhi) {
    int nentries, index[2];
    float energy[2];
    index[0] = 0;
    energy[0] = pixlo;
    index[1] = NLEVELS - 1;
    energy[1] = pixhi;
    nentries = 2;
    fillicaltable(index,energy,nentries);
}
/*****************************************************************
AFFYcheckcalib */
/* Make sure we have calibrations, or ask for the values */
void AFFYcheckcalib(){
    double pixlo = 0, pixhi = 255;
    if(intensitycal(0)==0 && intensitycal(NLEVELS-1)==NLEVELS-1)
{
        fbgetfloat(&pixlo,0,0,"True value for pixel level 0");
        fbgetfloat(&pixhi,0,0,"True value for pixel level 255");
        linearcalibrate( pixlo, pixhi );
    }
}
/*****************************************************************
AFFYreadTIFFcalib */
```

```c
/* Read the intensity calibration from label */
AFFYreadTIFFcalib( char *label ) {
    int pixlo, pixhi;
    char *ptr;
    ptr = strchr(label,'['); /* READ THE COUNTS RANGE FROM THE
COMMENT */
    if(ptr){
        char buf[MAXCOMMENT],*ptr1,*ptr2;
        pixlo = atof(ptr+1);
        ptr = strstr(label,"..");
        if(ptr) pixhi = atof(ptr+2);
        linearcalibrate( pixlo, pixhi );

/* PUT THE ACTUAL FILE NAME IN */
        strcpy(buf,label);
        if((ptr1 = strchr(label,']')) ==0) goto end1; /* find
start of name */
        ptr1 +=3;
        if((ptr2 = strchr(buf,':')) ==0) goto end1; /* Find end
of name */
        if((ptr2  =  strstr(buf,".TIF"))  ==0  &&  (ptr2  =
strstr(buf,".tif")) ==0) goto end1; /* Find end of name */
        ptr2+=4;
        sprintf(ptr1,"%s%s",imagefile,ptr2);
end1:           ;
    }
    else linearcalibrate( 0, 255);
}
/****************************************************************
showdata2 */
/* Show data, but take px,py as screen coords */
void showdata2(int sx, int sy, int color){
    coord sp0, rawp0;
    int always = 0;
    sp0.x = sx; sp0.y = sy;
    scalept(&rawp0,&sp0);
    showdata(rawp0.x,rawp0.y,color, always);
}
/****************************************************************
showdata */
/* Given the raw-image X,Y, compute the grid value, and display
the
relevent parameters on top line */
showdata(int px, int py, int color, int always){
    int x, y, ingrid;
    static oldx=-1,oldy;
    char buf[160], *pepptr;
    celldata cdat;
    ingrid = whichcell(px,py,&x,&y);
    if(!ingrid) x=-1;
    if(!always && x==oldx && y == oldy) return;
    if( x<0 || x>=griddesc.nx || y<0 || y>=griddesc.ny ) return;
/* Out of range! */
    oldx=x; oldy=y;
    if(cellimage) fgetrawrow(x, y, &cdat, 1, cellimage);
```

```c
        /* Correct for offset of cell subset */
        x += griddesc.offx;
        y += griddesc.offy;
        if(*prcfile && ingrid) {
            pepptr = get_peptide_string(x, y, prcfile, griddesc.totx,
griddesc.toty,"");
        } else pepptr="";
        if(!pepptr) longjmp(jumper,1); /* Get out of here, quick */
        if(cellimage) sprintf(buf,"Cell (%3d %3d) %6.1f ±%-3d (%4.1f)
photons; %3d pixels",
             x,     y,    cdat.intensity,    cdat.stdv,
cdat.stdv/MAX(1,sqrt(cdat.npix)), cdat.npix);
        else sprintf(buf,"Cell (%3d %3d) PEP=%-12s   ",x, y, pepptr);
        menumessage(buf,0);
        x = color; /* DUMMY FOR COMPILER */
}
/***********************************************************
whichcell */
/* Return the cell coords at the given position */
whichcell(int px, int py, int *x, int *y){
    int ulx,uly,lrx,lry,i,xw,yw, dx, dy;
    *x = clip(*x,0,griddesc.nx-1);
    *y = clip(*y,0,griddesc.ny-1);
    *x = griddesc.nx/2;
    *y = griddesc.ny/2;
gotoxy(1,1);
    for(i=0;i<8;i++){ /* Try up to 8 times */
        cellposition(*x,*y,&ulx,&uly);
        cellposition((*x)+1,(*y)+1,&lrx,&lry);
        xw = lrx+1-ulx; yw = lry+1-uly;
        if(xw<1) xw=1; if(yw<1)yw=1; /* Avoid divide by zero */

/* UPDATE X and Y */
        dx = dy = 0;
        if(px<ulx) dx = -1+(px-ulx)/xw;
        else if(px>lrx) dx = 1+(px-lrx)/xw;
        if(invertX) dx = -dx;/**/
        if(swapxy) *y += dx;
        else *x += dx;

if(py<uly) dy = -1+(py - uly)/yw;
        else if(py>lry) dy = 1+(py-lry)/yw;
        if(invertY) dy = -dy;/**/
        if(swapxy) *x += dy;
        else *y += dy;
        if(dx==0 && dy==0) { /* This is it...*/
            return 1;
        }
        *x = clip(*x,0,griddesc.nx-1);
        *y = clip(*y,0,griddesc.ny-1);
    }
/* printf("whichcell: %d %d failed\n",px,py);/**/
/*    sound(5000); delay(1); nosound();/**/
    return 0;
}
```

```c
/**********************************************************
scalept */
/* Scale a point from display to image coords */
scalept(coord *pd, coord *ps){
   pd->x = (ps->x-xmapoff)*xmapscale;
   pd->y = (ps->y-ymapoff)*ymapscale;
}
/**********************************************************
unscalept */
/* Scale a point from image to display coords */
unscalept(coord *pd, coord *ps){
   pd->x = (ps->x / xmapscale)+.5 + xmapoff;
   pd->y = (ps->y / ymapscale)+.5 + ymapoff;
}
fcoord dcellpos; /* Double precision cell coord, for whoever needs it */
/**********************************************************
cellposition */
/* Return the ulc of the given cell, given the global coords:
 ulc,lrc,urc,llc */
cellposition(int x, int y, int *ulx, int *uly ){
   double fx, cfx, fy, cfy; /* Fractions and Complements of positions in X, Y */
   double topx, botx, lefty, righty;

*ulx = *uly = 0; /* default values in case of error */ cfx = (double)x / griddesc.nx;
   cfy = (double)y / griddesc.ny;
   fx = 1. - cfx;
   fy = 1. - cfy;
   if( fx<0 || cfx<0. || fy<0. || cfy<0.){
       errorprintf("Error in cellposition: x, y=%d %d, nx=%d %d\n",
           x, y, griddesc.nx, griddesc.ny);
       return;
   } topx  = fx * griddesc.ulc.fx + cfx * griddesc.urc.fx;
   botx  = fx * griddesc.llc.fx + cfx * griddesc.lrc.fx;
   lefty = fy * griddesc.ulc.fy + cfy * griddesc.llc.fy;
   righty= fy * griddesc.urc.fy + cfy * griddesc.lrc.fy;

dcellpos.fx = fy * topx + cfy * botx;
   dcellpos.fy = fx * lefty+ cfx * righty;
   *ulx = dcellpos.fx + .5;
   *uly = dcellpos.fy + .5;
}
/**********************************************************
labelcols */
/* Print column and row labels on the top and right side of the grid */
labelcols() {
   int ncellsx = griddesc.nx, ncellsy = griddesc.ny;
   int i,oldcolor= I_GREEN, lastx=0,lasty=0;
   char buf[40];
```

```
    swapint(&oldcolor,&textcolor); centertext=0;
    for(i=0;i<ncellsx;i++){
       cellposition(i, 0, &textpos.x, &textpos.y);
       textpos.y -= charsize.y;
       unscalept(&textpos,&textpos); /* Convert to display coords
*/
       if(textpos.x<= lastx) continue;
       sprintf(buf,"%d",(invertX?ncellsx-i-1:i)%10);
       fbputs(buf);
       lastx = textpos.x;
    }
    for(i=0;i<ncellsy;i++){
       cellposition(ncellsx, i, &textpos.x, &textpos.y);
       textpos.y -= charsize.y;
       unscalept(&textpos,&textpos); /* Convert to display coords
*/
       if(textpos.y<= lasty) continue;
       sprintf(buf,"%d",(invertY?ncellsy-i-1:i));
       fbputs(buf);
       lasty = textpos.y + charsize.y;
    }
    swapint(&oldcolor,&textcolor);
}
/***********************************************************
allocate_cellimage */
/* allocate the image to hold the cell array */
allocate_cellimage(int nx, int ny) {
    int fcols, frows, fbytes;
    celldata cdat;
    if( cellimage ) {
       frgetsize( &fcols, &frows, &fbytes, cellimage );
       imclose( cellimage ); cellimage = 0;
    }
    cellimage = imopen_special(nx, ny, sizeof(celldata), I_FAST,
NULL, NULL);

memset( &cdat, 0, sizeof(cdat));
    frameclear( cellimage, &cdat); /* Clear it to zero */
    /* Make sure countscale is initialized too because it's needed
for stdv */
         c o u n t s c a l e   =   r a w d a t a ?   1 .   :
(intensitycal(NLEVELS)-intensitycal(0))/NLEVELS;
    return cellimage;
}
/***********************************************************
analyzecell */
/* Compute the histogram from the given cell, given the
ignore-width */
analyzecell(int x, int y, ULONG *histogram, int lwidth,
       UINT *phmin, UINT *phmax, int srcimg ){
    char rbuf[MAXCOLS];
    int irbuf[MAXCOLS];
    int x0, y0, x1, y1, hwidth = lwidth/2;
    int nx, pix;
    int cellwd;
    int xx, yy, cnt, hmin, hmax;
```

```
    cellposition( x, y, &x0, &y0 );
    cellposition( x+1, y+1, &x1, &y1 );
    x0 = MAX(0,x0 + lwidth-hwidth );
    y0 = MAX(0,y0 + lwidth-hwidth );
    cellwd = x1-x0;
    nx =  MAX( cellwd - lwidth, 1);
    memset(histogram,0,(rawdatmax+1) * sizeof(*histogram));
    hmin = 32767;
    hmax = 0;
    cnt = 0;
    for(yy=y0;yy<=y1-hwidth;yy++){ /* histogram this row */
        if( !rawdata ){
            fgetrow(x0,yy,rbuf,nx,srcimg);/**/
            for(xx=0;xx<nx;xx++) {
                pix = rbuf[xx];
                hmin = MIN( hmin, pix );
                hmax = MAX( hmax, pix );
                histogram[pix]++;
                cnt++;
            }
        } else { /* 16-bit pixels */
            fgetrawrow(x0,yy,irbuf,nx,srcimg);
            for(xx=0;xx<nx;xx++) {
                pix = irbuf[xx];
                hmin = MIN( hmin, pix );
                hmax = MAX( hmax, pix );
                histogram[pix]++;
                cnt++;
            }
        }
    }
    *phmin = hmin;
    *phmax = hmax;

if( !cnt ){
        seterror(UNDEFINED_ERROR,"Countcells cell (%d,%d) had no area",x,y);
    }
}
/*************************************************************
scancells */
/* Given the grid, go through each cell, analyze it, and output
its result. */
scancells(FILE *fp,int ncellsx,int ncellsy, int lwidth, int srcimg){
    int x,x0,y,y0,x1, y1, ccolor;
    static ULONG *histogram;/**/ griddesc.nx = ncellsx, griddesc.ny=ncellsy;

cellposition( 0, 0, &x0, &y0 );
    cellposition( ncellsx, ncellsy, &x1, &y1 );

/* Allocate the histogram after the "cellimage" is allocated
so it can be freed */
    if( histogram) {
```

```c
            free(histogram); /* In case someone hit ^C */
        }
        histogram = malloc( (rawdatmax+1) * sizeof( *histogram ));

for(y=0;y<ncellsy;y++){ /* FOR EACH ROW OF CELLS */
            for(x=0;x<ncellsx;x++){ /* FOR EACH CELL */
                unsigned int hmin, hmax;
                analyzecell(x, y, histogram, lwidth, &hmin, &hmax,
    srcimg);

ccolor=celloutput(fp,(invertX)?ncellsx-x-1:x,
                    (invertY)?ncellsy-y-1:y,histogram, hmin, hmax );

{ /* Display the cell */
                    char *buf;
                    int nx, ny;
                    coord sulc, fulc;
                    /* PUT a model cell in outframe */
                    cellposition( x, y, &fulc.x, &fulc.y );
                    cellposition( x+1, y+1, &sulc.x, &sulc.y );
                    nx = (sulc.x-fulc.x)/xmapscale + .9; /* Width on
    display */
                    ny = (sulc.y-fulc.y)/ymapscale + .9; /* Width on
    display */
                    buf = malloc(nx*ny);
                    memset(buf,ccolor,nx*ny);
                    unscalept(&sulc,&fulc);
                    putblock( MAX(0,sulc.x), MAX(0,sulc.y), nx, ny, buf
    );
                    free(buf);
                }
                if(keyorbutton()) return;
            }
        }
        if( histogram ) {free( histogram ); histogram = 0; }/**/
    }

/***********************************************************
cellhstats */
/* Given the histogram for a cell, find the peak intensity,
return the
number of pixels, the sum intensity, and standard dev */
/* Return FALSE if there's evedence of clipping to zero or 255
*/
int cellhstats(unsigned long *histogram,int *ppeakn, double
*mean,
        double *stdv, int hmin, int hmax){
    double cmean, cstdv;
    register int i, hval;
    int sum, peakn, smooth, iold, totpix;
    int maxclip, clipped;
    long sumsq, isum, peakisum, peaksumsq;
    double tmean, tstdv;

if( hmin>hmax ){
```

```
        seterror(UNDEFINED_ERROR,"cellhstats    min    >    max
(%d-%d)",hmin,hmax);
        hmin=0; hmax = NLEVELS;
    }
    /* COMPUTE STDV OF WHOLE DISTRUBUTION */
    sum = isum = sumsq = 0;
    for( i=hmin; i<=hmax; i++){
        hval = histogram[i];
        if( hval ){
            sum += hval;
            isum += (long)hval * i;
            sumsq += (long) hval * i * i;
        }
    }
    meanstdv( (double)sum, (double)isum, (double)sumsq, &cmean,
&cstdv);
    *ppeakn = sum; *mean = cmean; *stdv = cstdv;
    /* I've tested "12", and that screws up; 16 seems to always
work */
#define MINSMOOTH 10
#if 1   /* Reinstalled 11-17-93, tested with 8- and 16-bit images
*/
    if( rawdatmax==NLEVELS-1 ) { /* use tried and true algorithm
*/
        hsmooth  =  smooth  =  MIN(   25*rawdatmax/NLEVELS,
MAX(MINSMOOTH,(int)cstdv*1.5/*cmean*/) );
    } else {
        hsmooth = smooth = MAX(MINSMOOTH,(int)(sqrt(cmean)*6));/*
I don't know why '6' yet. */
/*printf("%.0f )",cmean, hmin, hmax);/**/
    }
#else
    smooth = MIN( hsmooth, MIN( MAX(6,(int)cmean), cstdv) );/**/
#endif
    peakn = 0;
    totpix = isum = sumsq = 0;
/*   for(i=sum=hmin; i<=hmax; i++) { /* THIS DOESN'T WORK RIGHT
FOR SOME REASON!!! */
    for(i=sum=0; i<=rawdatmax; i++) { /* FIND MAX HISTOGRAM LEVEL
*/
        /* SUM VALUES ON NON-ZERO HIST. BINS */
        if((hval=histogram[i])!=0){
            totpix += hval;
            sum += hval;
            isum += (long)hval*i;
            sumsq += hval*(long)i*i;
        }
        /* UNSUM DATA OUTSIDE OF smooth TO GIVE BOXCAR AVERAGE */
        iold = i-smooth;
        if(iold>=0 && (hval=histogram[iold])>0){
            sum  -= hval;
            isum -= (long)hval*iold;
            sumsq -= hval*(long)iold*iold;
        }
        if(sum>peakn) {
            peakn = sum;
```

```
        peakisum = isum;
        peaksumsq = sumsq;
    }
}
maxclip = totpix/2;
clipped = ( histogram[0] > maxclip) ||
          (histogram[rawdata?rawdatmax:maxgray]>maxclip) ||
          (histogram[rawdatmax-1]>maxclip);
if( rawdata ) clipped = 0;  /* This is always true since there's no clipping! */
meanstdv( peakn, peakisum, peaksumsq, &tmean, &tstdv);
if( !rawdata && (debug || *mean>=255) ){ /* Detect garbage pixels sometimes */ printf("mean = %.1f peak=%3d min=%3d, max=%3d h[0]=%21d %21d %ld %ld %ld\r",
    *mean, peakn, hmin, hmax, histogram[0], histogram[1],
histogram[2], histogram[3], histogram[4]);
    return 0;
}
*mean = tmean;
*stdv = tstdv;
*ppeakn = peakn;
return clipped;
}
/*************************************************************
celloutput */
/* Given the histogram for a cell, output its coords and value */
celloutput(FILE *fp,int x, int y, unsigned long *histogram, int hmin, int hmax ){
    int peak = 0, clipped, imean /*, xoff, yoff*/;
    celldata cdat;
    double stdv, intensity, mean;

clipped = cellhstats(histogram,&peak,&mean,&stdv,  hmin, hmax);/**/
    if( !dont_clip_beep && clipped ) {
        sound(3000); delay(100); nosound();
        errorprintf("Cell %d %d appears to be clipped (dark or bright) ESC->no more beeps\n",x,y);
        if( mbutton == ESCAPE ) dont_clip_beep = 1;
        nosound();
    }
    if(peak<1) peak=1;
    intensity = rawdata ? mean : intensitycal(mean);
    cdat.intensity = intensity;
    cdat.npix = peak;
    cdat.stdv = stdv*countscale;
    fputrawrow( x, y, &cdat, 1, cellimage );
    if(swapxy) swapint(&x,&y);

/* Correct for offset of cell subset */
    x += griddesc.offx;
    y += griddesc.offy;
/*printf("%d",rawdata);/**/
```

```
/* I REALLY don't know why this xoff, yoff B.S. is needed.. */
#if 0
   xoff = x + griddesc.offx;
   yoff = y + griddesc.offy;
#else
/*   xoff = x + griddesc.offx;
   yoff = y + griddesc.offy;/**/
endif if 0 /* algorithm testing output */
   fprintf(fp,"%3d \t%3d \t%5.1f \t%5.1f \t%5.1f \t%5.1f \t%3d, %d\n",
       x,y,mean,stdv,cmean, cstdv, peak, hsmooth);
#else
   if( fp ) fprintf(fp,"%3d \t%3d \t%5.1f \t%5.1f \t%3d\n",
       x,y,intensity,stdv*countscale,peak);
#endif
/*        if( ferror( fp ) ) printf("File write error %s.\n",sys_errlist[errno]);/* This links in too much text! */
   if( fp && ferror( fp ) ) printf("File write error %d. (disk full?)\n",errno);
   if(x==0 && (y&1)==0 && !noprompt){ /* Say what's happening occasionally */
       gotoxy(1,1);
       printf("(%3d,%3d)   %5.1f   ±%5.1f   n=%3d \r",x,y,intensity,stdv*countscale,peak);
   }
   if(fp==stdout) getch();
   imean = mean + .5;
   return rawdata? lut16[imean] : clip(imean,0,maxgray);/**/
/*   return imean; /**/
}
/****************************************************************
drawgrid */
/* ASK FOR NUMBER OF ROWS AND COLS OF CELLS, AND DISPLAY THE
RESULTANT GRID */
void drawgrid(int *ncellsx, int *ncellsy, int width){
   int i,j,oldcolor = I_RED;
   coord p0,p1;
   if(width==0) {
       width=2; fbgetint(&width,1,200,"Line width");
       fbgetint(&oldcolor,0,0,"Line color (252=RED)");
   }
   swapint(&color,&oldcolor);/**/
   for(i=0;i<= *ncellsx;i++) { /* VERTICAL LINES */
       cellposition( i, 0, &p0.x, &p0.y );
       cellposition( i, *ncellsy, &p1.x, &p1.y );
       unscalept(&p0,&p0); /* SCALE TO SCREEN COORDS FROM FRAME */
       unscalept(&p1,&p1);
       p0.x -= width/2;
       p1.x -= width/2;
       for(j=0;j<width;j++,p0.x++,p1.x++) plotline(&p0,&p1);
   }
   for(i=0;i<= *ncellsy;i++) { /* HORIZONTAL LINES */
       cellposition( 0        , i, &p0.x, &p0.y );
```

```
        cellposition( *ncellsx, i, &p1.x, &p1.y );
        unscalept(&p0,&p0); /* SCALE TO SCREEN COORDS FROM FRAME
*/
        unscalept(&p1,&p1);
        p0.y -= width/2;
        p1.y -= width/2;
        for(j=0;j<width;j++,p0.y++,p1.y++) plotline(&p0,&p1);
    }
}
/***********************************************************
readTIFFtoImage */
/* Read a TIFF image to the datimage */
/* Return 2 if old image used; 1 if a new image was read, 0 if
no image avail. */
readTIFFtoImage(){
    FILE *fp,*readtiffheader();
    int fcols,frows,llen=MAXCOMMENT, sampperpix, invert;
    extern int mbutton;
    char comment[MAXCOMMENT+1];
    char mask[81],name[41];
    if(datimage){
        if( !noprompt ) if(yesnomouse("Use old image?")) return 2;
        imclose(datimage);
        datimage=0;
    }
    buttonhelp("Select file","","Done");
    sprintf(mask,"*.%s",filesuffix);
    if(!getmousedir(fileprefix,mask,name)   ||   mbutton==2   ||
name[0]=='\0') return 0;
    if(_mousebutton==2) return 0;
    sprintf(imagefile,"%s%s",fileprefix,name);
    strcpy(datfilename,imagefile);
#ifdef AFFY
    {
        #define UNCAL .000001
        float *calbuf = geticaltable();
        calbuf[ 0 ] = UNCAL;
    }
#endif
    fp = readstdtiffheader(imagefile,&fcols,&frows,comment, &llen,
NULL, &sampperpix, &invert);
    if(!fp) return 0;
    statusprintf("%s", imagefile);
    if((datimage=imopen(fcols,frows,iFAST))==0) return 0;
    fgetwindow (fp, 0, 0, fcols, frows, datimage);
    fclose(fp);
    saveundermenu();
    frsetcomment( comment, datimage);
    datimagemax = NLEVELS - 1;
#ifdef AFFY
    if( intensitycal(0) == (float)UNCAL ){ /* There wasn't an
intensity calibration in the file...*/
        AFFYreadTIFFcalib( comment ); /* Read the intensity
calibration from label */
    }
#endif
```

```
        return 1;
}
/****************************************************************
analyzegrid */
/* First set up the scan, then go through all the cells and measure their
"average" intensity: actually the intensity of greatest area */
analyzegrid(){
    extern int mousefactor;
    char buf[80];
    int icols,irows, newimage = 0;
    FILE *fp;
    char filename[65],*ptr;
/*   char outfile[70],cmdbuf[120]; /**/
    strcpy(filename,imagefile);

rawdata = 0;
    rawdatmax = NLEVELS-1;

noprompt = 0;
    dont_clip_beep = 0; /* Always start image with this false */
    serialnameflag = yesnomouse("Analyze a series of images?");
    if( serialnameflag ){
        char name[90];
        serialroot[0] = 0; /* Clear serial root for re-entry */
        if( !imakeserialname( serialroot, name ) ) return;
        serialfilecounter--; /* Set it back down again */
        fbgetint( &serialfilecounter, 0, 0, "Starting file number");
    } else {
        errorprintf("You should be using grid-roam now...");
    }
start:
    if( serialnameflag || yesnomouse("Read a TIF image in at full resolution?")){ /* READ IN A WHOLE TIF FILE */
        if(!readTIFFtoImage()) {
            serialnameflag = 0;
            return;
        }
        newimage = 1;
    }
    sprintf(buf,"Use '%s', which AFFY left in memory?",imagefile);
    if(datimage && (newimage || yesnomouse(buf))){ /* USE MEMORY IMAGE */
        coord s0,s1,d0,d1;
        int ibytes;
        char comment[MAXCOMMENT+1];
        imgetsize(&icols,&irows,&ibytes,datimage);
        if(ibytes == 2) { /* Raw data: */
            rawdata = 1;
            rawdatmax = datimagemax;
            errorprintf("Using 16 bit data. Max val = %d\n",rawdatmax);
        } else {
            rawdata = 0;
            rawdatmax = NLEVELS - 1;
```

```
        }
        s0.x = s0.y = 0; s1.x = icols-1, s1.y = irows-1;
        d0.x = max(0,(NCOLS-icols)/2);
        d0.y = max(0,(NROWS-irows)/2);
        d1.x = min(NCOLS-1,d0.x+icols-1);
        d1.y = min(NROWS-1,d0.y+irows-1);
        srcimg = datimage;
        frgetcomment(comment, MAXCOMMENT, srcimg);
        frsetcomment(comment, framenum);
/*              scalewindow(&s0,&s1,&d0,&d1,0,   smoothzoom,
srcimg,framenum);/**/
        scalewindow(&s0,&s1,&d0,&d1,0,   (d1.x-d0.x)!=(s1.x-s0.x),
srcimg,framenum);/**/
        saveundermenu();
/*      xmapoff = ymapoff = 0;/**/
        xmapoff = d0.x; ymapoff = d0.y;
        xmapscale = (double)icols/(d1.x-d0.x);
        ymapscale = (double)irows/(d1.y-d0.y);
        strcpy(filename,datfilename);
   } else {xmapscale=ymapscale=1.; xmapoff=ymapoff=0; srcimg =
0; }

/*errorprintf("xmapscale=%f %f\n",xmapscale,ymapscale);/**/
   ptr = strrchr(filename,'.');
      if(ptr) strcpy(ptr,".cel"); /* REPLACE EXTENSION WITH "CEL"
*/
   framecopy(0,1);

strlwr(filename); /* CONVERT NAME TO LOWER CASE ('cause Suzie
asked) */ buttonhelp("Enter","Clear text","Enter");
   if( !noprompt) fbgetword(filename,-63,"Output filename (none
to skip processing)");
   if( !noprompt && !aligngrid()) goto end;
   if(1 /*strlen(filename)>0*/){
      if( !noprompt ) fbgetint(&ignorewidth,0,7,"Line width to
ignore");
      ptr = strrchr(filename,'.');
      if(!ptr && strlen(filename)>0) strcat(filename,".cel"); /*
ADD "CEL" EXTENSION */
      AFFYcheckcalib();

/* Compute scale factor to convert stdv from levels to
photons */
         c o u n t s c a l e   =   r a w d a t a ?   1 .   :
(intensitycal(NLEVELS)-intensitycal(0))/NLEVELS;

fp = fopen(filename,"w");
      if(fp<=0 && strlen(filename)>0) {
         seterror(FILE_DIDNT_OPEN,filename);
         serialnameflag = 0;
         return;
/*       fp = stdout;/* This causes a debug print mode */
      }
      writeCELheader( fp, srcimg );
```

```
        framecopy(1,0);
        scancells(fp, ncellsx, ncellsy, ignorewidth, srcimg);
        fclose(fp);
        if( serialnameflag ) {
            drawgrid(&ncellsx,&ncellsy,1);
            goto end;
        }
        if( !noprompt && (1 || !yesnomouse("Skip viewing of subtracted images?"))) {
            { /* Compute absolute difference between original, and analyzed image */
                int s1=1, s2=2, dest=3, nframes=3, roimode=1, frmlist[3]={3,2,1};
                int oldtcompare = lflashtime;
                framecopy(framenum,s2);
                statusprintf("...wait a moment...");
                setroitype(POLYGON_ROI);
        if( pre_aligned )    setroitype(FULLFRAME_ROI);  /* Quick-fix 11/12/93 */
                dopolyasub(s1, s2, dest);
                lflashtime = 1300;
                statusprintf("Comparing difference image, processed, and raw images.");
                framecompare1(frmlist, nframes, roimode);
                lflashtime = oldtcompare;
                framecopy(s2,framenum);
            }
            if(yesnomouse("Label the columns and rows?")) {
                labelcols();
            }
            if(yesnomouse("Draw   grid?"))   drawgrid(  &ncellsx, &ncellsy, 0);
            saveundermenu();
            framecopy(0,2);
            if(yesnomouse("Save to disk?")) isaveimage();
        }
    }
/*   else goto labelit;/**/
    if(strlen(filename) && yesnomouse("Restore original image?"))
{
labelit:
        framecopy(1,0);
        if(yesnomouse("Label the columns and rows?")) {
            labelcols();
        }
        if(yesnomouse("Draw grid?")) drawgrid(&ncellsx,&ncellsy,0);
        saveundermenu();
    }
end:
    linear();

/* Handle serial files */
    if( serialnameflag ){
        noprompt = 1;
        goto start;
    }
```

```
      serialnameflag = 0;
      serialfilecounter = 0;
}
/*************************************************************
itofcoord */
/* convert an (int) coord to a (double) fcoord */
fcoord itofcoord(coord *pt ){
   fcoord fpt;
   fpt.fx = pt->x;
   fpt.fy = pt->y;
   return fpt;
}
/*************************************************************
ftoicoord */
/* convert a (double) fcoord to an (int ) coord */
coord ftoicoord(fcoord *fpt ){
   coord pt;
   pt.x = fpt->fx;
   pt.y = fpt->fy;
   return pt;
}
/*************************************************************
sortcoords */
/* Sort the first four polygon corners into ulc, urc, lrc,llc,
and pass them
   to griddesc. */
sortcoords(){
   int ctrx, ctry,i,dx,dy;
   coord pt;
   fcoord fpt;
   for(ctrx=ctry=i=0;i<4;i++){  /* Find the center of the box */
      pt=polygon[i]; ctrx += pt.x; ctry += pt.y;
   }
   ctrx /= 4; ctry /=4;
   for(i=0;i<4;i++){ /* Judge each point by its position relative
to ctr */
      pt = polygon[i];
      dx=pt.x-ctrx; dy=pt.y-ctry;
      scalept(&pt, &pt );
      fpt = itofcoord( &pt );
      if(dx>0){
         if(dy>0) griddesc.lrc = fpt;
         else     griddesc.urc = fpt;
      } else{
         if(dy>0) griddesc.llc = fpt;
         else     griddesc.ulc = fpt;
      }
   }
}
/*************************************************************
vplotlongarray */
/* Plot values from an integer array, scaled to fit on screen */
void vplotlongarray(long *array, int size,int orgx, int orgy, int
topx, int pcolor) {
   long maxb = 1,1,dx;
   int i;
```

```
    coord p0,p1;
    swapint(&color,&pcolor);
/* FIND MAX FOR SCALING */
    for(i=0;i<size;) if((l = array[i++]) > maxb) maxb = 1;
    dx = topx - orgx;
/* GET FIRST POINT */
    p1.y = orgy; p1.x = orgx+(dx*array[0]/maxb);
    for(i=1;i<size;) {
        p0.y = i+orgy;
        p0.x = orgx+(dx*array[i++]/maxb);
        drawline(&p1,&p0,color);
        graphputpix(p0.x,p0.y,color); /* to plot the end point a
third time so it doesn't disappear */
        p1=p0;
    }
    color = pcolor;
}

/****************************************************************
findpeak */
/* Find the first peak in the given direction */
int findpeak( long *buf, int cols, int reverse, int start ){
    int i, incr;
    int minpeak;
int scale = 3; /* This should come from parameter list */
    int dist = 3*scale; /* Distance for measuring slope: maximum
amount of blur */
    long dif, peak = 0, peaki, d1, d2;
    incr = reverse? -1 : 1;

for(minpeak = i = 0; i<cols; i++) minpeak = MAX(minpeak,
buf[i]);
    minpeak /= AUTOSENSITIVITY;
#if 0
if(temp > 0 ) minpeak = minpeak / temp;
if( temp < 0 ) minpeak = -temp;
if( temp == 0) minpeak /= AUTOSENSITIVITY;
endif start = MAX( start, dist);
    peaki = start;
    for( i = reverse ? cols-start : start; reverse?i>4 : i<cols-4;
i+=incr){
        /* Make sure we're looking at something (with noise) */
        if( buf[i] < minpeak || buf[i]==buf[i+incr] ) continue;

dif = buf[i]/3; /* Needs to be a significant peak */
        d1 = buf[i]-buf[i-dist];
        d2 = buf[i]-buf[i+dist];
        if( d1 > dif && d2 > dif){
#if 1 /* Use first point over threshold */
            return i;
#else
            if( buf[i] > peak ){ /* Slope is increasing */
                peak = buf[i];
                peaki = i;
```

```
                } else { /* Slope is decreasing */
/*              return peaki - incr*scale ; /* We always overshoot
for some reason */
                return peaki;/**/
            }
#endif
        }
    }
    return peaki;
} int oldalign, autoalign, coarse_align_only;

/****************************************************************
SetGridCorners */
/* Interactively set the corner positions for the grid */
SetGridCorners(){
    int oldctype = cursortype;
    int smoothflag = smoothzoom;
    saveroi(1); /* Save original ROI */ if(abs(srcimg)>0){ /* USING A DATA IMAGE, NOT SCREEN */
        int     i,but,cols,rows,oldcsize  =   cursorsize,
icols,irows,ibytes;
        int j;
        int dcols, drows;
        double scale = 3;
        coord s0,s1,d0,d1,oldnclip = normclip;
        fcoord *cptr;
        frgetsize(&icols,&irows,&ibytes,srcimg);
        d0.x = 0; d0.y = 0;
/*      sortcoords(); /* Set ulc,lrc,urc,llc */
        for(j=0;j<4;j++){ /* For each corner */
            if( keyorbutton() ){ /* Allow me to quickly skip past
here */
                continue;
            }
            i = j;
            if( i&2 ) i^=1; /* Switch corners 2 and 3 */ define XBIT 1  /* If this bit is set, we're on left side */
define YBIT 2  /* If this bit is set, we're on bottom */
            if(i==0) cptr=&griddesc.ulc; /* Designate current CORNER
*/
            if(i==1) cptr=&griddesc.urc;
            if(i==2) cptr=&griddesc.llc;
            if(i==3) cptr=&griddesc.lrc;
/*#define WSIZE (autoalign?100 : 150)   /* Viewing window size */
#define WSIZE   (150)   /* Viewing window size */
            cols=MIN( icols/4, WSIZE);
            rows=MIN( irows/4, WSIZE); /* DEFAULT CORNER SIZE */
/*printf("Before: %.1f %f.1f total=%d %d\n",cptr->fx, cptr->fy,
icols, irows);/**/
            /* Copy corner to display */
            s0.x = max(0,MIN((int)cptr->fx-cols/2,icols-cols));
            s1.x = min(s0.x + cols,icols-1);
```

```
        s0.y = max(0,MIN((int)cptr->fy-rows/2,irows-rows));
        s1.y = min(s0.y + rows,irows-1);
        dcols = (s1.x-s0.x)*scale;
        drows = (s1.y-s0.y)*scale;
        d1.x = min(d0.x + dcols-1,NCOLS-1); /* Use clipped image
size */
        d1.y = min(d0.y + drows-1,NROWS-1);
        smoothflag = (d1.x-d0.x)!=(s1.x-s0.x); /* Only smooth
if scale changed */
/*smoothflag =0;/**/
        clearrect(d0.x, d0.y, d1.x+20, d1.y+20, 0, framenum);
        if( !oldalign ){
            int sframe = srcimg;
            coord olds0 = s0, olds1 = s1;
            setroitype(WINDOW_ROI);
#if 0  /* This median or smoothing filtering doesn't make any
real difference 2/7/94*/
            saveroi(2); /* Save the current ROI */
            rectcopy( s0.x, s0.y, 0, 0, s1.x-s0.x+1, s1.y-s0.y+1,
sframe, framenum);
            sframe = framenum;
            s1.x -= s0.x;
            s1.y -= s0.y;
            s0.x = s0.y = 0;
            setwindowroi( s0.x, s0.y, s1.x, s1.y );
            smooth /*pmedian*/(sframe, sframe);
            getroi(2);
#endif
            scalewindow(&s0,&s1,&d0,&d1,0,smoothflag,sframe,
framenum);/**/
            s0 = olds0; s1 = olds1; /* Restore these for mapping
the real location */
#if 0
            {
            coord d2;
            d2.x = d0.x + (s1.x-s0.x);
            d2.y = d0.y + (s1.y-s0.y);
                scalewindow(&s0,&s1,&d0,&d2,0,0,srcimg,
framenum);/**/
            w0 = d0; w1 = d2;
            sobel( framenum, framenum );/**/
            scalewindow(&d0,&d2,&d0,&d1,0,smoothflag,framenum,
framenum);/**/
            }
#endif
            {
            void   plotlongarray(long   *array,int   size,int
orgx,int orgy,int topy,int pcolor);
            long *xprofile, *yprofile, *xdidt, *ydidt;
            coord center;
            center.x = (d0.x+d1.x)/2;
            center.y = (d0.y+d1.y)/2;

xprofile  =  calloc((dcols  +  drows)  *  2,
sizeof(*xprofile));
            yprofile = &xprofile[dcols];
```

```
            xdidt    = &yprofile[drows];
            ydidt    = &xdidt[dcols];
/*              sobel(framenum,framenum);/**/ w0 = d0;
            w1 = d1;
            if(i&XBIT) {   /* Clip off the gray ramp */
               char pix[2];
               /* read the top pixel from the gray ramp */
               fgetrow( icols - 2, 0, pix, 1, srcimg );
               if( pix[0] >= 250 ) w1.x -= 20*scale;  /* Clip
if it's white */
            }
            normclip.y = 500; /* Clip 50% of brightest points
*/
            normalize();
            abs(center.x);

/* Try to avoid "glitches" in the profiles */
            w0.x+=1;
            w0.y+=1;
            w1.x-=scale;
            w1.y-=scale;

/* Reduce size by scalefactor to ignore untouched
pixels */
            windowprofiles( w0.x, w0.y, w1.x, w1.y, framenum,
xprofile, yprofile);/**/
            {
               int cols = w1.x+1 - w0.x;
               int rows = w1.y+1 - w0.y;
               plotroi();
               if( !autoalign ) {
                  plotlongarray( xprofile, cols, w0.x, w1.y,
w0.y, I_RED);/**/
                  vplotlongarray(  yprofile,  rows,  w1.x,
w0.y,w0.x, I_GREEN);/**/
               }
               else/**/
               {
                  int x, prev = 0, xpeak, ypeak, start;
                  int dx = scale*7/2;/**/
                  int yshorten = 0; /* Don't know why this
isn't zero!! */

/* We're trying to ignore 1- or 2- pixel
wide defects
                     by taking the MIN with the derivative
over 3 pixels */
                  /* Take the abs of the first derivative */
                  if( i&XBIT) for(x=dx;x<cols-dx-1; x++) {
                     prev   =   MAX(0,   xprofile[x-1]   -
xprofile[x+1]);
                     xdidt[x]   =   MIN(  prev,  MAX(0,
xprofile[x-dx] - xprofile[x+dx]));
                  } else for(x=dx;x<cols-dx-1; x++) {
```

```
                                    prev   =   MAX(0,   xprofile[x+1]   -
xprofile[x-1]);
                              xdidt[x]   =   MIN(   prev,   MAX(0,
xprofile[x+dx] - xprofile[x-dx]));
                          }
                          prev = 0;

/* Y-derivative */
                          /* ...XXX I don't know why we get a spike
after (rows-15) */
                          if( i&YBIT ) for(x=dx;x<rows-dx-1-yshorten;
x++) {
                                    prev   =   MAX(0,yprofile[x-1]   -
yprofile[x+1]);
                              ydidt[x]   =   MIN(   prev,   MAX(0,
yprofile[x-dx] - yprofile[x+dx]));
                          } else for(x=dx;x<rows-dx-1-yshorten; x++)
{
                                    prev   =   MAX(0,yprofile[x+1]   -
yprofile[x-1]);
                              ydidt[x]   =   MIN(   prev,   MAX(0,
yprofile[x+dx] - yprofile[x-dx]));
                          }
                          start = dx;
                          xpeak = findpeak( xdidt, cols, i&XBIT, start
);
                          ypeak = findpeak( ydidt, rows, i&YBIT, start
);
                          p0.x = xpeak + w0.x;
                          p0.y = ypeak + w0.y;
                          plotlongarray(   xdidt,   cols,   w0.x,   w1.y,
w0.y, I_GREEN);/**/
                          vplotlongarray(   ydidt,    rows,    w1.x,
w0.y,w0.x, I_RED);/**/
                      }
                  }
                  free( xprofile );
              }
          } else {
              scalewindow(&s0,&s1,&d0,&d1,0,smoothflag,srcimg,
framenum);/**/
              histmin = 0;
              histmax = 128; /* Give it 2 cycles through gray scale
*/
              fcolor();
          }
          normclip = oldnclip;
          if( !autoalign ) {
              /* align to the real corner */
              p0.x = clip((int)(d0.x + (cptr->fx -1 - s0.x)*scale),
0, NCOLS-1);
              p0.y = clip((int)(d0.y + (cptr->fy -1 - s0.y)*scale),
0, NROWS-1 );
          }
          cursorsize = dcols * 2;/**/
```

```
              cursortype = 1;
              if( oldalign ) {cursorcolor = I_BLUE; cursor();} /* Put
up a cursor at current posn*/
              cursorcolor = I_RED;
              but = mmov("Mark corner","Cancel","Previous corner");
              cursorsize = oldcsize;
              cursortype = oldctype;
              clearrect(d0.x, d0.y, d1.x, d1.y, 0, framenum);
              if(but>2 && but<8 || but==ESCAPE) break;
              /* update corner */
              cptr->fx = (s0.x + (p0.x-d0.x)/scale + 1.);
              cptr->fy = (s0.y + (p0.y-d0.y)/scale + 1.);
              if(but==2) {j = max(-1,j-2); continue;}
          }
          linear();
          framecopy(1,0);
      } else { /* ALIGN ON SCREEN */
          framecopy(1,0);
          mousefactor *=5;
          setzoom(3); delay(40); setzoom(1); delay(40); setzoom(3);
          setroitype(POLYGON_ROI);
          statusprintf("Align corners; 'n' for next corner; 'Enter'
when done");
          if(cmov()==ESCAPE) goto end;
          { /* NORMALIZE IN CORNER */
              saveroi(1); /* save the old window */
              w0.x   =    MAX(0,    polygon[0].x-50);    w0.y   =
MAX(0,polygon[0].y-50);
              w1.x = polygon[0].x+50; w1.y = polygon[0].y+50;
normalize();
              getroi(1); /* restore the old window */
              if(histmax-histmin < 10) linear(); /* Don't leave the
window fucked up */
          }
end:
          setroitype(WINDOW_ROI);
          setzoom(1); mousefactor /=5;
          sortcoords(); /* convert to image coords and Put proper
coords in ulc,lrc,lrc,llc. */
      }
    setpolytogrid();
    getroi(1); /* Restore original ROI */
}
/*************************************************************
preset_polygon */
/* Preset the polygon corners to the corners of the image */
preset_polygon(int fcols, int frows ){
    coord pt;
    pt.x = pt.y = 10;
    unscalept(&polygon[0], &pt);
    pt.x = fcols-30;
    pt.y = 0;
    unscalept(&polygon[1], &pt);
    pt.x = fcols-30;
    pt.y = frows-10;
    unscalept(&polygon[2], &pt);
```

```
    pt.x = 10;
    pt.y = frows-10;
    unscalept(&polygon[3], &pt);
    sortcoords(); /* Copy points to griddesc. */
}
/***********************************************************
setpolytogrid */
/* set the polygon to the final grid result */
setpolytogrid() {
    coord pt;
    pt = ftoicoord( &griddesc.ulc );
    unscalept(&polygon[0],&pt);
    pt = ftoicoord( &griddesc.urc );
    unscalept(&polygon[1],&pt);
    pt = ftoicoord( &griddesc.lrc );
    unscalept(&polygon[2],&pt);
    pt = ftoicoord( &griddesc.llc );
    unscalept(&polygon[3],&pt);
}
/***********************************************************
aligngrid */
/* Align the grid to the chip */
aligngrid(){
    int old, oldctype = cursortype, oldcsize = cursorsize;
    int i,but, presetonce = 0;
    int fcols, frows, bytes;
    frgetsize( &fcols, &frows, &bytes, srcimg );
    polydim=4;
    if( pre_aligned && yesnomouse("Use current alignment?") )
 return 1;
    unmenu();
    do{ /* ALIGN TO IMAGE */
        {
            int i;
            char *options[] = {
                                                 "  A   l   i   g   n
technique","Auto-Profiles","Profiles","False-color","None","No
Grid"};/**/
            DefaultChooseItem = 1; /* Default to Auto Profiles */
            i = mousechoose(options,6);
            oldalign = (i==3);
            autoalign = (i==1);
            coarse_align_only = (i==4);
            if( i<1 || i>4) return 0;
        }
if( autoalign ){
   preset_polygon(fcols, frows);
}
        if( !autoalign ){
            statusprintf("Put corners roughly on grid corners.");
            for(i=0;i<polydim;i++){
                p0 = polygon[i];
                if( srcimg != 0 && !presetonce ){ /* Check for valid
alignment */
                    coord testpt;
                    scalept(&testpt, &p0);
```

```
                if( testpt.x<-1 || testpt.y<-1 || testpt.x>fcols
|| testpt.y>frows ) {
                        preset_polygon(fcols, frows);
                        p0 = polygon[i];
                        presetonce = 1;
                        i=0;
                }
        }

/* Check for changed screen size since last time */
        p0.x = clip(p0.x, 0, NCOLS-1 );
        p0.y = clip(p0.y, 0, NROWS-1 );
        cursortype = 1;
        cursorsize = 250;/**/
/*      cursorsize = 50;/**/
        but = mmov("mark corner","quit","prev corner");
        cursortype = oldctype;
        cursorsize = oldcsize;
        if(but>2 && but!='\r') return 0;
        if(but==2) i=max(-1,i-2);
        polygon[i] = p0;
    }
    sortcoords();
}
unmenu();
if( !coarse_align_only) SetGridCorners();
/* SCALE ULC, LRC TO FRAME (image coords) */
    if( !noprompt ) {
        old = ncellsx;
        fbgetint(&ncellsx,0,0,"Number of cells across top");
        if(ncellsx!=old) ncellsy = ncellsx; /* Make them the
same by default */
        fbgetint(&ncellsy,0,0,"Number of cells down side");
        griddesc.nx = griddesc.totx = ncellsx;
        griddesc.ny = griddesc.toty = ncellsy;
        if( !autoalign && yesnomouse("Is this a subset of the
whole grid?") ){
            fbgetint(&griddesc.offx,0,0,"X coord of \"origin\"
cell");
            fbgetint(&griddesc.offy,0,0,"Y coord of \"origin\"
cell");
            old = griddesc.totx;
            fbgetint(&griddesc.totx,0,0,"Number of cells across
whole slide");
            if( old != griddesc.totx ) griddesc.toty =
griddesc.totx;
            fbgetint(&griddesc.toty,0,0,"Number of cells down
whole slide");
        }
        allocate_cellimage(griddesc.nx, griddesc.ny);
        /* Test for cells too small, or too rotated */
        {
            double celldx, celldy;
            griddesc.cellsize.fx    =    (griddesc.urc.fx    -
griddesc.ulc.fx) / (ncellsx);
            griddesc.cellsize.fy    =    (griddesc.lrc.fy    -
```

```
            griddesc.urc.fy) / (ncellsy);
#if 0
                    {
                            double rox1, rox2, roy1, roy2;
                            rox1 = atan2(griddesc.urc.fy - griddesc.ulc.fy,
griddesc.urc.fx - griddesc.ulc.fx) * DEGRAD;
                            rox2 = atan2(griddesc.lrc.fy - griddesc.llc.fy,
griddesc.lrc.fx - griddesc.llc.fx) * DEGRAD;
                            roy1 = -atan2(griddesc.llc.fx - griddesc.ulc.fx,
griddesc.llc.fy - griddesc.ulc.fy) * DEGRAD;
                            roy2 = -atan2(griddesc.lrc.fx - griddesc.urc.fx,
griddesc.lrc.fy - griddesc.urc.fy) * DEGRAD;
                            errorprintf("Rotations:Hor: %.3f %.3f Ver:%.3f
%.3f\n", rox1, rox2, roy1, roy2);
                    }
#endif
                    celldx = (griddesc.lrc.fx - griddesc.urc.fx) /
            (ncellsy);
                    celldy = (griddesc.urc.fy - griddesc.ulc.fy) /
            (ncellsx);
                    if(griddesc.cellsize.fx < 5 || griddesc.cellsize.fy
< 5 ) {
                            errorprintf("Cells are too small for good analyis
(      %      .      1      f      x      %      .      1      f
pixels)\nContinuing.",griddesc.cellsize.fx,griddesc.cellsize.fy);
                    }
                    if(celldx > MAX(1,griddesc.cellsize.fx/10) ||
                       celldy > MAX(1,griddesc.cellsize.fy/10) ) {
                            errorprintf("Image is too rotated (%.1f x %.1f
pixels per cell).\n"
                                    "Subdivide cells or rescan image.
Continuing.",celldx, celldy);
                    }
                }
            }
        griddesc.nx = ncellsx, griddesc.ny = ncellsy;
        if(mbutton==ESCAPE) return 0;
        drawgrid(&ncellsx,&ncellsy,1);
    } while( yesnomouse("Try again?"));
    if (mbutton==ESCAPE) return 0;

setpolytogrid();
#if 0
    { /* Set up origin corner */
        static int n, flipped=0;
        char *opts[4];
        opts[0]="Blank in Upper Left (default)";
        opts[1]="Blank in Upper Right";
        opts[2]="Blank in Lower Left";
        opts[3]="Blank in Lower Right";
        n = mousechoose(opts, 4);
        if(mbutton==ESCAPE) return 0;
        flipped = yesnomouse("Active side down?");
        invertX = invertY = swapxy = 0;
        if(n<0) n=0;
        if(n&1) invertX=1;
```

```
            if(n&2) invertY=1;
            if(n==1 || n==2) swapxy = 1;
            if(flipped) swapxy = !swapxy;
        }
#endif
    pre_aligned = 1; /* Tell COUNT-CELLS that the grid has been
pre-aligned */
    return 1;
}
/**************************************************************
writeCELheader */
/* write the CEL file header */
writeCELheader( FILE *fp, int srcimg ){
    char comment[MAXCOMMENT];
    int xoff = 0, yoff=0;
    if( !fp ) return;
    if( srcimg==framenum ) {
            xoff = w0.x;
            yoff = w0.y;
    }
    fprintf( fp, "COLS/ROWS=%d  %d TOTAL=%d  %d OFFSET=%d  %d
CORNERS="
            "%.0f  %.0f,  %.0f  %.0f,  %.0f  %.0f,  %.0f  %.0f
AXIS-INVERT= %d  %d swapXY=%d\n",
        griddesc.nx, griddesc.ny, griddesc.totx,griddesc.toty,
        griddesc.offx, griddesc.offy,
        griddesc.ulc.fx-xoff, griddesc.ulc.fy-yoff,
        griddesc.urc.fx-xoff, griddesc.urc.fy-yoff,
        griddesc.lrc.fx-xoff, griddesc.lrc.fy-yoff,
        griddesc.llc.fx-xoff, griddesc.llc.fy-yoff,
        invertX, invertY, swapxy);
    frgetcomment(comment, MAXCOMMENT, srcimg );
    fprintf(fp,"%s\nX\tY\tMEAN\tSTDV\tNPIXELS\n", comment);
}
/**************************************************************
writecelfile */
/* Write a cel file from the current cellimage */
writecelfile(){
    char filename[80], *ptr;
    int ulx, uly, lrx, lry, x, y;
    long nzeros = 0;
    unsigned int minmean, maxmean;
    celldata cdat;
    coord oldpos = popuppos;
    FILE *fp;

if(!cellimage){
        errorprintf("Run count cells before writing cel file.");
        return;
    }
    strcpy(filename,datfilename);
    ptr = strrchr(filename,'.');
    if(ptr) strcpy(ptr,".CEL"); /* REPLACE EXTENSION WITH "CEL"
*/ popuppos.x = popuppos.y = 0; /* Reset the menu boxes from
```

```
imageroam */
    if(!fbgetfilename(filename,-80,"Cell file name","CEL")) goto
done;
    if(fileexists(filename)) goto done;
    fp = fopen( filename, "wt");
    if( !fp ){ seterror(FILE_DIDNT_OPEN, filename); goto done;}
    writeCELheader( fp, srcimg );
    ulx = uly = 0;
    lrx = griddesc.nx-1;
    lry = griddesc.ny-1;
    minmean = 0; maxmean = 32000;
    fbgetint( &ulx,0,0,"First column to save");
    fbgetint( &lrx,0,0,"Last col");
    fbgetint( &uly,0,0,"First row");
    fbgetint( &lry,0,0,"Last row");

if( yesnomouse("Check gray levels for desired intensity
range?")) {
        smov();
        fbgetint( &minmean, 0,0,"Darkest value to save");
        fbgetint( &maxmean, 0,0,"Brightest value to save");
    } for(y=uly; y<=lry; y++) {
        for( x = ulx; x<= lrx; x++){
            int ret;
            fgetrawrow(x, y, &cdat, 1, cellimage);
            if( minmean==0 || (cdat.intensity >= minmean &&
cdat.intensity<=maxmean )){
                ret = fprintf( fp, "%d\t %d\t %.1f\t %u\t %u\n",
                    x+griddesc.offx, y+griddesc.offy, cdat.intensity,
cdat.stdv, cdat.npix);
            }
            if( ret==EOF || ret<10 || ferror(fp) )
seterror(FILE_WRITE_FAILED,"Disk full.");

if( cdat.intensity == 0. ) nzeros++;
        }
    }
    if( nzeros > 3 ) errorprintf("There are %ld zero count cells.
Be sure to do 'Compute_All'",nzeros );
    fclose( fp );
done:
    popuppos = oldpos;
}
/***********************************************************
writebincelfile */
/* Write out the binary cel file */
writebincelfile(){
    FILE *fp;
    char filename[80], *ptr;
    int oldframe = framenum;

if(!cellimage){
        errorprintf("Run count cells before writing cel file.");
```

```c
        return;
    } strcpy(filename,datfilename);

ptr = strrchr(filename,'.');
    if(ptr) strcpy(ptr,".BCL"); /* REPLACE EXTENSION WITH "CEL" */ if(!fbgetfilename(filename,-80,"Binary cell file name","BCL")) return;
    if(fileexists(filename)) return;

framenum = cellimage;
    fsaveimage( filename );/**/
    framenum = oldframe;
    /* Write the header information at the end of the file */
    fp = fopen( filename, "at");
    writeCELheader( fp, srcimg );
    fclose( fp );
} test4(){
writecelfile();
#if 0
    int x, y, i, px, py;
    printf("\nulc,urc, %d %d; %d %d; llc,lrc,:%d %d; %d %d\n",
     ulc, urc, llc, lrc);
    for(y = 0; y < griddesc.ny; y++){
        cellposition(0,y,&px,&py);
        printf("y=%d, px=%d %d ", y, px, py);
        cellposition(griddesc.nx,y,&px,&py);
        printf("px=%d %d\n", px, py);
    }
#endif
}
```

==========================================================================

```
#include <math.h>
#define LIBRARY
#define textcolor _itextcolor
define textsize  _itextsize
/**************************************************************
data.h */
#ifndef __TURBOC__
#include "tc-msc.h"
endif
#include "acculib.h"
#define NEWNAMES
#ifdef NEWNAMES
#include "accushnm.h"
#endif
#include "accuprot.h"/**/
/*#include "accu.h"/**/
#define MAXPOLYDIM 32
#define NPOLYS 20
#define NKERNELS 1
extern int kernels[][9];
extern int kernelnum;

define MODE_RGB 3 extern int REDLUT, GREENLUT, BLUELUT, INPUTLUT;

extern int NFRAMES, NCOLS, NROWS, NLEVELS;

#define MAXLEVELS 256
ifdef __TURBOC__
#define MAXCOLS 2048
#else
#define MAXCOLS 1024
#endif
define MAXROWS 1024

/* IMAGE TYPES */
#define iFAST 0
#define iDOS  1
#define iEMM  2
#define iEXT  4
#define iFILE 8
define iFRAMEBUFFER 16 extern int clipmode;

define BOOL int
#define UINT unsigned int
#define ULONG unsigned long
define UCHAR unsigned char define MAX(a,b)        (((a) > (b)) ? (a) : (b))
define MIN(a,b)        (((a) < (b)) ? (a) : (b))
```

```
#define CLIP(a,b,c)         (((a) < (b)) ? (b) : (MIN(a,c)))

#define coord COORD
#define lcoord LCOORD
#define fcoord DCOORD
#define BOOL int  /* Boolean type */
#define MAXSCANLIST 3000
extern int scanlistlen;
extern coord *scanlist;
extern int dontmkscanlist;
struct optlist {
    char *label;     /* Name to call command */
    char *explanation;  /* Explanation, prompt, and keywords for help */
    int *n;          /* Pointer to variable, string, structure, or procedure */
    char type;       /* 'i'nteger, 'f'loat, 's'tring,'*'procedure,
                        'C'oord structure, 'a'rray of int, or 'm'acro */
    int lo,hi;       /* Range limits for int, float; dimensions of array,
                        lo=maxlen of string or lo=macro# for creating file# */
};
typedef struct optlist OPTLIST;
double intensitycal(double);
long   dcstr(),   lmin(),lmax(),  lclip(),  rlong(),  labs(), motposition();
double    fmin(),fmax(),    fclip(),    fcdist(),   fdist(), funitvect(),unitvect(), coordatan2();
double gettextsize();
double settextsize(double);
char *measureline();
void *malloc(), swapint(int *a, int *b), swapcoord(coord *a,coord *b);
void swapchar(char *a, char *b), swaplong(long *a, long *b), swapfloat(double *a, double *b);

float *geticaltable( void );
double intensitycal( double );
extern void (*idleproc)();
extern struct optlist options[];
extern int printtime,pdelay,debug,fromtty;
extern char pstr[];
extern coord normclip;
extern int demoflag;

/* INSPECTION APPLICATION VARIABLES */
extern int displaymode;
extern fcoord milsppix;
extern double xyratio;
extern char distanceunits[], intensityunits[];
extern int cameranum,sharpfactor,sharpwidth;
extern int equalizemax, smoothzoom;

/* frame buffer variables */
```

```
extern char imagefile[], serialroot[];
extern int serialnameflag, serialfilecounter, serialnplaces;
extern int framenum, lastemframe, cameranum;
extern int contrast,brightness, maxcontrast, maxbrightness,
genlockmode,interlace;
extern int color,bgrndcolor,overlaycolor,colormode,brightfeature;
extern int graphicsoverlay;
extern int pixelwidth, maxgray;
extern int autobright,autothreshflag, threshline;
extern int sthresh, dthresh[2], threshpcnt;
extern int cursorcolor, activecursor, polydim,polydims[],polynum;
extern int fcsmooth;
extern double gammacrt;
extern coord fw0,fw1, w0, w1,
p0,p1,polygon[],polys[][MAXPOLYDIM];
extern coord w0s[NPOLYS*2];
extern unsigned long histogram[MAXLEVELS];
extern int histmin,histmax;
extern unsigned char *lut,*_rlut,*_glut,*_blut,*gammalut;
extern int roiflag, polygonflag;
extern int cursorsize, lflashtime;
extern int asksd, mousemacro,
source_dest[2],ssource_dest[3],textscreen;
extern int undoframe, nundoframes, dataprint;
extern char printfile[];

extern int menuflag, menulines, menuup,helpup, nopopup;
extern coord popuppos;
extern int DefaultChooseItem;
extern coord textpos, textend, ulmargin, lrmargin;
extern double textsize, menusize, labelsize;
extern int fbtoo, textcolor, textbcolor, texttype, centerx,
centertext;
extern char fontname[];
extern coord charsize;
extern int _mousebutton, mbutton, mousefactor;
extern int batchmode;

extern int statscolor;

extern int temp;

extern coord edgeoffset;

/* MOUSELIST STRUCTURE: Mouse Menu option list. */
typedef struct {
    char *label; char *explanation; int *n; char type; int lo,hi;
    coord ulc,lrc; int level, color;
} mouselist ;

extern char fileprefix[],filesuffix[],
patientid[],menufilename[], progpath[];

extern int brightfeature;
```

```
#define BLOBTABLESIZE 256
extern int lastblob;
extern int bloblevello,bloblevelhi;
extern unsigned int blobarealo,blobareahi;

void printdata(char *title,char buftype, void *buf,int buflen,int ncols,char *fmt,
    ... );

/*#include "accuproto.h"/**/
/* TEMPORARY DEFINITIONS, TO CATCH CHANGES */
void dohist(ULONG *histogram, int frame);
void fasthist(int n,ULONG *histogram,int frame);
int falsecolor(int hmin, int hmax, BOOL wrap,BOOL smoothflag);
extern int cursortype;
```

What is claimed is:

1. An apparatus for imaging a sample located on a support, said apparatus comprising:

a body for immobilizing said support, said support comprising at least a first surface having said sample thereon;

an electromagnetic radiation source for generating excitation radiation having a first wavelength;

excitation optics for transforming a geometry of said excitation radiation to an excitation line, said excitation line having a focal plane, and directing said excitation line at said sample for exciting a plurality of regions thereon, said excitation line causing a labeled material on said sample to emit a response radiation, said response radiation having a second wavelength, said first wavelength being different from said second wavelength;

collection optics for collecting said response radiation from said plurality of regions;

a detector for sensing said response radiation received by said collection optics, said detector generating a signal proportional to the amount of radiation sensed thereon, said signal representing an image associated with said plurality of regions from said sample;

a translator for allowing a subsequent plurality of regions on said sample to be excited;

a processor for processing and storing said signal so as to generate a 2-dimensional image of said sample;

a mirror for directing said excitation radiation to excite said plurality of regions at a non-zero incident angle such that said response radiation and said excitation line reflected from said support are decoupled from each other; and a focuser for automatically focusing said sample in said focal plane of said excitation line, said focuser comprising first focusing optics for receiving said reflected excitation line and focusing said reflected excitation line to a first spot, a first slit located such that said first spot traverses said first slit when said translator moves said support in a direction relative to said excitation line, said first spot located at substantially a center of said first slit when said support is substantially in said focal plane, and a first radiation detector located behind said first slit for generating a signal proportional to an amount of radiation detected, said amount of radiation being greatest when said support is located in said focal plane.

2. The apparatus as recited in claim 1, wherein said focusing optics comprise:

a cylindrical lens for collimating said line reflected from said support; and a lens for focusing said line collimated by said cylindrical lens to a spot.

3. The apparatus as recited in claim 1, further comprising a position adjustor for locating said support automatically in a substantially perpendicular position relative to an optical axis of said collection optics, said position adjustor comprising:

a tilt stage for rotating said body until it reaches said substantially perpendicular position relative to the optical axis of said collection optics;

a beam splitter for directing a portion of said reflected excitation line from said first focusing optics;

second focusing optics for receiving said portion of said reflected excitation line from said beam splitter and focusing said reflected excitation line to a second spot;

a second slit located such that said second spot traverses said slit perpendicularly when said tilt stage rotates said support, said second spot located at substantially a center of said second slit when said support is substantially perpendicular relative to the optical axis of said collection optics; and a second radiation detector located behind said second slit for generating a signal proportional to an amount of radiation detected, said amount of radiation being greatest when said support is located substantially perpendicular relative to the optical axis of said collection optics.

4. The apparatus as recited in claim 3, wherein said substantially perpendicular position is substantially vertical.

5. The apparatus as recited in claim 3, wherein said tilt stage is controlled by said processor.

6. The apparatus as recited in claim 3, wherein said position adjustor comprises an air bearing system, said air bearing system comprising:

an optics head comprising a substantially planar plate, said planar plate comprising a first surface having a plurality of holes disposed therein, said plurality of holes being in communication with an air inlet;

a pump connected to said air inlet for flowing air through said plurality of holes;

a valve for regulating a flow of air from said air pump through said plurality of holes; and an air ballast to dampen air pressure variations, said optics head maintained in a relative position by air pressure through said plurality of holes such that said support is maintained in a substantially perpendicular position relative to said optical axis of said collection optics.

7. The apparatus as recited in claim 6, wherein said electromagnetic radiation source, excitation optics, collection optics and sensing detector are enclosed in said optics head.

8. The apparatus of claim 1, further comprising a support immobilized on said body, said support comprising at least a first surface having a sample thereon, said sample on said first surface of said support comprising a plurality of different oligonucleotide sequences, each of said plurality of different oligonucleotide sequences being in a separate known location on said first surface of said support.

9. The apparatus of claim 8, wherein said sample comprises more than 100 different oligonucleotide sequences in a separate known location on said first surface of said support.

10. The apparatus of claim 8, wherein said sample comprises more than 1000 different oligonucleotide sequences in a separate known location on said first surface of said support.

11. The apparatus of claim 8, wherein said sample comprises more than 10,000 different oligonucleotide sequences in a separate known location on said first surface of said support.

12. The apparatus of claim 8, wherein said sample comprises more than 100,000 different oligonucleotide sequences in a separate known location on said first surface of said support.

13. The apparatus of claim 8, wherein said support is glass.

14. A method of imaging a sample on a support, said method comprising the steps of:

immobilizing said support on a body;

exciting said sample on said support with an excitation radiation having a first wavelength from an electromagnetic radiation source, said excitation radiation having a focal plane and a linear geometry for exciting a plurality of region on said sample;

detecting a response radiation having a second wavelength in response to said excitation radiation, said response radiation representing an image of said plurality of regions;

exciting a subsequent plurality of regions on said sample;

processing and storing said response radiation to generate a 2-dimensional image of said sample; and auto-focusing said sample in said focal plane of said excitation radiation, said step of autofocusing comprising the steps of focusing a first surface of said support, coarse focusing on a second surface said support and finely focusing said second surface, wherein said step of focusing said first surface comprises the steps of directing said excitation radiation at said first surface of said support, said excitation radiation being reflected by said support, focusing said reflected excitation radiation through a slit, detecting an amount of reflected excitation radiation passing through said slit, said slit configured such that said reflected excitation radiation is located substantially at a center of said slit when said first surface is located in substantially the focal plane of said excitation radiation, determining if said amount of reflected excitation radiation passing through said slit has peaked, moving said support closer relative to said electromagnetic radiation source and repeating the directing, focusing, detecting, determining, and moving steps until said amount of reflected excitation radiation passing through said slit has peaked.

15. The method as recited in claim 14, wherein said step of coarse focusing said second surface comprises the steps of:

first moving said support closer relative to said electromagnetic radiation source, the distance which the said support is moved being equal to about half the thickness of said support;

directing said excitation radiation at said support, said excitation radiation being reflected by said support;

focusing said excitation radiation reflected by said support through said slit;

detecting an amount of said excitation radiation reflected by said support and passing through said slit;

determining if said amount of excitation radiation reflected by said support and passing through said slit has peaked;

second moving said support closer relative to said electromagnetic radiation source and repeating the directing, focusing, detecting, determining and moving steps until said amount of excitation radiation reflected by said support and passing through said slit has peaked.

16. The method as recited in claim 14, wherein said step of finely focusing said second surface comprises the steps of:

directing said excitation radiation at said support, said excitation radiation being reflected by said support;

focusing said excitation radiation reflected by said support through said slit;

detecting said amount of excitation radiation reflected by said support and passing through said slit, said slit configured such that said excitation radiation reflected by said support is located substantially at a center of said slit when said second surface is located substantially in the focal plane of said excitation radiation;

determining if said amount of excitation radiation reflected by said support and passing through said slit has peaked; and moving said support farther relative to said electromagnetic radiation source and repeating the directing, focusing, detecting, determining and moving steps until said amount of excitation radiation reflected by said support passing through said slit has reached a desired value.

17. The method of claim 14, wherein said sample excited in said exciting step comprises a plurality of different oligonucleotide sequences, each of said plurality of different oligonucleotide sequences being in a separate known location on said second surface of said support.

18. The method of claim 17, wherein said sample comprises more than 100 different oligonucleotide sequences in a separate known location on said second surface of said support.

19. The method of claim 17, wherein said sample comprises more than 1000 different oligonucleotide sequences in a separate known location on said second surface of said support.

20. The method of claim 17, wherein said sample comprises more than 10,000 different oligonucleotide sequences in a separate known location on said second surface of said support.

21. The method of claim 17, wherein said sample comprises more than 100,000 different oligonucleotide sequences in a separate known location on said second surface of said support.

22. The method of claim 17, wherein said support is glass.

* * * * *

UNITED STATES PATENT AND TRADEMARK OFFICE
CERTIFICATE OF CORRECTION

PATENT NO.   : 5,578,832
DATED        : November 26, 1996
INVENTOR(S)  : Trulson et al.

Page 1 of 1

It is certified that error appears in the above-identified patent and that said Letters Patent is hereby corrected as shown below:

Column 1,
Line 4, please insert the following:

-- GOVERNMENT RIGHTS NOTICE

This invention was made with Government support under grant nos. DE-FG03-92ER81275 (SBIR) awarded by the Department of Energy and/or H600813-1, -2 between Affymetrix, Inc. and the National Institutes of Health. The Government has certain rights in this invention. --

Signed and Sealed this

Eighteenth Day of September, 2001

*Attest:*

*Attesting Officer*

NICHOLAS P. GODICI
*Acting Director of the United States Patent and Trademark Office*